United States Patent
Kas

(10) Patent No.: US 10,114,021 B2
(45) Date of Patent: Oct. 30, 2018

(54) BIOMARKER FOR DIAGNOSIS, PREDICTION AND/OR PROGNOSIS OF ACUTE HEART FAILURE AND USES THEREOF

(71) Applicant: MyCartis NV, Ghent (BE)

(72) Inventor: Koen Kas, Schilde (BE)

(73) Assignee: MYCARTIS NV, Ghent (BE)

( * ) Notice: Subject to any disclaimer, the term of this patent is extended or adjusted under 35 U.S.C. 154(b) by 54 days.

(21) Appl. No.: 15/242,044

(22) Filed: Aug. 19, 2016

(65) Prior Publication Data

US 2017/0010265 A1    Jan. 12, 2017

Related U.S. Application Data

(63) Continuation of application No. 13/141,061, filed as application No. PCT/EP2010/051016 on Jan. 28, 2010.

(60) Provisional application No. 61/148,585, filed on Jan. 30, 2009.

(30) Foreign Application Priority Data

Jan. 30, 2009   (EP) ..................................... 09151816
Oct. 19, 2009   (WO) ................. PCT/EP2009/063690

(51) Int. Cl.
*G01N 33/573* (2006.01)
*G01N 33/558* (2006.01)
*G01N 33/68* (2006.01)

(52) U.S. Cl.
CPC .... *G01N 33/573* (2013.01); *C12Y 108/03002* (2013.01); *G01N 33/558* (2013.01); *G01N 33/6893* (2013.01); *G01N 2333/90212* (2013.01); *G01N 2560/00* (2013.01); *G01N 2800/325* (2013.01); *G01N 2800/52* (2013.01)

(58) Field of Classification Search
CPC .......................... G01N 33/558; G01N 33/6893
USPC ....................... 435/7.1, 7.92, 7.93, 7.94, 7.95
See application file for complete search history.

(56) References Cited

U.S. PATENT DOCUMENTS

| 2005/0152836 A1 | 7/2005 | Ashley et al. |
| 2010/0190686 A1* | 7/2010 | Wells ................. G01N 33/5023 514/5.9 |
| 2011/0275536 A1 | 11/2011 | Kas |

FOREIGN PATENT DOCUMENTS

| EP | 1 327 886 | 7/2003 |
| WO | WO 2008/037720 | 4/2008 |
| WO | WO 2009/002472 | 12/2008 |

OTHER PUBLICATIONS

International Search Report dated Apr. 11, 2010 and issued to international application No. PCT/EP2010/051016.
Office Action issued in corresponding Japanese Patent Application No. 2011-546847, dated Jun. 11, 2013.
Clerico, et al. Comparison of the Diagnostic Accuracy of Brain Natriuretic Peptide (BNP) and the N-terminal Part of the Propeptide of BNP Immunoassays in Chronic and Acute Heart Failure: A systemic Review, Clinical Chemistry, vol. 53, No. 5, pp. 813-822, May 2007.

* cited by examiner

*Primary Examiner* — Antonio Galisteo Gonzalez
(74) *Attorney, Agent, or Firm* — Knobbe Martens Olson & Bear LLP

(57) ABSTRACT

The application discloses Quiescin Q6 as a new biomarker for acute heart failure. Methods for determining the quantity of Quiescin Q6 in a sample from a subject are described. The quantity of Quiescin Q6 is determined by contacting the sample with one or more binding agents capable of specifically binding to Quiescin Q6.

12 Claims, 17 Drawing Sheets

Specification includes a Sequence Listing.

FIG 1

(A) Quiescin Q6 isoform-1, from O00391-1

MRRCNSGSGPPPSLLLLLLWLLAVPGANAAPRSALYSPSDPLTLLQADT
VRGAVLGSRSAWAVEFFASWCGHCIAFAPTWKALAEDVKAWRPALYL
AALDCAEETNSAVCRDFNIPGFPTVRFFKAFTKNGSGAVFPVAGADVQT
LRERLIDALESHHDTWPPACPPLEPAKLEEIDGFFARNNEEYLALIFEKG
GSYLGREVALDLSQHKGVAVRRVLNTEANVVRKFGVTDFPSCYLLFRN
GSVSRVPVLMESRSFYTAYLQRLSGLTREAAQTTVAPTTANKIAPTVWK
LADRSKIYMADLESALHYILRIEVGRFPVLEGQRLVALKKFVAVLAKYFP
GRPLVQNFLHSVNEWLKRQKRNKIPYSFFKTALDDRKEGAVLAKKVNWI
GCQGSEPHFRGFPCSLWVLFHFLTVQAARQNVDHSQEAAKAKEVLPAI
RGYVHYFFGCRDCASHFEQMAAASMHRVGSPNAAVLWLWSSHNRVN
ARLAGAPSEDPQFPKVQWPPRELCSACHNERLDVPVWDVEATLNFLK
AHFSPSNIILDFPAAGSAARRDVQNVAAAPELAMGALELESRNSTLDPG
KPEMMKSPTNTTPHVPAEGPEASRPPKLHPGLRAAPGQEPPEHMAEL
QRNEQEQPLGQWHLSKRDTGAALLAESRAEKNRLWGPLEVRRVGRSS
KQLVDIPEGQLEARAGRGRGQWLQVLGGGFSYLDISLCVGLYSLSFMG
LLAMYTYFQAKIRALKGHAGHPAA (SEQ ID NO: 1)

(B) Quiescin Q6 isoform-2, from O00391-2

MRRCNSGSGPPPSLLLLLLWLLAVPGANAAPRSALYSPSDPLTLLQADT
VRGAVLGSRSAWAVEFFASWCGHCIAFAPTWKALAEDVKAWRPALYL
AALDCAEETNSAVCRDFNIPGFPTVRFFKAFTKNGSGAVFPVAGADVQT
LRERLIDALESHHDTWPPACPPLEPAKLEEIDGFFARNNEEYLALIFEKG
GSYLGREVALDLSQHKGVAVRRVLNTEANVVRKFGVTDFPSCYLLFRN
GSVSRVPVLMESRSFYTAYLQRLSGLTREAAQTTVAPTTANKIAPTVWK
LADRSKIYMADLESALHYILRIEVGRFPVLEGQRLVALKKFVAVLAKYFP
GRPLVQNFLHSVNEWLKRQKRNKIPYSFFKTALDDRKEGAVLAKKVNWI
GCQGSEPHFRGFPCSLWVLFHFLTVQAARQNVDHSQEAAKAKEVLPAI
RGYVHYFFGCRDCASHFEQMAAASMHRVGSPNAAVLWLWSSHNRVN
ARLAGAPSEDPQFPKVQWPPRELCSACHNERLDVPVWDVEATLNFLK
AHFSPSNIILDFPAAGSAARRDVQNVAAAPELAMGALELESRNSTLDPG
KPEMMKSPTNTTPHVPAEGPELI (SEQ ID NO: 2)

FIG 2

MRRCNSGSGPPPSLLLLLLWLLAVPGANAAPRSALYSPSDPLTLLQAD
TVRGAVLGSRSAWAVEFFASWCGHCIAFAPTWKALAEDVKAWRPALYL
AALDCAEETNSAVCRDFNIPGFPTVRFFKAFTKNGSGAVFPVAGADVQT
LRERLIDALESHHDTWPPACPPLEPAKLEEIDGFFARNNEEYLALIFEKG
GSYLGREVALDLSQHKGVAVRRVLNTEANVVRKFGVTDFPSCYLLFRN
GSVSRVPVLMESRSFYTAYLQRLSGLTREAAQTTVAPTTANKIAPTVWK
LADRSKIYMADLESALHYILRIEVGRFPVLEGQRLVALKKFVAVLAKYFP
GRPLVQNFLHSVNEWLKRQKRNKIPYSFFKTALDDRKEGAVLAKKVNW
IGCQGSEPHFRGFPCSLWVLFHFLTVQAARQNVDHSQEAAKAKEVLP
AIRGYVHYFFGCRDCASHFEQMAAASMHRVGSPNAAVLWLWSSHNRV
NARLAGAPSEDPQFPKVQWPPRELCSACHNERLDVPVWDVEATLNFL
KAHFSPSNIILDFPAAGSAARRDVQNVAAAPELAMGALELESRNSTLDP
GKPEMMKSPTNTTPHVPAEGPEASRppklhpglraapgqeppehmaelqrneqeq
plgqwhlskrdtgaallaesraeknrlwgplevrrvgrsskqlvdipegqlearagrgrgqwlqvlgggf
syldislcvglyslsfmgllamytyfqakiralkghaghpaa (SEQ ID NO: 1)

FIG 3

(A) Natriuretic peptide precursor B preproprotein, NP_002512

MDPQTAPSRALLLLLFLHLAFLGGRSHPLGSPGSASDLETSGLQEQRN
HLQGKLSELQVEQTSLEPLQESPRPTGVWKSREVATEGIRGHRKMVLY
TLRAPRSPKMVQGSGCFGRKMDRISSSSGLGCKVLRRH (SEQ ID NO: 3)

(B) proBNP, from NP_002512

HPLGSPGSASDLETSGLQEQRNHLQGKLSELQVEQTSLEPLQESPRPT
GVWKSREVATEGIRGHRKMVLYTLRAPRSPKMVQGSGCFGRKMDRIS
SSSGLGCKVLRRH (SEQ ID NO: 4)

(C) NTproBNP, from NP_002512

HPLGSPGSASDLETSGLQEQRNHLQGKLSELQVEQTSLEPLQESPRPT
GVWKSREVATEGIRGHRKMVLYTLRAPR (SEQ ID NO: 5)

(D) BNP, from NP_002512

SPKMVQGSGCFGRKMDRISSSSGLGCKVLRRH (SEQ ID NO: 6)

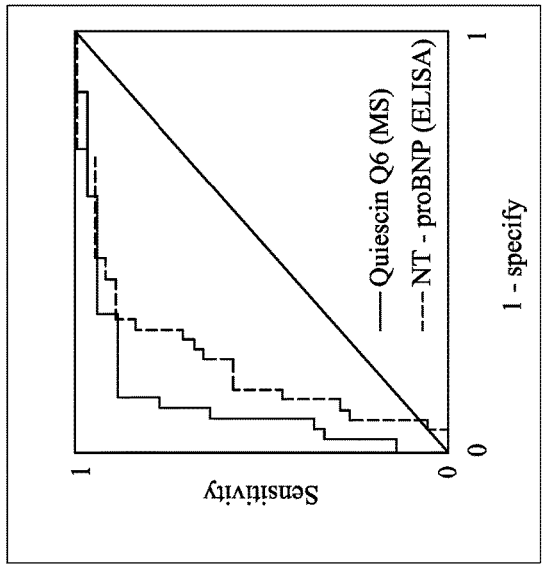
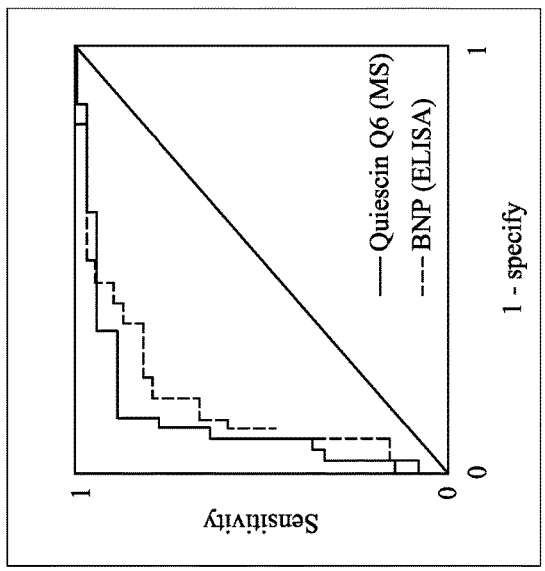
FIG. 7A
| | BNP | NT-proBNP | Quiesc. Q6 |
|---|---|---|---|
| | ELISA | ELISA | MS |
| Median AUC | 0.84 | 0.80 | 0.89 |
| 95% CI | 0.74 - 0.92 | 0.69 - 0.89 | 0.79 - 0.96 |

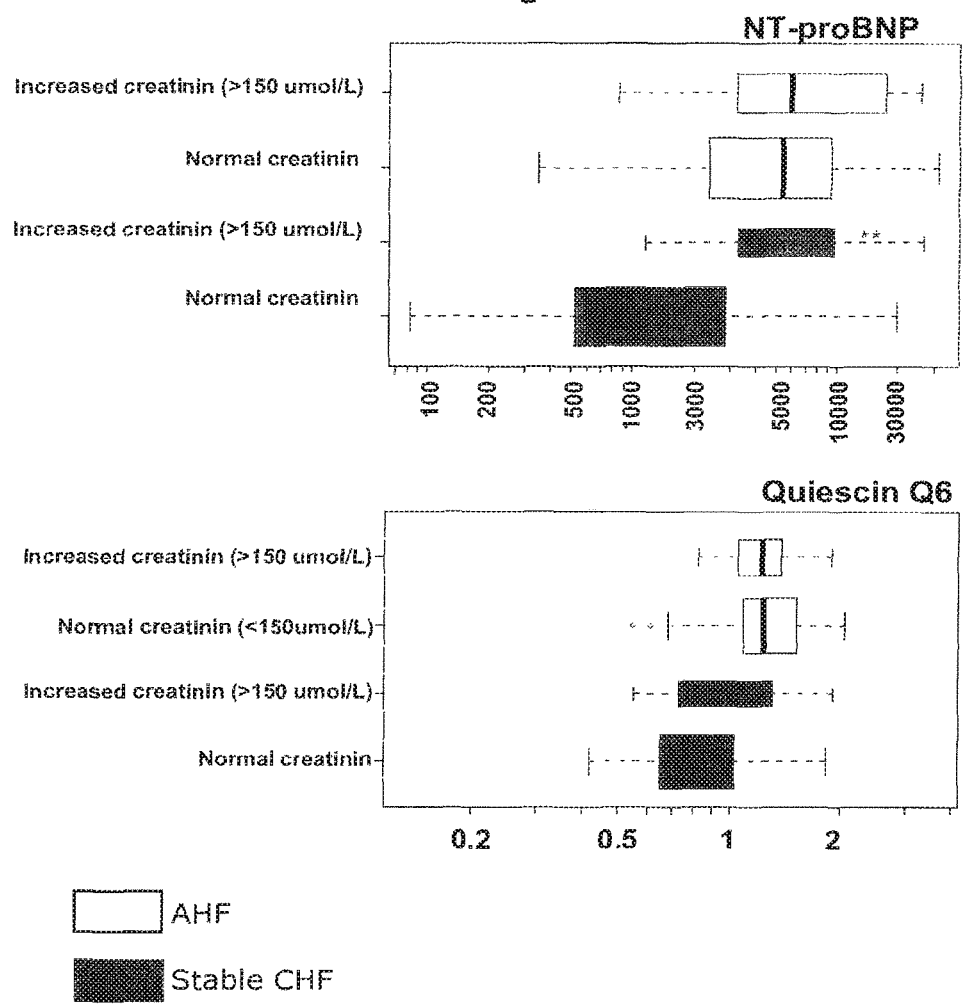

FIG 14
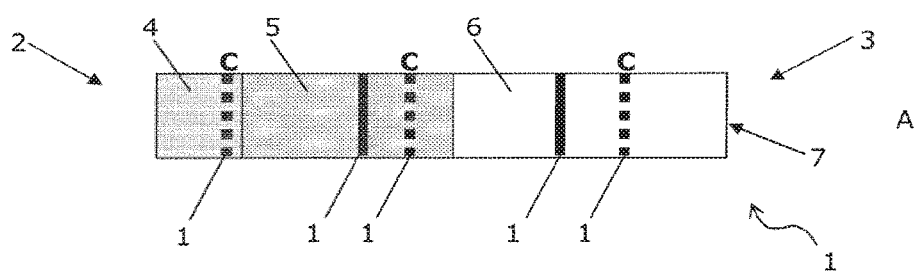
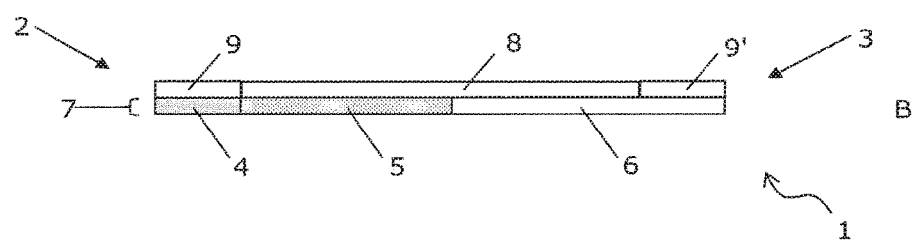
FIG 15
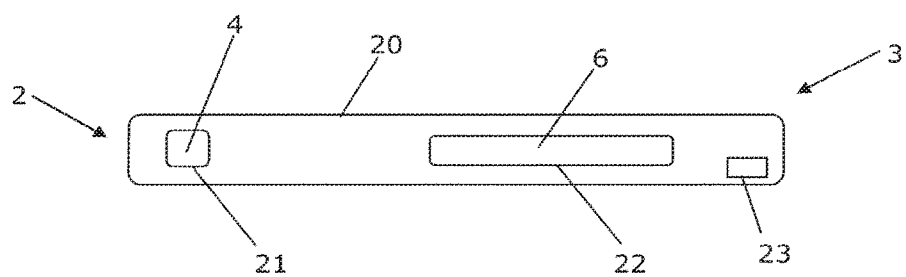

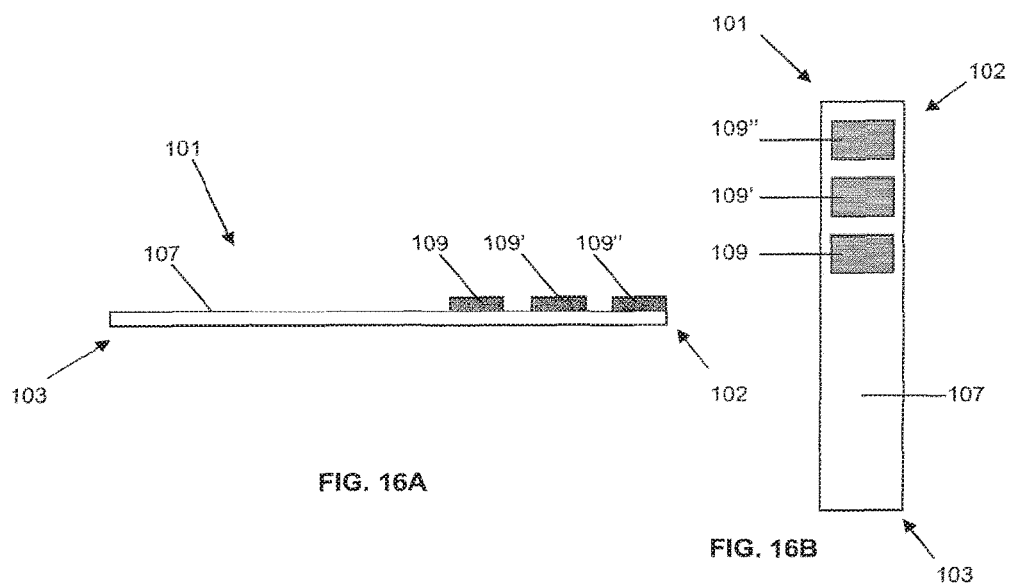

SEQUENCE LISTING

<160> NUMBER OF SEQ ID NOS: 10

<210> SEQ ID NO 1
<211> LENGTH: 747
<212> TYPE: PRT
<213> ORGANISM: Homo sapiens

<400> SEQUENCE: 1

```
Met Arg Arg Cys Asn Ser Gly Ser Gly Pro Pro Pro Ser Leu Leu Leu
1               5                   10                  15

Leu Leu Leu Trp Leu Leu Ala Val Pro Gly Ala Asn Ala Ala Pro Arg
            20                  25                  30

Ser Ala Leu Tyr Ser Pro Ser Asp Pro Leu Thr Leu Leu Gln Ala Asp
        35                  40                  45

Thr Val Arg Gly Ala Val Leu Gly Ser Arg Ser Ala Trp Ala Val Glu
50                  55                  60

Phe Phe Ala Ser Trp Cys Gly His Cys Ile Ala Phe Ala Pro Thr Trp
65                  70                  75                  80

Lys Ala Leu Ala Glu Asp Val Lys Ala Trp Arg Pro Ala Leu Tyr Leu
                85                  90                  95

Ala Ala Leu Asp Cys Ala Glu Glu Thr Asn Ser Ala Val Cys Arg Asp
            100                 105                 110

Phe Asn Ile Pro Gly Phe Pro Thr Val Arg Phe Phe Lys Ala Phe Thr
        115                 120                 125

Lys Asn Gly Ser Gly Ala Val Phe Pro Val Ala Gly Ala Asp Val Gln
130                 135                 140

Thr Leu Arg Glu Arg Leu Ile Asp Ala Leu Glu Ser His His Asp Thr
145                 150                 155                 160

Trp Pro Pro Ala Cys Pro Pro Leu Glu Pro Ala Lys Leu Glu Glu Ile
                165                 170                 175

Asp Gly Phe Phe Ala Arg Asn Asn Glu Glu Tyr Leu Ala Leu Ile Phe
            180                 185                 190

Glu Lys Gly Gly Ser Tyr Leu Gly Arg Glu Val Ala Leu Asp Leu Ser
        195                 200                 205

Gln His Lys Gly Val Ala Val Arg Arg Val Leu Asn Thr Glu Ala Asn
210                 215                 220

Val Val Arg Lys Phe Gly Val Thr Asp Phe Pro Ser Cys Tyr Leu Leu
225                 230                 235                 240

Phe Arg Asn Gly Ser Val Ser Arg Val Pro Val Leu Met Glu Ser Arg
                245                 250                 255

Ser Phe Tyr Thr Ala Tyr Leu Gln Arg Leu Ser Gly Leu Thr Arg Glu
            260                 265                 270
```

-continued

Ala Ala Gln Thr Thr Val Ala Pro Thr Thr Ala Asn Lys Ile Ala Pro
            275             280             285

Thr Val Trp Lys Leu Ala Asp Arg Ser Lys Ile Tyr Met Ala Asp Leu
    290             295             300

Glu Ser Ala Leu His Tyr Ile Leu Arg Ile Glu Val Gly Arg Phe Pro
305             310             315             320

Val Leu Glu Gly Gln Arg Leu Val Ala Leu Lys Lys Phe Val Ala Val
                325             330             335

Leu Ala Lys Tyr Phe Pro Gly Arg Pro Leu Val Gln Asn Phe Leu His
            340             345             350

Ser Val Asn Glu Trp Leu Lys Arg Gln Lys Arg Asn Lys Ile Pro Tyr
    355             360             365

Ser Phe Phe Lys Thr Ala Leu Asp Asp Arg Lys Glu Gly Ala Val Leu
370             375             380

Ala Lys Lys Val Asn Trp Ile Gly Cys Gln Gly Ser Glu Pro His Phe
385             390             395             400

Arg Gly Phe Pro Cys Ser Leu Trp Val Leu Phe His Phe Leu Thr Val
                405             410             415

Gln Ala Ala Arg Gln Asn Val Asp His Ser Gln Glu Ala Ala Lys Ala
            420             425             430

Lys Glu Val Leu Pro Ala Ile Arg Gly Tyr Val His Tyr Phe Phe Gly
    435             440             445

Cys Arg Asp Cys Ala Ser His Phe Glu Gln Met Ala Ala Ala Ser Met
450             455             460

His Arg Val Gly Ser Pro Asn Ala Ala Val Leu Trp Leu Trp Ser Ser
465             470             475             480

His Asn Arg Val Asn Ala Arg Leu Ala Gly Ala Pro Ser Glu Asp Pro
                485             490             495

Gln Phe Pro Lys Val Gln Trp Pro Pro Arg Glu Leu Cys Ser Ala Cys
            500             505             510

His Asn Glu Arg Leu Asp Val Pro Val Trp Asp Val Glu Ala Thr Leu
    515             520             525

Asn Phe Leu Lys Ala His Phe Ser Pro Ser Asn Ile Ile Leu Asp Phe
530             535             540

Pro Ala Ala Gly Ser Ala Ala Arg Arg Asp Val Gln Asn Val Ala Ala
545             550             555             560

Ala Pro Glu Leu Ala Met Gly Ala Leu Glu Leu Glu Ser Arg Asn Ser
                565             570             575

Thr Leu Asp Pro Gly Lys Pro Glu Met Met Lys Ser Pro Thr Asn Thr
            580             585             590

Thr Pro His Val Pro Ala Glu Gly Pro Glu Ala Ser Arg Pro Pro Lys
    595             600             605

Leu His Pro Gly Leu Arg Ala Ala Pro Gly Gln Glu Pro Pro Glu His
610             615             620

Met Ala Glu Leu Gln Arg Asn Glu Gln Glu Gln Pro Leu Gly Gln Trp
625             630             635             640

His Leu Ser Lys Arg Asp Thr Gly Ala Ala Leu Leu Ala Glu Ser Arg
                645             650             655

Ala Glu Lys Asn Arg Leu Trp Gly Pro Leu Glu Val Arg Arg Val Gly
            660             665             670

Arg Ser Ser Lys Gln Leu Val Asp Ile Pro Glu Gly Gln Leu Glu Ala
    675             680             685

```
Arg Ala Gly Arg Gly Arg Gly Gln Trp Leu Gln Val Leu Gly Gly Gly
    690             695                 700

Phe Ser Tyr Leu Asp Ile Ser Leu Cys Val Gly Leu Tyr Ser Leu Ser
705             710                 715                 720

Phe Met Gly Leu Leu Ala Met Tyr Thr Tyr Phe Gln Ala Lys Ile Arg
            725                 730                 735

Ala Leu Lys Gly His Ala Gly His Pro Ala Ala
            740             745

<210> SEQ ID NO 2
<211> LENGTH: 604
<212> TYPE: PRT
<213> ORGANISM: Homo sapiens

<400> SEQUENCE: 2

Met Arg Arg Cys Asn Ser Gly Ser Gly Pro Pro Ser Leu Leu Leu
1               5                   10                  15

Leu Leu Leu Trp Leu Leu Ala Val Pro Gly Ala Asn Ala Ala Pro Arg
            20                  25                  30

Ser Ala Leu Tyr Ser Pro Ser Asp Pro Leu Thr Leu Leu Gln Ala Asp
            35                  40                  45

Thr Val Arg Gly Ala Val Leu Gly Ser Arg Ser Ala Trp Ala Val Glu
50                  55                  60

Phe Phe Ala Ser Trp Cys Gly His Cys Ile Ala Phe Ala Pro Thr Trp
65              70                  75                  80

Lys Ala Leu Ala Glu Asp Val Lys Ala Trp Arg Pro Ala Leu Tyr Leu
            85                  90                  95

Ala Ala Leu Asp Cys Ala Glu Glu Thr Asn Ser Ala Val Cys Arg Asp
            100                 105                 110

Phe Asn Ile Pro Gly Phe Pro Thr Val Arg Phe Phe Lys Ala Phe Thr
            115                 120                 125

Lys Asn Gly Ser Gly Ala Val Phe Pro Val Ala Gly Ala Asp Val Gln
            130                 135                 140

Thr Leu Arg Glu Arg Leu Ile Asp Ala Leu Glu Ser His His Asp Thr
145                 150                 155                 160

Trp Pro Pro Ala Cys Pro Pro Leu Glu Pro Ala Lys Leu Glu Glu Ile
                165                 170                 175

Asp Gly Phe Phe Ala Arg Asn Asn Glu Glu Tyr Leu Ala Leu Ile Phe
            180                 185                 190

Glu Lys Gly Gly Ser Tyr Leu Gly Arg Glu Val Ala Leu Asp Leu Ser
            195                 200                 205

Gln His Lys Gly Val Ala Val Arg Arg Val Leu Asn Thr Glu Ala Asn
            210                 215                 220

Val Val Arg Lys Phe Gly Val Thr Asp Phe Pro Ser Cys Tyr Leu Leu
225                 230                 235                 240

Phe Arg Asn Gly Ser Val Ser Arg Val Pro Val Leu Met Glu Ser Arg
                245                 250                 255

Ser Phe Tyr Thr Ala Tyr Leu Gln Arg Leu Ser Gly Leu Thr Arg Glu
            260                 265                 270

Ala Ala Gln Thr Thr Val Ala Pro Thr Thr Ala Asn Lys Ile Ala Pro
            275                 280                 285

Thr Val Trp Lys Leu Ala Asp Arg Ser Lys Ile Tyr Met Ala Asp Leu
            290                 295                 300

Glu Ser Ala Leu His Tyr Ile Leu Arg Ile Glu Val Gly Arg Phe Pro
305                 310                 315                 320
```

-continued

Val Leu Glu Gly Gln Arg Leu Val Ala Leu Lys Lys Phe Val Ala Val
            325                 330                 335

Leu Ala Lys Tyr Phe Pro Gly Arg Pro Leu Val Gln Asn Phe Leu His
        340                 345                 350

Ser Val Asn Glu Trp Leu Lys Arg Gln Lys Arg Asn Lys Ile Pro Tyr
        355                 360                 365

Ser Phe Phe Lys Thr Ala Leu Asp Asp Arg Lys Glu Gly Ala Val Leu
        370                 375                 380

Ala Lys Lys Val Asn Trp Ile Gly Cys Gln Gly Ser Glu Pro His Phe
385                 390                 395                 400

Arg Gly Phe Pro Cys Ser Leu Trp Val Leu Phe His Phe Leu Thr Val
            405                 410                 415

Gln Ala Ala Arg Gln Asn Val Asp His Ser Gln Glu Ala Ala Lys Ala
        420                 425                 430

Lys Glu Val Leu Pro Ala Ile Arg Gly Tyr Val His Tyr Phe Phe Gly
        435                 440                 445

Cys Arg Asp Cys Ala Ser His Phe Glu Gln Met Ala Ala Ala Ser Met
    450                 455                 460

His Arg Val Gly Ser Pro Asn Ala Ala Val Leu Trp Leu Trp Ser Ser
465                 470                 475                 480

His Asn Arg Val Asn Ala Arg Leu Ala Gly Ala Pro Ser Glu Asp Pro
            485                 490                 495

Gln Phe Pro Lys Val Gln Trp Pro Pro Arg Glu Leu Cys Ser Ala Cys
        500                 505                 510

His Asn Glu Arg Leu Asp Val Pro Val Trp Asp Val Glu Ala Thr Leu
        515                 520                 525

Asn Phe Leu Lys Ala His Phe Ser Pro Ser Asn Ile Ile Leu Asp Phe
    530                 535                 540

Pro Ala Ala Gly Ser Ala Ala Arg Arg Asp Val Gln Asn Val Ala Ala
545                 550                 555                 560

Ala Pro Glu Leu Ala Met Gly Ala Leu Glu Leu Glu Ser Arg Asn Ser
            565                 570                 575

Thr Leu Asp Pro Gly Lys Pro Glu Met Met Lys Ser Pro Thr Asn Thr
        580                 585                 590

Thr Pro His Val Pro Ala Glu Gly Pro Glu Leu Ile
        595                 600

<210> SEQ ID NO 3
<211> LENGTH: 134
<212> TYPE: PRT
<213> ORGANISM: Homo sapiens

<400> SEQUENCE: 3

Met Asp Pro Gln Thr Ala Pro Ser Arg Ala Leu Leu Leu Leu Leu Phe
1               5                   10                  15

Leu His Leu Ala Phe Leu Gly Gly Arg Ser His Pro Leu Gly Ser Pro
            20                  25                  30

Gly Ser Ala Ser Asp Leu Glu Thr Ser Gly Leu Gln Glu Gln Arg Asn
        35                  40                  45

His Leu Gln Gly Lys Leu Ser Glu Leu Gln Val Glu Gln Thr Ser Leu
    50                  55                  60

Glu Pro Leu Gln Glu Ser Pro Arg Pro Thr Gly Val Trp Lys Ser Arg
65                  70                  75                  80

Glu Val Ala Thr Glu Gly Ile Arg Gly His Arg Lys Met Val Leu Tyr
            85                  90                  95

```
Thr Leu Arg Ala Pro Arg Ser Pro Lys Met Val Gln Gly Ser Gly Cys
            100                 105                 110

Phe Gly Arg Lys Met Asp Arg Ile Ser Ser Ser Ser Gly Leu Gly Cys
        115                 120                 125

Lys Val Leu Arg Arg His
    130
```

<210> SEQ ID NO 4
<211> LENGTH: 108
<212> TYPE: PRT
<213> ORGANISM: Homo sapiens

<400> SEQUENCE: 4

```
His Pro Leu Gly Ser Pro Gly Ser Ala Ser Asp Leu Glu Thr Ser Gly
1               5                   10                  15

Leu Gln Glu Gln Arg Asn His Leu Gln Gly Lys Leu Ser Glu Leu Gln
            20                  25                  30

Val Glu Gln Thr Ser Leu Glu Pro Leu Gln Glu Ser Pro Arg Pro Thr
        35                  40                  45

Gly Val Trp Lys Ser Arg Glu Val Ala Thr Glu Gly Ile Arg Gly His
    50                  55                  60

Arg Lys Met Val Leu Tyr Thr Leu Arg Ala Pro Arg Ser Pro Lys Met
65                  70                  75                  80

Val Gln Gly Ser Gly Cys Phe Gly Arg Lys Met Asp Arg Ile Ser Ser
                85                  90                  95

Ser Ser Gly Leu Gly Cys Lys Val Leu Arg Arg His
            100                 105
```

<210> SEQ ID NO 5
<211> LENGTH: 76
<212> TYPE: PRT
<213> ORGANISM: Homo sapiens

<400> SEQUENCE: 5

```
His Pro Leu Gly Ser Pro Gly Ser Ala Ser Asp Leu Glu Thr Ser Gly
1               5                   10                  15

Leu Gln Glu Gln Arg Asn His Leu Gln Gly Lys Leu Ser Glu Leu Gln
            20                  25                  30

Val Glu Gln Thr Ser Leu Glu Pro Leu Gln Glu Ser Pro Arg Pro Thr
        35                  40                  45

Gly Val Trp Lys Ser Arg Glu Val Ala Thr Glu Gly Ile Arg Gly His
    50                  55                  60

Arg Lys Met Val Leu Tyr Thr Leu Arg Ala Pro Arg
65                  70                  75
```

<210> SEQ ID NO 6
<211> LENGTH: 32
<212> TYPE: PRT
<213> ORGANISM: Homo sapiens

<400> SEQUENCE: 6

```
Ser Pro Lys Met Val Gln Gly Ser Gly Cys Phe Gly Arg Lys Met Asp
1               5                   10                  15

Arg Ile Ser Ser Ser Ser Gly Leu Gly Cys Lys Val Leu Arg Arg His
            20                  25                  30
```

```
<210> SEQ ID NO 7
<211> LENGTH: 19
<212> TYPE: PRT
<213> ORGANISM: Artificial
<220> FEATURE:
<223> OTHER INFORMATION: Peptide

<400> SEQUENCE: 7

Ser Ala Leu Tyr Ser Pro Ser Asp Pro Leu Thr Leu Leu Gln Ala Asp
1               5                   10                  15

Thr Val Arg

<210> SEQ ID NO 8
<211> LENGTH: 10
<212> TYPE: PRT
<213> ORGANISM: Artificial
<220> FEATURE:
<223> OTHER INFORMATION: Peptide

<400> SEQUENCE: 8

Ser Phe Phe Lys Thr Ala Leu Asp Asp Arg
1               5                   10

<210> SEQ ID NO 9
<211> LENGTH: 20
<212> TYPE: PRT
<213> ORGANISM: Artificial
<220> FEATURE:
<223> OTHER INFORMATION: Peptide

<400> SEQUENCE: 9

Gln Asn Val Asp His Ser Gln Glu Ala Ala Lys Ala Lys Glu Val Leu
1               5                   10                  15

Pro Ala Ile Arg
            20

<210> SEQ ID NO 10
<211> LENGTH: 13
<212> TYPE: PRT
<213> ORGANISM: Artificial
<220> FEATURE:
<223> OTHER INFORMATION: Peptide

<400> SEQUENCE: 10

Leu Ala Gly Ala Pro Ser Glu Asp Pro Gln Phe Pro Lys
1               5                   10
```

BIOMARKER FOR DIAGNOSIS, PREDICTION AND/OR PROGNOSIS OF ACUTE HEART FAILURE AND USES THEREOF

CROSS-REFERENCE TO RELATED APPLICATIONS

This application is a continuation of U.S. application Ser. No. 13/141,061, filed Jun. 20, 2011 which is the U.S. National Phase under 35 U.S.C. § 371 of International Application PCT/EP2010/051016, filed Jan. 28, 2010, which claims priority to EP 09151816.7, filed Jan. 30, 2009, U.S. Provisional Application No. 61/148,585, filed Jan. 30, 2009, and PCT/EP2009/063690, filed Oct. 19, 2009.

FIELD OF THE INVENTION

The invention relates to protein- and/or peptide-based biomarkers and to agents specifically binding thereto, for use in predicting, diagnosing and/or prognosticating diseases or conditions in subjects. More particularly, the application discloses certain proteins and/or peptides as new biomarkers for acute heart failure; methods for predicting, diagnosing and/or prognosticating acute heart failure based on measuring said biomarker proteins and/or peptides; and kits and devices for measuring said proteins and/or peptides and/or performing said methods.

BACKGROUND OF THE INVENTION

In many diseases and conditions, a favourable outcome of prophylactic and/or therapeutic treatments is strongly correlated with early and/or accurate prediction, diagnosis and/or prognosis of the disease or condition. Therefore, there exists a continuous need for additional and preferably improved manners for early and/or accurate prediction, diagnosis and/or prognosis of diseases and conditions to guide the treatment choices.

Heart failure is a major public health issue in developed countries and is the cause of considerable morbidity and mortality among older adults. It is usually a chronic disease characterised by frequent recurrent decompensation leading to worsening breathing problems. Moreover, 5 years after diagnosis 50% of heart failure patients will have died from the disease.

Acute heart failure (AHF) is a sudden inability of the heart to pump efficiently and where it can no longer foresee the bodily demands for oxygen. AHF is the cause of over two million hospitalisations annually in US and Europe, and displays a mortality rate of about 20-40% within one year of hospital discharge in many populations. About 90% of AHF admissions are typically from patients with chronic heart disease, the remaining about 10% are de novo patients. The clinical signs of heart disease and AHF are often non-specific which can make unambiguous diagnosis demanding.

A common symptom of AHF is the shortness of breath (dyspnea or dyspnoea). However, usually only a fraction of subjects presenting with dyspnea upon admission to a physician or clinic suffer from AHF. Therefore, a rapid, proper and effective treatment of AHF requires to adequately distinguish AHF patients from patients having dyspnea due to other causes.

Currently, diagnosis of AHF is mainly done on the basis of clinical signs, such as, ECG, chest X-ray, etc. One biomarker often used to complement these diagnostic criteria of AHF such as in emergency setting is B-type natriuretic peptide (BNP). Typically, BNP lower than 100 pg/mL is regarded as a "rule-out" criterion for heart failure, whereas BNP higher than 400 pg/mL is seen as a "rule-in" criterion for AHF. Although BNP is sensitive, its specificity is relatively low, and is especially problematic due to the "grey zone" between 100-400 pg/mL. For example, Chung et al. 2006 (Am Heart J 152(5): 949-55) have determined that the BNP cut point of 100 pg/mL has 100% sensitivity but only 41% specificity for diagnosing AHF, whereas the cut point of 400 pg/mL has 87% sensitivity and 76% specificity.

Also, BNP levels vary with age, sex, weight and other medical conditions, thereby confounding the diagnosis. Notably, BNP levels tend to be elevated in patients with medical history of heart failure and renal failure. For example, Chung et al. 2006 (supra) have shown that BNP performance for diagnosing AHF in patients presenting with dyspnea is significantly reduced in patients with a history of heart failure. In particular, about 40% of patients presenting with dyspnea not caused by AHF, who had a history of heart failure, displayed BNP values over 400 pg/mL, the AHF cut-off point used currently in the clinic. Consequently, the European Society of Cardiology (ESC) Guidelines 2008 also characterise BNP as a biomarker of heart failure in general rather than of acute heart failure.

In view of this, there exists a persistent need for additional and preferably specific biomarkers for AHF. Such novel AHF biomarkers may be comparable to or improved over previously existing markers, such as over BNP, in one or more of their characteristics, such as, for example, in their sensitivity and/or specificity, in their reliability in patients presenting with a symptom potentially indicative of AHF such as with dyspnea, in their reliability in patients with history of heart failure and other frequent co-morbidities of heart failure such renal failure, obesity, coronary artery disease etc. WO 2008/037720 e.g. presents a gene expression screening indicating but not verifying that reduced expression of the Quiescin Q6 gene in hearts of the hypertension rat model Ren-2 might be associated with an increased risk of the progression of heart hypertrophy towards congestive heart failure. However, WO 2008/037720 is entirely silent of any utility of Quiescin Q6 polypeptide, and particularly of increased levels thereof, as a biomarker for acute heart failure.

The present invention addresses the above needs in the art by identifying further biomarkers for AHF, and providing uses therefore.

SUMMARY OF THE INVENTION

Having conducted extensive experiments and tests, the inventors have revealed that the polypeptide Quiescin Q6 represents a newly realised biomarker particularly advantageous for predicting, diagnosing and/or prognosticating acute heart failure (AHF).

In particular, in a 3-centre, 200-subject study involving prospective collection of samples from subjects presenting with dyspnea upon emergency admission, as well as from chronic heart failure (CHF) patients and from matched healthy controls, the inventors have first identified and subsequently validated Quiescin Q6 as a biomarker displaying a significantly altered level in dyspneic patients having AHF, when compared to dyspneic patients not having AHF, CHF patients or healthy controls. In addition, the inventors have also realised that Quiescin Q6 may be a useful biomarker for monitoring the progression of AHF, i.e. by measuring the level of Quiescin Q6 in e.g. dyspneic patients upon admission (i.e., before treatment), during the treatment and upon discharge (i.e., following treatment).

The inventors have further shown that Quiescin Q6 can outperform BNP and NT-proBNP in a number of relevant respects:

For example, for discriminating between the dyspneic patients with and without AHF, the AUC value (area under the ROC curve; "ROC" stands for receiver operating characteristic) is higher for Quiescin Q6 than for each one of BNP and NT-proBNP. The AUC value is a combined measure of sensitivity and specificity and a higher AUC value (i.e., approaching 1) in general indicates an improved performance of the test.

Moreover, for discriminating between the patients with AHF and those with CHF, the AUC value for Quiescin Q6 is substantially higher than that for BNP and NT-proBNP. Hence, the Quiescin Q6 test is more reliably in patients with a history of heart failure.

In addition, as mentioned above, the BNP marker diagnosis has a troublesome "grey zone" between values of 100-400 pg/ml, in which no exact diagnosis of AHF can be established. Using the Quiescin Q6 marker level in said samples of the BNP "grey zone" resulted in a clear distinction between AHF and non-AHF-dyspnea patients (a median AUC of 0.91 for Quiescin Q6, compared to an AUC of 0.58 for BNP).

This overall diagnostic performance of Quiescin Q6 shows equivalent performance to BNP and NT-proBNP, the current gold standard biomarkers for diagnosing AHF in an acute dyspnea population. At a single ratio or concentration cut-off Quiescin Q6 reaches a diagnostic accuracy of 82% while BNP at its rule-out cut-off (100 pg/mL) has an accuracy of 73%. Combining Quiescin Q6 and BNP has a significant impact on the diagnostic accuracy, reaching a remarkable of 88% accuracy in the used dataset. Taken together, the inventors have identified and validated Quiescin Q6 as a further and improved biomarker for predicting, diagnosing and/or prognosticating AHF, in particular in patients with a history of heart failure, or suffering from other non-AHF-disorders causing dyspnea.

Remarkably, unlike the BNP levels, the Quiescin Q6 marker levels are not influenced by other disease parameters such as age, renal failure (based on creatinin levels), left ventricular ejection fraction, admission diagnosis, history of heart failure and coronary artery disease and COPD/asthma co-morbidities. No significant association of the Quiescin Q6 level to any of the listed parameters could be detected, implying that Quiescin Q6 levels are not influenced by any parameter other than an acute decompensation of the heart in the current dataset.

The Quiescin Q6 levels have been shown in the present invention to be independent of renal failure while BNP and NT-proBNP are clearly elevated in patients with increased creatinin levels. As renal failure is a frequent co-morbidity of heart failure, independence of the new Quiescin Q6 marker levels to creatinin levels is an important feature and will have a major impact on the diagnostic performance.

Measuring Quiescin Q6 levels in the AHF, dyspnea but non-AHF and stable CHF populations indicated that median Quiescin Q6 levels among patients with AHF were 1.5 fold higher than dyspneic patients without AHF. Strikingly, the levels of Quiescin Q6 in dyspnea but non-AHF patients are very much comparable to levels in stable CHF patients, while baseline levels for BNP are elevated in stable CHF patients.

Consequently, in an aspect the invention provides a method for predicting, diagnosing and/or prognosticating acute heart failure (AHF) in a subject, characterised in that the examination phase of the method comprises measuring the quantity of Quiescin Q6 in a sample from the subject. One understands that methods of prediction, diagnosis and/or prognosis of diseases or conditions generally comprise an examination phase in which data is collected from and/or about the subject.

Hence, a method for predicting, diagnosing and/or prognosticating AHF in a subject according to the present invention may comprise the following steps:
(i) measuring the quantity of Quiescin Q6 in a sample from the subject;
(ii) comparing the quantity of Quiescin Q6 measured in (i) with a reference value of the quantity of Quiescin Q6, said reference value representing a known prediction, diagnosis and/or prognosis of AHF;
(iii) finding a deviation or no deviation of the quantity of Quiescin Q6 measured in (i) from the reference value;
(iv) attributing said finding of deviation or no deviation to a particular prediction, diagnosis and/or prognosis of AHF in the subject.

Quiescin Q6 provides an improved or even substantially complete discrimination between AHF and other phenotypes, such as in particular CHF. Therefore, the inventors contemplate that Quiescin Q6 can also be beneficial for population screening setups to select subjects having or being at risk of having AHF. The use of BNP for such population screening is complicated especially by the confounding effect of heart history (e.g., CHF pathology) on the BNP readout, hence BNP fails for screening due to lack of specificity. Thus, in an embodiment, the present methods for predicting, diagnosing and/or prognosticating AHF in a subject may be employed for population screening (such as, e.g., screening in a general population or in a population stratified based on one or more criteria, e.g., age, gender, ancestry, occupation, presence or absence of risk factors of AHF, etc.).

As demonstrated in the experimental section, the inventors have shown that prediction or diagnosis of AHF or a poor prognosis of AHF can in particular be associated with an elevated level of Quiescin Q6. Hence, in an embodiment of the prediction, diagnosis and/or prognosis methods as taught herein, an elevated quantity of Quiescin Q6 in the sample from the subject compared to a reference value representing the prediction or diagnosis of no AHF or representing a good prognosis for AHF indicates that the subject has or is at risk of having AHF or indicates a poor prognosis for AHF in the subject.

The inventors have also observed and verified that methods using Quiescin Q6 as a biomarker, and particularly but without limitation the methods for discriminating between the dyspneic patients with and without AHF, can achieve a sensitivity of about 80% or more and/or a specificity of about 80% or more. Hence, in an embodiment of the prediction, diagnosis and/or prognosis methods as taught herein, the sensitivity and/or specificity (and preferably, the sensitivity and specificity) of the methods is at least 50%, at least 60%, at least 70% or at least 80%, e.g., ≥81%, ≥82%, ≥83%, ≥84%, ≥85%, ≥86%, or ≥87%, or ≥90% or ≥95% (symbol "≥" is synonymous with expressions "at least" or "equal to or more"), e.g., between 80% and 100%, or between 81% and 95%, or between 83% and 90%, or between 84% and 89%, or between 85% and 88%.

In a further embodiment, the prediction, diagnosis and/or prognosis methods as taught herein may be for discriminating between subjects having or being at risk of having AHF and subjects having or being at risk of having chronic heart failure (CHF).

In another embodiment of the prediction, diagnosis and/or prognosis methods as taught herein, the subject may present himself with one or more symptoms and/or signs potentially indicative of AHF. For example, in an embodiment the subject may present himself with dyspnea. Hence, in an embodiment the methods may be for discriminating between subjects presenting themselves with dyspnea due to AHF and subjects presenting themselves with dyspnea due to causes other than or unrelated to AHF (such as, e.g., due to COPD or pneumonia).

In a further embodiment of the prediction, diagnosis and/or prognosis methods as taught herein, the subject may have a medical history of heart failure, such as, for example AHF and/or CHF. As explained, methods involving Quiescin Q6 tend to be more reliable than methods using BNP or NT-proBNP for such subjects.

In a further embodiment of the prediction, diagnosis and/or prognosis methods as taught herein, the subject may have a renal failure. Methods involving Quiescin Q6 are shown herein to be more reliable than methods using BNP or NT-proBNP for such subjects.

In a further embodiment of the prediction, diagnosis and/or prognosis methods as taught herein, the subject may display one or more risk factors for AHF, such as, for example, a genetic predisposition or one or more developmental, environmental or behavioural risk factors, such as, e.g., insulin resistance (impaired blood glucose), truncal obesity, high serum low density lipoprotein (LDL) cholesterol levels, low serum high density lipoprotein (HDL) cholesterol levels, high serum triglyceride levels, and high blood pressure (hypertension), prior myocardial infarctus, and/or one or more co-morbidities, such as diabetes, coronary artery disease, asthma, COPD and/or chronic renal disease.

Hence, in various embodiments, the present methods for predicting, diagnosing and/or prognosticating AHF may be used in individuals who have not yet been diagnosed as having AHF (for example, preventative screening), or who have been diagnosed as having AHF or CHF, or who are suspected of having AHF or CHF (for example, display one or more symptoms characteristic of AHF or CHF), or who are at risk of developing AHF or CHF (for example, genetic predisposition; presence of one or more developmental, environmental or behavioural risk factors). The methods may also be used to detect various stages of progression or severity of AHF. The methods may also be used to detect response of AHF to prophylactic or therapeutic treatments or other interventions, e.g. by performing the methods at different time points during said prophylactic or therapeutic treatment or other intervention.

The invention further provides a method for monitoring a change in the prediction, diagnosis and/or prognosis of AHF in a subject, comprising:
  (i) applying the prediction, diagnosis and/or prognosis method as taught here above to the subject at one or more successive time points, whereby the prediction, diagnosis and/or prognosis of AHF in the subject is determined at said successive time points;
  (ii) comparing the prediction, diagnosis and/or prognosis of AHF in the subject at said successive time points as determined in (i); and
  (iii) finding the presence or absence of a change between the prediction, diagnosis and/or prognosis of AHF in the subject at said successive time points as determined in (i).

This aspect allows to monitoring the subject's condition over time. This can inter alia allow to predict the occurrence of an AHF event, or to monitor in said subject the disease progression, disease aggravation or alleviation, disease recurrence, response to treatment, response to other external or internal factors, conditions, or stressors, etc. Advantageously, the change in the prediction, diagnosis and/or prognosis of AHF in the subject may be monitored in the course of a medical treatment of said subject, preferably a medical treatment aimed at treating AHF. Such monitoring may be comprised, e.g., in decision making whether a patient (e.g., a dyspneic or AHF patient) may be discharged or needs further hospitalisation.

It shall be appreciated that in the present prediction, diagnosis and/or prognosis methods the measurement of Quiescin Q6 may also be combined with the assessment of one or more further biomarkers relevant for AHF.

Consequently, also disclosed herein are methods, wherein the examination phase of the methods further comprises measuring the presence or absence and/or quantity of one or more other biomarkers useful for predicting, diagnosing and/or prognosticating AHF in the sample from the subject.

Hence, disclosed is a method for predicting, diagnosing and/or prognosticating AHF in a subject comprising the steps:
  (i) measuring the quantity of Quiescin Q6 and the presence or absence and/or quantity of said one or more other biomarkers in the sample from the subject;
  (ii) using the measurements of (i) to establish a subject profile of the quantity of Quiescin Q6 and the presence or absence and/or quantity of said one or more other biomarkers;
  (iii) comparing said subject profile of (ii) to a reference profile of the quantity of Quiescin Q6 and the presence or absence and/or quantity of said one or more other biomarkers, said reference profile representing a known prediction, diagnosis and/or prognosis of AHF;
  (iv) finding a deviation or no deviation of the subject profile of (ii) from the reference profile;
  (v) attributing said finding of deviation or no deviation to a particular prediction, diagnosis and/or prognosis of AHF in the subject.

In an embodiment, said other biomarker useful for predicting, diagnosing and/or prognosticating AHF is chosen from the group consisting of B-type natriuretic peptide (BNP), pro-B-type natriuretic peptide (proBNP), amino terminal pro-B-type natriuretic peptide (NTproBNP), and fragments of any one thereof.

As indicated above, the present methods may employ reference values for the quantity of Quiescin Q6, which may be established according to known procedures previously employed for other biomarkers. Such reference values may be established either within (i.e., constituting a step of) or external to (i.e., not constituting a step of) the present methods. Accordingly, any one of the methods taught herein may comprise a step of establishing a reference value for the quantity of Quiescin Q6, said reference value representing either (a) a prediction or diagnosis of no AHF or a good prognosis for AHF, or (b) a prediction or diagnosis of AHF or a poor prognosis for AHF.

A further aspect provides a method for establishing a reference value for the quantity of Quiescin Q6, said reference value representing:

(a) a prediction or diagnosis of no AHF or a good prognosis for AHF, or
(b) a prediction or diagnosis of AHF or a poor prognosis for AHF, comprising:
(i) measuring the quantity of Quiescin Q6 in:
  (i a) one or more samples from one or more subjects not having AHF or not being at risk of having AHF or having a good prognosis for AHF, or
  (i b) one or more samples from one or more subjects having AHF or being at risk of having AHF or having a poor prognosis for AHF, and
(ii) storing the quantity of Quiescin Q6
  (ii a) as measured in (i a) as the reference value representing the prediction or diagnosis of no AHF or representing the good prognosis for AHF, or
  (ii b) as measured in (i b) as the reference value representing the prediction or diagnosis of AHF or representing the poor prognosis for AHF.

The present methods may otherwise employ reference profiles for the quantity of Quiescin Q6 and the presence or absence and/or quantity of one or more other biomarkers useful for predicting, diagnosing and/or prognosticating AHF, which may be established according to known procedures previously employed for other biomarkers. Such reference profiles may be established either within (i.e., constituting a step of) or external to (i.e., not constituting a step of) the present methods. Accordingly, the methods taught herein may comprise a step of establishing a reference profile for the quantity of Quiescin Q6 and the presence or absence and/or quantity of said one or more other biomarkers, said reference profile representing either (a) a prediction or diagnosis of no AHF or a good prognosis for AHF, or (b) a prediction or diagnosis of AHF or a poor prognosis for AHF.

A further aspect provides a method for establishing a reference profile for the quantity of Quiescin Q6 and the presence or absence and/or quantity of one or more other biomarkers useful for predicting, diagnosing and/or prognosticating AHF, said reference profile representing:
(a) a prediction or diagnosis of no AHF or a good prognosis for AHF, or
(b) a prediction or diagnosis of AHF or a poor prognosis for AHF, comprising:
(i) measuring the quantity of Quiescin Q6 and the presence or absence and/or quantity of said one or more other biomarkers in:
  (i a) one or more samples from one or more subjects not having AHF or not being at risk of having AHF or having a good prognosis for AHF; or
  (i b) one or more samples from one or more subjects having AHF or being at risk of having AHF or having a poor prognosis for AHF;
(ii)
  (ii a) using the measurements of (i a) to create a profile of the quantity of Quiescin Q6 and the presence or absence and/or quantity of said one or more other biomarkers; or
  (ii b) using the measurements of (i b) to create a profile of the quantity of Quiescin Q6 and the presence or absence and/or quantity of said one or more other biomarkers;
(iii)
  (iii a) storing the profile of (ii a) as the reference profile representing the prediction or diagnosis of no AHF or representing the good prognosis for AHF; or
  (iii b) storing the profile of (ii b) as the reference profile representing the prediction or diagnosis of AHF or representing the poor prognosis for AHF.

In an embodiment, said other biomarker useful for predicting, diagnosing and/or prognosticating AHF may be chosen from the group consisting of B-type natriuretic peptide (BNP), pro-B-type natriuretic peptide (proBNP), amino terminal pro-B-type natriuretic peptide (NTproBNP), and fragments of any one thereof.

The invention further provides a method for establishing a Quiescin Q6 base-line or reference value in a subject, comprising:
(i) measuring the quantity of Quiescin Q6 in the sample from the subject at different time points wherein the subject is not suffering from AHF, and
(ii) calculating the range or mean value of the subject, which is the Quiescin Q6 base-line or reference value for said subject.

In preferred embodiments of any one of above methods the subject may be human.

Dyspnea can be caused by AHF, but also is present in other patients due to causes other than or unrelated to AHF such as, COPD, pneumonia, atrial fibrillation, intoxication etc. The diagnostic methods according to the invention work particularly well in a patient population showing signs of dyspnea, enabling the specific diagnosis of AHF based on the Quiescin Q6 level. In a preferred embodiment of any one the above methods of the present invention, the subject thus forms part of a patient population showing signs of dyspnea or with a history of heart failure.

In the methods taught herein, the quantity of Quiescin Q6 and/or the presence or absence and/or quantity of the one or more other biomarkers may be measured by any suitable technique such as may be known in the art.

In an embodiment, the quantity of Quiescin Q6 and/or the presence or absence and/or quantity of the one or more other biomarkers may be measured using, respectively, a binding agent capable of specifically binding to Quiescin Q6 and/or to fragments thereof, and a binding agent capable of specifically binding to said one or more other biomarkers.

In an embodiment, the binding agent may be an antibody, aptamer, photoaptamer, protein, peptide, peptidomimetic or a small molecule.

In a further embodiment, the quantity of Quiescin Q6 and/or the presence or absence and/or quantity of the one or more other biomarkers is measured using an immunoassay technology, such as direct ELISA, indirect ELISA, sandwich ELISA, competitive ELISA, multiplex ELISA, radioimmunoassay (RIA) or ELISPOT technologies, or using a mass spectrometry analysis method or using a chromatography method, or using a combination of said methods.

Another aspect discloses a kit for predicting, diagnosing and/or prognosticating AHF in a subject, the kit comprising means for measuring the quantity of Quiescin Q6 in a sample from the subject.

An embodiment provides the kit for predicting, diagnosing and/or prognosticating AHF in the subject, the kit comprising:
(i) means for measuring the quantity of Quiescin Q6 in the sample from the subject; and
(ii) a reference value of the quantity of Quiescin Q6 or means for establishing said reference value, wherein said reference value represents a known prediction, diagnosis and/or prognosis of AHF.

The kit thus allows one to: measure the quantity of Quiescin Q6 in the sample from the subject by means (i);

compare the quantity of Quiescin Q6 measured by means (i) with the reference value of (ii) or established by means (ii); find a deviation or no deviation of the quantity of Quiescin Q6 measured by means (i) from the reference value of (ii); and consequently attribute said finding of deviation or no deviation to a particular prediction, diagnosis and/or prognosis of AHF in the subject.

A further embodiment provides a kit for predicting, diagnosing and/or prognosticating AHF in a subject, the kit comprising means for measuring the quantity of Quiescin Q6 in a sample from the subject and means for measuring the presence or absence and/or quantity of one or more other biomarkers useful for predicting, diagnosing and/or prognosticating AHF in the sample from the subject.

An embodiment provides the kit for predicting, diagnosing and/or prognosticating AHF in the subject, the kit comprising:
  (i) means for measuring the quantity of Quiescin Q6 in the sample from the subject;
  (ii) means for measuring the presence or absence and/or quantity of the one or more other biomarkers useful for predicting, diagnosing and/or prognosticating AHF in the sample from the subject;
  (iii) optionally, means for establishing a subject profile of the quantity of Quiescin Q6 and the presence or absence and/or quantity of said one or more other biomarkers; and
  (iv) a reference profile of the quantity of Quiescin Q6 and the presence or absence and/or quantity of said one or more other biomarkers, or means for establishing said reference profile, said reference profile representing a known prediction, diagnosis and/or prognosis of AHF.

Such kit thus allows one to: measure the quantity of Quiescin Q6 and the presence or absence and/or quantity of said one or more other biomarkers in the sample from the subject by respectively means (i) and (ii); establish (e.g., using means included in the kit or using suitable external means) a subject profile of the quantity of Quiescin Q6 and the presence or absence and/or quantity of said one or more other biomarkers based on said measurements; compare the subject profile with the reference profile of (iv) or established by means (iv); find a deviation or no deviation of said subject profile from said reference profile; and consequently attribute said finding of deviation or no deviation to a particular prediction, diagnosis and/or prognosis of AHF in the subject.

In an embodiment of the above kits, said other biomarker useful for predicting, diagnosing and/or prognosticating AHF may be chosen from the group consisting of B-type natriuretic peptide (BNP), pro-B-type natriuretic peptide (proBNP), amino terminal pro-B-type natriuretic peptide (NTproBNP), and fragments of any one thereof.

In a further embodiment of the above kits, the means for measuring the quantity of Quiescin Q6 and/or the presence or absence and/or quantity of the one or more other biomarkers may comprise, respectively, one or more binding agents capable of specifically binding to Quiescin Q6 and/or to fragments thereof, and one or more binding agents capable of specifically binding to said one or more other biomarkers.

In an embodiment, any one of said one or more binding agents may be an antibody, aptamer, photoaptamer, protein, peptide, peptidomimetic or a small molecule.

In an embodiment, any one of said one or more binding agents may be advantageously immobilised on a solid phase or support.

In a further embodiment of the above kits, the means for measuring the quantity of Quiescin Q6 and/or the presence or absence and/or quantity of the one or more other biomarkers may employ an immunoassay technology, such as direct ELISA, indirect ELISA, sandwich ELISA, competitive ELISA, multiplex ELISA, radioimmunoassay (RIA) or ELISPOT technologies, or may employ a mass spectrometry analysis technology or may employ a chromatography technology, or may employ a combination of said technologies.

An embodiment thus discloses a kit for predicting, diagnosing and/or prognosticating AHF comprising:
  (a) one or more binding agents capable of specifically binding to Quiescin Q6 and/or to fragments thereof;
  (b) preferably, a known quantity or concentration of Quiescin Q6 and/or a fragment thereof (e.g., for use as controls, standards and/or calibrators);
  (c) preferably, a reference value of the quantity of Quiescin Q6, or means for establishing said reference value.

Said components under (a) and/or (c) may be suitably labelled as taught elsewhere in this specification.

Another embodiment discloses a kit for predicting, diagnosing and/or prognosticating AHF comprising:
  (a) one or more binding agents capable of specifically binding to Quiescin Q6 and/or to fragments thereof;
  (b) one or more binding agents capable of specifically binding to one or more other biomarkers useful for predicting, diagnosing and/or prognosticating AHF, preferably wherein said other biomarkers are chosen from the group consisting of BNP, proBNP, NTproBNP and fragments of any one thereof;
  (c) preferably, a known quantity or concentration of Quiescin Q6 and/or a fragment thereof and a known quantity or concentration of said one or more other biomarkers (e.g., for use as controls, standards and/or calibrators);
  (d) preferably, a reference profiles of the quantity of Quiescin Q6 and the presence or absence and/or quantity of said one or more other biomarkers, or means for establishing said reference profiles.

Said components under (a), (b) and/or (c) may be suitably labelled as taught elsewhere in this specification.

Also disclosed are reagents and tools useful for measuring Quiescin Q6 and optionally the one or more other AHF-related biomarkers concerned herein.

For example, a further aspect relates to a protein, polypeptide or peptide array or microarray comprising
  (a) Quiescin Q6 and/or a fragment thereof, preferably a known quantity or concentration of said Quiescin Q6 and/or fragment thereof; and
  (b) optionally and preferably, one or more other biomarkers useful for predicting, diagnosing and/or prognosticating AHF, preferably a known quantity or concentration of said one or more other biomarkers, and preferably wherein said other biomarkers are chosen from the group consisting of BNP, proBNP, NTproBNP and fragments of any one thereof.

Another aspect relates to a binding agent array or microarray comprising:
  (a) one or more binding agents capable of specifically binding to Quiescin Q6 and/or to fragments thereof, preferably a known quantity or concentration of said binding agents; and
  (b) optionally and preferably, one or more binding agents capable of specifically binding to one or more other biomarkers useful for predicting, diagnosing and/or prognosticating AHF, preferably a known quantity or concentration of said binding agents, and preferably wherein said other biomarkers are chosen from the group consisting of BNP, proBNP, NTproBNP and fragments of any one thereof.

Also disclosed are kits as taught here above configured as portable devices, such as, for example, bed-side devices, for use at home or in clinical settings.

A related aspect thus provides a portable testing device capable of measuring the quantity of Quiescin Q6 in a sample from a subject comprising:
(i) means for obtaining a sample from the subject,
(ii) means for measuring the quantity of Quiescin Q6 in said sample, and
(iii) means for visualising the quantity of Quiescin Q6 measured in the sample.

In an embodiment, the means of parts (ii) and (iii) may be the same, thus providing a portable testing device capable of measuring the quantity of Quiescin Q6 in a sample from a subject comprising (i) means for obtaining a sample from the subject; and (ii) means for measuring the quantity of Quiescin Q6 in said sample and visualising the quantity of Quiescin Q6 measured in the sample.

In an embodiment, said visualising means is capable of indicating whether the quantity of Quiescin Q6 in the sample is above or below a certain threshold level and/or whether the quantity of Quiescin Q6 in the sample deviates or not from a reference value of the quantity of Quiescin Q6, said reference value representing a known prediction, diagnosis and/or prognosis of AHF (as taught elsewhere in this application). Hence, in an embodiment, the portable testing device may suitably also comprise said reference value or means for establishing said reference value.

In an embodiment, the threshold level is chosen such that the quantity of Quiescin Q6 in the sample above said threshold level indicates that the subject has or is at risk of having AHF or indicates a poor prognosis for AHF in the subject, and the quantity of Quiescin Q6 in the sample below said threshold level indicates that the subject does not have or is not at risk of having AHF or indicates a good prognosis for AHF in the subject.

In an embodiment, the portable testing device comprises a reference value representing the prediction or diagnosis of no AHF or representing a good prognosis for AHF, or comprises means for establishing said reference value, and an elevated quantity of Quiescin Q6 in the sample from the subject compared to said reference value indicates that the subject has or is at risk of having AHF or indicates a poor prognosis for AHF in the subject.

In another embodiment, the portable testing device comprises a reference value representing the prediction or diagnosis of AHF or representing a poor prognosis for AHF, or comprises means for establishing said reference value, and a comparable quantity of Quiescin Q6 in the sample from the subject compared to said reference value indicates that the subject has or is at risk of having AHF or indicates a poor prognosis for AHF in the subject.

In a further embodiment, the measuring (and optionally visualisation) means of the portable testing device may comprise a solid support having a proximal and distal end, comprising:
a sample application zone in the vicinity of the proximal end;
a reaction zone distal to the sample application zone; and
a detection zone distal to the reaction zone;
optionally control standards comprising Quiescin Q6 protein or peptide fragments, whereby said support has a capillary property that directs a flow of fluid sample applied in the application zone in a direction from the proximal end to the distal end, and
optionally comprising a fluid source improving the capillary flow of a more viscous sample.

In an embodiment, the reaction zone may comprise one or more bands of a Quiescin Q6-specific binding molecules conjugated to a detection agent, which Quiescin Q6 specific binding molecule conjugate is disposed on the solid support such that it can migrate with the capillary flow of fluid; and wherein the detection zone comprises one or more capture bands comprising a population of Quiescin Q6 specific molecule immobilised on the solid support. In an embodiment, the reaction zone may additionally comprise one or more bands of capture Quiescin Q6-specific binding molecules in an amount sufficient to prevent a threshold quantity of Quiescin Q6 specific binding molecule conjugates to migrate to the detection zone. In an alternative embodiment, said device additionally comprises means for comparing the amount of captured Quiescin Q6 specific binding molecule conjugate with a threshold value.

These and further aspects and preferred embodiments are described in the following sections and in the appended claims.

BRIEF DESCRIPTION OF FIGURES

FIGS. 1A and 1B illustrate sequences of isoforms 1 (A) and 2 (B) of Quiescin Q6.

FIG. 2 illustrates the differences between isoforms 1 and 2 of Quiescin Q6. The C-terminal portion missing in isoform 2 is indicated in small letters. Also indicated are MASStermind discovered peptides (pept10012—bold, underlined with full line: SEQ ID NO: 7; pept10014—bold, underlined with pointed line: SEQ ID NO: 8; pept10055—bold, underlined with dashed line: SEQ ID NO: 9) and the selected MASSterclass quantified peptide (pept110—bold, double underlined: SEQ ID NO: 10). MASStermind and MASSterclass peptides can quantify both isoforms of Quiescin Q6.

FIGS. 3A-3D illustrate sequences of preproBNP and peptides derived therefrom. FIG. 3A illustrates Natriuretic peptide precursor B preproprotein, NP_002512. FIG. 3B illustrates proBNP from NP_002512. FIG. 3C illustrates NTproBNP from NP_002512. FIG. 3D illustrates BNP from NP_002512.

FIGS. 7A and 7B illustrate that Quiescin Q6 shows better performance than B-type natriuretic peptides in discriminating AHF from dyspneic non-acute heart failure patients. FIG. 7A shows receiver operating characteristic curve of BNP compared to Quiescin Q6 and NT-proBNP compared to Quiescin Q6 respectively for diagnosis of heart failure cause of dyspnea in the ED. Calculated area under the curve (AUC) and 95% confidence intervals are given in the table. FIG. 7B shows accuracy plot for BNP and Quiescin Q6 with calculated sensitivity and specificity at different cut-off concentrations for diagnosis of AHF in dyspneic patients in the ED.

FIG. 12 illustrates that Quiescin Q6 levels are independent of renal failure. The boxplots show the levels of NT-proBNP (top) and Quiescin Q6 (bottom) in patients diagnosed with acute decompensated heart failure (AHF) and patients with stable chronic heart failure (CHF) grouped according to their creatinin levels, either normal (<150 umol/L) or increased (>150 umol/L).

FIG. 14: Plan (A) and side view (B) of a test strip according to the invention.

FIG. 15: Plan view of a test cartridge according to the invention.

FIG. 16 A-B shows a side view and a top view, respectively, of a reagent strip according to the invention comprising several test pads.

DETAILED DESCRIPTION OF THE INVENTION

Figure 4:
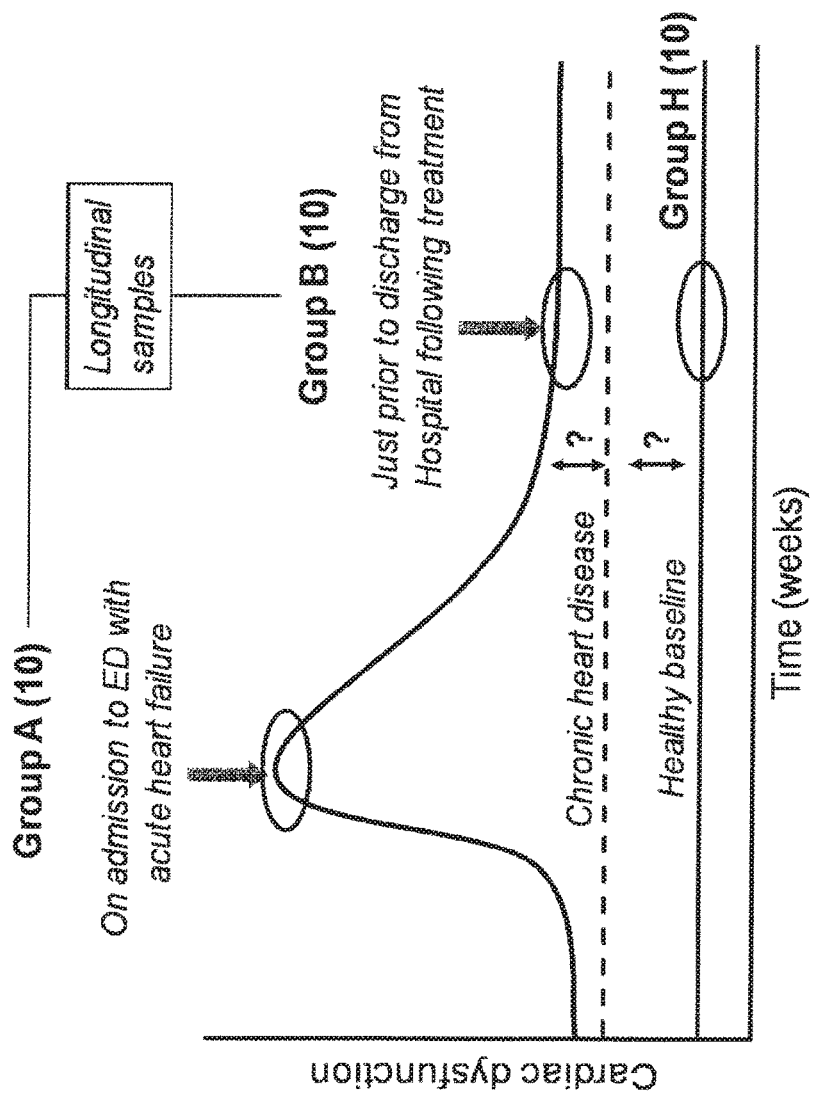
FIG. 4 provides a schematic overview of the acute heart failure discovery experimental set-up. Protein profiles of populations A (AHF on admission to emergency department (ED)), B (same patients at discharge) and H (healthy controls) were compared using MASStermind. Quantitation in populations C (chronic heart failure) and D (Dyspnea patients without HF on admission) was done in a targeted way using MASSterclass.

As used herein, the singular forms "a", "an", and "the" include both singular and plural referents unless the context clearly dictates otherwise.

The terms "comprising", "comprises" and "comprised of" as used herein are synonymous with "including", "includes" or "containing", "contains", and are inclusive or open-ended and do not exclude additional, non-recited members, elements or method steps. Obviously, the term comprises also encompasses the closed wording "consisting of" as one of its embodiments.

The recitation of numerical ranges by endpoints includes all numbers and fractions subsumed within the respective ranges, as well as the recited endpoints.

The term "about" as used herein when referring to a measurable value such as a parameter, an amount, a temporal duration, and the like, is meant to encompass variations of and from the specified value, in particular variations of +/−10% or less, preferably +/−5% or less, more preferably +/−1% or less, and still more preferably +/−0.1% or less of and from the specified value, insofar such variations are appropriate to perform in the disclosed invention. It is to be understood that the value to which the modifier "about" refers is itself also specifically, and preferably, disclosed.

All documents cited in the present specification are hereby incorporated by reference in their entirety.

Unless otherwise specified, all terms used in disclosing the invention, including technical and scientific terms, have the meaning as commonly understood by one of ordinary skill in the art to which this invention belongs. By means of further guidance, term definitions may be included to better appreciate the teaching of the present invention.

The present invention derives from the highly innovative realisation of the inventors that Quiescin Q6 is a valuable biomarker particularly for acute heart failure (AHF). The term "biomarker" is widespread in the art and may broadly denote a biological molecule and/or a detectable portion thereof whose qualitative and/or quantitative evaluation in a subject is predictive or informative (e.g., predictive, diagnostic and/or prognostic) with respect to one or more aspects of the subject's phenotype and/or genotype, such as, for example, with respect to the status of the subject as to a given disease or condition.

The terms "heart failure", "acute heart failure" and "chronic heart failure" as used herein carry their respective art-established meanings. By means of further guidance, the term "heart failure" as used herein broadly refers to pathological conditions characterised by an impaired diastolic or systolic blood flow rate and thus insufficient blood flow from the ventricle to peripheral organs.

"Acute heart failure" or also termed "acute decompensated heart failure" may be defined as the rapid onset of symptoms and signs secondary to abnormal cardiac function, resulting in the need for urgent therapy. AHF can present itself acute de novo (new onset of acute heart failure in a patient without previously known cardiac dysfunction) or as acute decompensation of CHF.

The cardiac dysfunction may be related to systolic or diastolic dysfunction, to abnormalities in cardiac rhythm, or to preload and afterload mismatch. It is often life threatening and requires urgent treatment. According to established classification, AHF includes several distinct clinical conditions of presenting patients: (I) acute decompensated congestive heart failure, (II) AHF with hypertension/hypertensive crisis, (III) AHF with pulmonary oedema, (IVa) cardiogenic shock/low output syndrome, (IVb) severe cardiogenic shock, (V) high output failure, and (VI) right-sided acute heart failure. For detailed clinical description, classification and diagnosis of AHF, and for summary of further AHF classification systems including the Killip classification, the Forrester classification and the 'clinical severity' classification, refer inter alia to Nieminen et al. 2005 ("Executive summary of the guidelines on the diagnosis and treatment of acute heart failure: the Task Force on Acute Heart Failure of the European Society of Cardiology". Eur Heart J 26: 384-416) and references therein.

The terms "chronic heart failure" (CHF) or "congestive heart failure" may generally refer to a case of heart failure that progresses so slowly that various compensatory mechanisms work to bring the disease into equilibrium. Common clinical symptoms of CHF include inter alia any one or more of breathlessness, diminishing exercise capacity, fatigue, lethargy and peripheral oedema. Other less common symptoms include any one or more of palpitations, memory or sleep disturbance and confusion, and usually co-occur with one or more of the above recited common symptoms.

In studies such as the present one, CHF population may differ from the AHF population in that CHF patients do not have an acute decompensation and hence do not represent themselves to the ED at the time the clinical sample used in such a study or research is taken. Chronic heart failure patients may, however, easily decompensate leading to "acute heart failure".

In studies such as the present one, a population of dyspneic patients without heart failure may comprise for example patients who present themselves to the ED with similar symptoms as AHF population but where the cause of dyspnea is unrelated to acute decompensated heart failure. Typical examples are COPD or pneumonia patients. Such patients may or may not have underlying heart failure history, which may particularly complicate the final diagnosis using conventional diagnostic means.

The terms "predicting" or "prediction", "diagnosing" or "diagnosis" and "prognosticating" or "prognosis" are commonplace and well-understood in medical and clinical practice. By means of further explanation and without limitation, "predicting" or "prediction" generally refer to an advance declaration, indication or foretelling of a disease or condition in a subject not (yet) having said disease or condition. For example, a prediction of a disease or condition in a subject may indicate a probability, chance or risk that the subject will develop said disease or condition, for example within a certain time period or by a certain age. Said probability, chance or risk may be indicated inter alia as an absolute value, range or statistics, or may be indicated relative to a suitable control subject or subject population (such as, e.g., relative to a general, normal or healthy subject or subject population). Hence, the probability, chance or risk that a subject will develop a disease or condition may be advantageously indicated as increased or decreased, or as fold-increased or fold-decreased relative to a suitable control subject or subject population.

As used herein, the term "prediction of AHF" in a subject may also particularly mean that the subject has a 'positive' prediction of AHF, i.e., that the subject is at risk of having AHF (e.g., the risk is significantly increased vis-à-vis a control subject or subject population). The term "prediction of no AHF" in a subject may particularly mean that the subject has a 'negative' prediction of AHF, i.e., that the subject's risk of having AHF is not significantly increased vis-à-vis a control subject or subject population.

The terms "diagnosing" or "diagnosis" generally refer to the process or act of recognising, deciding on or concluding on a disease or condition in a subject on the basis of symptoms and signs and/or from results of various diagnostic procedures (such as, for example, from knowing the presence, absence and/or quantity of one or more biomarkers characteristic of the diagnosed disease or condition).

As used herein, "diagnosis of AHF" in a subject may particularly mean that the subject has AHF, hence, is diagnosed as having AHF. "Diagnosis of no AHF" in a subject may particularly mean that the subject does not have AHF, hence, is diagnosed as not having AHF. A subject may be diagnosed as taught herein as not having AHF despite displaying one or more conventional symptoms or signs reminiscent of AHF.

The terms "prognosticating" or "prognosis" generally refer to an anticipation on the progression of a disease or condition and the prospect (e.g., the probability, duration, and/or extent) of recovery.

A good prognosis of AHF may generally encompass anticipation of a satisfactory partial or complete recovery from AHF, preferably within an acceptable time period. A good prognosis of AHF may more commonly encompass anticipation of not further worsening or aggravating of the heart failure condition, preferably within a given time period.

A poor prognosis of AHF may generally encompass anticipation of a substandard recovery and/or unsatisfactorily slow recovery, or to substantially no recovery or even further worsening of AHF.

The various aspects and embodiments taught herein may rely on measuring the quantity of Quiescin Q6, and optionally measuring the presence or absence and/or quantity of one or more other relevant biomarkers, such as preferably BNP, proBNP, NTproBNP and/or fragments of any one thereof, in a sample from a subject.

The term "subject" or "patient" as used herein typically denotes humans, but may also encompass reference to non-human animals, preferably warm-blooded animals, more preferably mammals, such as, e.g., non-human primates, rodents, canines, felines, equines, ovines, porcines, and the like.

The terms "sample" or "biological sample" as used herein include any biological specimen obtained from a subject. Samples may include, without limitation, whole blood, plasma, serum, red blood cells, white blood cells (e.g., peripheral blood mononuclear cells), saliva, urine, stool (i.e., faeces), tears, sweat, sebum, nipple aspirate, ductal lavage, tumour exudates, synovial fluid, cerebrospinal fluid, lymph, fine needle aspirate, amniotic fluid, any other bodily fluid, cell lysates, cellular secretion products, inflammation fluid, semen and vaginal secretions. Preferred samples may include ones comprising Quiescin Q6 in detectable quantities. In preferred embodiments, the sample may be whole blood or a fractional component thereof such as, e.g., plasma, serum, or a cell pellet. Preferably the sample is readily obtainable by minimally invasive methods. Samples may also include tissue samples and biopsies, tissue homogenates and the like. In a preferred embodiment, the sample is a blood plasma sample. The term "plasma" defines the colorless watery fluid of the blood that contains no cells, but in which the blood cells (erythrocytes, leukocytes, thrombocytes, etc.) are suspended, containing nutrients, sugars, proteins, minerals, enzymes, etc.

A molecule or analyte such as a protein, polypeptide or peptide, or a group of two or more molecules or analytes such as two or more proteins, polypeptides or peptides, is "measured" in a sample when the presence or absence and/or quantity of said molecule or analyte or of said group of molecules or analytes is detected or determined in the sample, preferably substantially to the exclusion of other molecules and analytes.

The terms "quantity", "amount" and "level" are synonymous and generally well-understood in the art. The terms as used herein may particularly refer to an absolute quantification of a molecule or an analyte in a sample, or to a relative quantification of a molecule or analyte in a sample, i.e., relative to another value such as relative to a reference value as taught herein, or to a range of values indicating a base-line expression of the biomarker. These values or ranges can be obtained from a single patient or from a group of patients.

An absolute quantity of a molecule or analyte in a sample may be advantageously expressed as weight or as molar amount, or more commonly as a concentration, e.g., weight per volume or mol per volume.

A relative quantity of a molecule or analyte in a sample may be advantageously expressed as an increase or decrease or as a fold-increase or fold-decrease relative to said another value, such as relative to a reference value as taught herein. Performing a relative comparison between first and second parameters (e.g., first and second quantities) may but need not require to first determine the absolute values of said first and second parameters. For example, a measurement method can produce quantifiable readouts (such as, e.g., signal intensities) for said first and second parameters, wherein said readouts are a function of the value of said parameters, and wherein said readouts can be directly compared to produce a relative value for the first parameter vs. the second parameter, without the actual need to first convert the readouts to absolute values of the respective parameters.

As used herein, the terms "Quiescin Q6" and "Sulfhydryl oxidase 1" are synonymous and refer to proteins and polypeptides commonly known under these designations in the art.

The terms encompass such proteins and polypeptides of any organism where found, and particularly of animals, preferably vertebrates, more preferably mammals, including humans and non-human mammals, even more preferably of humans.

The terms particularly encompass such proteins and polypeptides with a native sequence, i.e., ones of which the primary sequence is the same as that of Quiescin Q6 found in or derived from nature. A skilled person understands that native sequences of Quiescin Q6 may differ between different species due to genetic divergence between such species. Moreover, the native sequences of Quiescin Q6 may differ between or within different individuals of the same species due to normal genetic diversity (variation) within a given species. Also, the native sequences of Quiescin Q6 may differ between or even within different individuals of the same species due to post-transcriptional or post-translational modifications. Accordingly, all Quiescin Q6 sequences found in or derived from nature are considered "native".

The terms encompass Quiescin Q6 proteins and polypeptides when forming a part of a living organism, organ, tissue or cell, when forming a part of a biological sample, as well as when at least partly isolated from such sources. The terms also encompass proteins and polypeptides when produced by recombinant or synthetic means.

Exemplary Quiescin Q6 includes, without limitation, human Quiescin Q6 having primary amino acid sequence as annotated under Uniprot/Swissprot accession number O00391 (entry version 69 revised on Jan. 20, 2009; sequence version 3 created on Jun. 1, 2001), including isoform 1 (acc. no. O00391-1) and isoform 2 (O00391-2) generated due to alternative splicing. The sequence of said isoforms 1 and 2 of Quiescin Q6 is shown in FIG. 1A (SEQ ID NO: 1) and FIG. 1B (SEQ ID NO: 2), respectively. FIG. 2 illustrates the differences in the C-terminal region between said isoforms 1 and 2. A skilled person can also appreciate that said sequences are of precursor of Quiescin Q6 and may include parts which are processed away from mature Quiescin Q6. For example, with reference to the isoform 1 sequence, the Uniprot/Swissprot entry specifies a signal peptide composed of amino acids 1-29. Exemplary human Quiescin Q6 has been also described inter alia by Coppock et al. 1998 (Genomics 54: 460-468).

The reference herein to Quiescin Q6 may also encompass fragments of Quiescin Q6. Hence, the reference herein to measuring Quiescin Q6, or to measuring the quantity of Quiescin Q6, may encompass measuring the Quiescin Q6 protein or polypeptide (such as, e.g., measuring the mature isoform 1 and/or isoform 2 of Quiescin Q6) and/or measuring one or more fragments of Quiescin Q6. For example, Quiescin Q6 and/or one or more fragments thereof may be measured collectively, such that the measured quantity corresponds to the sum amounts of the collectively measured species. In another example, Quiescin Q6 and/or one or more fragments thereof may be measured each individually.

In preferred embodiments of the methods, kits and devices of the present invention, the Quiescin Q6 protein detection is done in a plasma sample, implying that the circulating Quiescin Q6 protein is detected, regardless of whether or not this circulating form corresponds to a soluble form or to a degradation product of isoforms 1 or 2 of Quiescin Q6. In a preferred embodiment, the Quiescin Q6 protein or fragment that is detected is not membrane or cell-bound. The term "plasma" defines the colorless watery fluid of the blood that contains no cells, but in which the blood cells (erythrocytes, leukocytes, thrombocytes, etc.) are suspended, containing nutrients, sugars, proteins, minerals, enzymes, etc.

As used herein, the terms "pro-B-type natriuretic peptide" (also abbreviated as "proBNP") and "amino terminal pro-B-type natriuretic peptide" (also abbreviated as "NTproBNP") and "B-type natriuretic peptide" (also abbreviated as "BNP") refer to peptides commonly known under these designations in the art. As further explanation and without limitation, in vivo proBNP, NTproBNP and BNP derive from natriuretic peptide precursor B preproprotein (preproBNP). In particular, proBNP peptide corresponds to the portion of preproBNP after removal of the N-terminal secretion signal (leader) sequence from preproBNP. NTproBNP corresponds to the N-terminal portion and BNP corresponds to the C-terminal portion of the proBNP peptide subsequent to cleavage of the latter C-terminally adjacent to amino acid 76 of proBNP.

The terms encompass such peptides from any organism where found, and particularly from animals, preferably vertebrates, more preferably mammals, including humans and non-human mammals, even more preferably from humans.

The designations proBNP, NTproBNP and BNP as used herein particularly refer to such peptides with a native sequence, i.e., peptides of which the primary sequence is the same as that of respectively proBNP, NTproBNP or BNP found in or derived from nature. A skilled person understands that native sequences of proBNP, NTproBNP or BNP may differ between different species due to genetic divergence between such species. Moreover, the native sequences of proBNP, NTproBNP or BNP may differ between or even within different individuals of the same species due to normal genetic diversity (variation) within a given species. Also, the native sequences of proBNP, NTproBNP or BNP may differ between or even within different individuals of the same species due to post-transcriptional or post-translational modifications. Accordingly, all proBNP, NTproBNP or BNP sequences found in or derived from nature are considered "native".

The designations proBNP, NTproBNP or BNP as used herein encompass the respective peptides when forming a part of a living organism, organ, tissue or cell, when forming a part of a biological sample, as well as when at least partly isolated from such sources. The terms also encompass the respective peptides when produced by recombinant or synthetic means.

Exemplary human proBNP peptide includes without limitation the peptide from amino acid position 27 to position 134 of the natriuretic peptide precursor B preproprotein sequence as annotated under the NIH Entrez Protein accession number NP_002512 (version NP_002512.1 revised Jan. 25, 2009).

The sequence of NP_002512 is shown in FIG. 3A (SEQ ID NO: 3) and the exemplary sequence of proBNP from NP_002512 is shown in FIG. 3B (SEQ ID NO: 4). Exemplary human NTproBNP peptide includes without limitation the peptide from amino acid position 27 to position 102 of the natriuretic peptide precursor B preproprotein sequence as annotated under said NIH Entrez Protein accession number NP_002512. The exemplary sequence of NTproBNP from NP_002512 is shown in FIG. 3C (SEQ ID NO: 5). Exemplary human BNP peptide includes without limitation the peptide from amino acid position 103 to position 134 of the natriuretic peptide precursor B preproprotein sequence as annotated under said NIH Entrez Protein accession number NP_002512. The exemplary sequence of BNP from NP_002512 is shown in FIG. 3D (SEQ ID NO: 6). See also Sudoh et al. 1989 (Biochem Biophys Res Commun 159: 1427-1434) for further exemplification of human preproBNP-derived peptides, including proBNP, NTproBNP and BNP. See also Maisel et al. 2008 (Eur J Heart Fail 10(9): 824-39) and Miller et al. 2007 (Biomarkers Med 1(4): 503-512) on using natriuretic peptide levels in clinical practice.

The reference herein to proBNP, NTproBNP and/or BNP may also encompass fragments of any one of proBNP, NTproBNP and/or BNP. Hence, the reference herein to measuring the presence or absence and/or quantity of proBNP, NTproBNP and/or BNP, may encompass measuring the proBNP, NTproBNP and/or BNP peptides and/or measuring one or more fragments of any one of the proBNP, NTproBNP and/or BNP peptides. For example, the proBNP, NTproBNP and/or BNP peptides and/or one or more fragments of any one thereof may be measured collectively, such that the measured quantity corresponds to the sum amount of the collectively measured species. In another example, the proBNP, NTproBNP and/or BNP peptides and/or one or more fragments of any one thereof may be measured each individually.

Further, unless otherwise apparent from the context, reference herein to any protein, polypeptide or peptide (such as, e.g., Quiescin Q6, proBNP, NTproBNP or BNP) and fragments thereof may generally also encompass modified forms of said protein, polypeptide or peptide and fragments such as bearing post-expression modifications including, for example, phosphorylation, glycosylation, lipidation, methylation, cysteinylation, sulphonation, glutathionylation, acetylation, oxidation of methionine to methionine sulphoxide or methionine sulphone, and the like.

In an embodiment, Quiescin Q6 and fragments thereof, or proBNP, NTproBNP, BNP and fragments thereof may be human, i.e., their primary sequence may be the same as a corresponding primary sequence of or present in a naturally occurring human Quiescin Q6 and fragments thereof, or proBNP, NTproBNP, BNP and fragments thereof. Hence, the qualifier "human" in this connection relates to the primary sequence of the respective proteins, polypeptides, peptides or fragments, rather than to their origin or source. For example, such proteins, polypeptides, peptides or fragments may be present in or isolated from samples of human subjects or may be obtained by other means (e.g., by recombinant expression, cell-free translation or non-biological peptide synthesis).

The term "fragment" of a protein, polypeptide or peptide generally refers to N-terminally and/or C-terminally deleted or truncated forms of said protein, polypeptide or peptide. The term encompasses fragments arising by any mechanism, such as, without limitation, by alternative translation, exo- and/or endo-proteolysis and/or degradation of said protein or polypeptide, such as, for example, in vivo or in vitro, such as, for example, by physical, chemical and/or enzymatic proteolysis. Without limitation, a fragment of a protein, polypeptide or peptide may represent at least about 5%, or at least about 10%, e.g., ≥20%, ≥30% or ≥40%, such as ≥50%, e.g., ≥60%, ≥70% or ≥80%, or even ≥90% or ≥95% of the amino acid sequence of said protein, polypeptide or peptide.

For example, a fragment of Quiescin Q6 may include a sequence of ≥5 consecutive amino acids, or ≥10 consecutive amino acids, or ≥20 consecutive amino acids, or ≥30 consecutive amino acids, e.g., ≥40 consecutive amino acids, such as for example ≥50 consecutive amino acids, e.g., ≥60, ≥70, ≥80, ≥90, ≥100, ≥200, ≥300, ≥400, ≥500 or ≥600 consecutive amino acids of Quiescin Q6.

In an embodiment, a fragment of Quiescin Q6 may be N-terminally and/or C-terminally truncated by between 1 and about 20 amino acids, such as, e.g., by between 1 and about 15 amino acids, or by between 1 and about 10 amino acids, or by between 1 and about 5 amino acids, compared to mature, full-length Quiescin Q6 (e.g., isoforms 1 or 2).

In an embodiment, a fragment of proBNP, NTproBNP or BNP may be N-terminally and/or C-terminally truncated by between 1 and about 20 amino acids, such as, e.g., by between 1 and about 15 amino acids, or by between 1 and about 10 amino acids, or by between 1 and about 5 amino acids, compared to proBNP, NTproBNP or BNP. By means of example, proBNP, NTproBNP and BNP fragments useful as biomarkers are disclosed in WO 2004/094460.

In an embodiment, fragments of a given protein, polypeptide or peptide may be achieved by in vitro proteolysis of said protein, polypeptide or peptide to obtain advantageously detectable peptide(s) from a sample.

For example, such proteolysis may be effected by suitable physical, chemical and/or enzymatic agents, e.g., proteinases, preferably endoproteinases, i.e., protease cleaving internally within a protein, polypeptide or peptide chain. A non-limiting list of suitable endoproteinases includes serine proteinases (EC 3.4.21), threonine proteinases (EC 3.4.25), cysteine proteinases (EC 3.4.22), aspartic acid proteinases (EC 3.4.23), metalloproteinases (EC 3.4.24) and glutamic acid proteinases.

Exemplary non-limiting endoproteinases include trypsin, chymotrypsin, elastase, *Lysobacter enzymogenes* endoproteinase Lys-C, *Staphylococcus aureus* endoproteinase Glu-C (endopeptidase V8) or *Clostridium histolyticum* endoproteinase Arg-C (clostripain). Further known or yet to be identified enzymes may be used; a skilled person can choose suitable protease(s) on the basis of their cleavage specificity and frequency to achieve desired peptide forms.

Preferably, the proteolysis may be effected by endopeptidases of the trypsin type (EC 3.4.21.4), preferably trypsin, such as, without limitation, preparations of trypsin from bovine pancreas, human pancreas, porcine pancreas, recombinant trypsin, Lys-acetylated trypsin, trypsin in solution, trypsin immobilised to a solid support, etc. Trypsin is particularly useful, inter alia due to high specificity and efficiency of cleavage. The invention also contemplates the use of any trypsin-like protease, i.e., with a similar specificity to that of trypsin.

Otherwise, chemical reagents may be used for proteolysis. For example, CNBr can cleave at Met; BNPS-skatole can cleave at Trp.

The conditions for treatment, e.g., protein concentration, enzyme or chemical reagent concentration, pH, buffer, temperature, time, can be determined by the skilled person depending on the enzyme or chemical reagent employed.

Hence, in an aspect the invention also provides an isolated fragment of Quiescin Q6 as defined here above. Such fragments may give useful information about the presence and quantity of Quiescin Q6 in biological samples, whereby the detection of said fragments is of interest. Hence, the herein disclosed fragments of Quiescin Q6 are useful biomarkers.

The term "isolated" with reference to a particular component (such as for instance, a protein, polypeptide, peptide or fragment thereof) generally denotes that such component exists in separation from—for example, has been separated from or prepared in separation from—one or more other components of its natural environment. For instance, an isolated human or animal protein, polypeptide, peptide or fragment exists in separation from a human or animal body where it occurs naturally.

The term "isolated" as used herein may preferably also encompass the qualifier "purified". As used herein, the term "purified" with reference to protein(s), polypeptide(s), peptide(s) and/or fragment(s) thereof does not require absolute purity. Instead, it denotes that such protein(s), polypeptide(s), peptide(s) and/or fragment(s) is (are) in a discrete environment in which their abundance (conveniently expressed in terms of mass or weight or concentration) relative to other proteins is greater than in a biological sample. A discrete environment denotes a single medium, such as for example a single solution, gel, precipitate, lyophilisate, etc. Purified peptides, polypeptides or fragments may be obtained by known methods including, for example, laboratory or recombinant synthesis, chromatography, preparative electrophoresis, centrifugation, precipitation, affinity purification, etc.

Purified protein(s), polypeptide(s), peptide(s) and/or fragment(s) may preferably constitute by weight≥10%, more preferably ≥50%, such as ≥60%, yet more preferably ≥70%, such as ≥80%, and still more preferably ≥90%, such as ≥95%, ≥96%, ≥97%, ≥98%, ≥99% or even 100%, of the protein content of the discrete environment. Protein content may be determined, e.g., by the Lowry method (Lowry et al. 1951. J Biol Chem 193: 265), optionally as described by Hartree 1972 (Anal Biochem 48: 422-427). Also, purity of peptides or polypeptides may be determined by SDS-PAGE under reducing or non-reducing conditions using Coomassie blue or, preferably, silver stain.

A further embodiment provides isolated Quiescin Q6 or fragments of Quiescin Q6 as taught herein comprising a detectable label. This facilitates ready detection of such fragments. The term "label" as used throughout this specification refers to any atom, molecule, moiety or biomolecule that can be used to provide a detectable and preferably quantifiable read-out or property, and that can be attached to or made part of an entity of interest, such as a peptide or polypeptide or a specific-binding agent. Labels may be suitably detectable by mass spectrometric, spectroscopic, optical, colorimetric, magnetic, photochemical, biochemical, immunochemical or chemical means. Labels include without limitation dyes; radiolabels such as $^{32}P$, $^{33}P$, $^{35}S$, $^{125}I$, $^{131}I$; electron-dense reagents; enzymes (e.g., horseradish peroxidase or alkaline phosphatase as commonly used in immunoassays); binding moieties such as biotin-streptavidin; haptens such as digoxigenin; luminogenic, phosphorescent or fluorogenic moieties; mass tags; and fluorescent dyes alone or in combination with moieties that can suppress or shift emission spectra by fluorescence resonance energy transfer (FRET).

In an embodiment, the isolated Quiescin Q6 or fragments of Quiescin Q6 as taught herein may be labelled by a mass-altering label. Preferably, a mass-altering label may involve the presence of a distinct stable isotope in one or more amino acids of the peptide vis-à-vis its corresponding non-labelled peptide. Mass-labelled peptides are particularly useful as positive controls, standards and calibrators in mass spectrometry applications. In particular, peptides including one or more distinct isotopes are chemically alike, separate chromatographically and electrophoretically in the same manner and also ionise and fragment in the same way. However, in a suitable mass analyser such peptides and optionally select fragmentation ions thereof will display distinguishable m/z ratios and can thus be discriminated. Examples of pairs of distinguishable stable isotopes include H and D, $^{12}C$ and $^{13}C$, $^{14}N$ and $^{15}N$ or $^{16}O$ and $^{18}O$. Usually, peptides and proteins of biological samples analysed in the present invention may substantially only contain common isotopes having high prevalence in nature, such as for example H, $^{12}C$, $^{14}N$ and $^{16}O$. In such case, the mass-labelled peptide may be labelled with one or more uncommon isotopes having low prevalence in nature, such as for instance D, $^{13}O$, $^{15}N$ and/or $^{18}O$. It is also conceivable that in cases where the peptides or proteins of a biological sample would include one or more uncommon isotopes, the mass-labelled peptide may comprise the respective common isotope(s).

Isotopically-labelled synthetic peptides may be obtained inter alia by synthesising or recombinantly producing such peptides using one or more isotopically-labelled amino acid substrates, or by chemically or enzymatically modifying unlabelled peptides to introduce thereto one or more distinct isotopes. By means of example and not limitation, D-labelled peptides may be synthesised or recombinantly produced in the presence of commercially available deuterated L-methionine $CH_3$—S—$CD_2CD_2$-$CH(NH_2)$—COOH or deuterated arginine $H_2NC(=NH)$—NH—$(CD_2)_3$-$CD(NH_2)$—COOH. It shall be appreciated that any amino acid of which deuterated or $^{15}N$- or $^{13}C$-containing forms exist may be considered for synthesis or recombinant production of labelled peptides. In another non-limiting example, a peptide may be treated with trypsin in $H_2^{16}O$ or $H_2^{18}O$, leading to incorporation of two oxygens ($^{16}O$ or $^{18}O$, respectively) at the COOH-termini of said peptide (e.g., US 2006/105415).

Accordingly, also contemplated is the use of Quiescin Q6 and isolated fragments of Quiescin Q6 as taught herein, optionally comprising a detectable label, as (positive) controls, standards or calibrators in qualitative or quantitative detection assays (measurement methods) of Quiescin Q6, and particularly in such methods for predicting, diagnosing and/or prognosticating AHF in subjects as taught herein. The proteins, polypeptides or peptides may be supplied in any form, inter alia as precipitate, vacuum-dried, lyophilisate, in solution as liquid or frozen, or covalently or non-covalently immobilised on solid phase, such as for example, on solid chromatographic matrix or on glass or plastic or other suitable surfaces (e.g., as a part of peptide arrays and microarrays). The peptides may be readily prepared, for example, isolated from natural sources, or prepared recombinantly or synthetically.

Also provided are binding agents capable of specifically binding to any one or more of the isolated fragments of Quiescin Q6 as taught herein. Further provided are binding agents capable of specifically binding to only one of the isolated fragments of Quiescin Q6 as taught herein. Such binding agents may include inter alia an antibody, aptamer, photoaptamer, protein, peptide, peptidomimetic or a small molecule.

The term "specifically bind" as used throughout this specification means that an agent (denoted herein also as "specific-binding agent") binds to one or more desired molecules or analytes, such as to one or more proteins, polypeptides or peptides of interest or fragments thereof substantially to the exclusion of other molecules which are random or unrelated, and optionally substantially to the exclusion of other molecules that are structurally related.

The term "specifically bind" does not necessarily require that an agent binds exclusively to its intended target(s). For example, an agent may be said to specifically bind to protein(s) polypeptide(s), peptide(s) and/or fragment(s) thereof of interest if its affinity for such intended target(s) under the conditions of binding is at least about 2-fold greater, preferably at least about 5-fold greater, more preferably at least about 10-fold greater, yet more preferably at least about 25-fold greater, still more preferably at least about 50-fold greater, and even more preferably at least about 100-fold or more greater, than its affinity for a non-target molecule.

Preferably, the agent may bind to its intended target(s) with affinity constant ($K_A$) of such binding $K_A \geq 1\times10^6$ $M^{-1}$, more preferably $K_A \geq 1\times10^7$ $M^{-1}$, yet more preferably $K_A \geq 1\times10^8$ $M^{-1}$, even more preferably $K_A \geq 1\times10^9$ $M^{-1}$, and still more preferably $K_A \geq 1\times10^{10}$ $M^{-1}$ or $K_A \geq 1\times10^{11}$ $M^{-1}$, wherein $K_A$=[SBA_T]/[SBA][T], SBA denotes the specific-binding agent, T denotes the intended target. Determination of $K_A$ can be carried out by methods known in the art, such as for example, using equilibrium dialysis and Scatchard plot analysis.

Specific-binding agents as used throughout this specification may include inter alia an antibody, aptamer, photoaptamer, protein, peptide, peptidomimetic or a small molecule.

As used herein, the term "antibody" is used in its broadest sense and generally refers to any immunologic binding agent. The term specifically encompasses intact monoclonal antibodies, polyclonal antibodies, multivalent (e.g., 2-, 3- or more-valent) and/or multi-specific antibodies (e.g., bi- or more-specific antibodies) formed from at least two intact antibodies, and antibody fragments insofar they exhibit the desired biological activity (particularly, ability to specifically bind an antigen of interest), as well as multivalent and/or multi-specific composites of such fragments. The term "antibody" is not only inclusive of antibodies generated by methods comprising immunisation, but also includes any polypeptide, e.g., a recombinantly expressed polypeptide, which is made to encompass at least one complementarity-determining region (CDR) capable of specifically binding to an epitope on an antigen of interest. Hence, the term applies to such molecules regardless whether they are produced in vitro or in vivo.

In an embodiment, an antibody may be any of IgA, IgD, IgE, IgG and IgM classes, and preferably IgG class antibody.

In an embodiment, the antibody may be a polyclonal antibody, e.g., an antiserum or immunoglobulins purified there from (e.g., affinity-purified).

In another preferred embodiment, the antibody may be a monoclonal antibody or a mixture of monoclonal antibodies. Monoclonal antibodies can target a particular antigen or a particular epitope within an antigen with greater selectivity and reproducibility.

By means of example and not limitation, monoclonal antibodies may be made by the hybridoma method first described by Kohler et al. 1975 (Nature 256: 495), or may be made by recombinant DNA methods (e.g., as in U.S. Pat. No. 4,816,567). Monoclonal antibodies may also be isolated from phage antibody libraries using techniques as described by Clackson et al. 1991 (Nature 352: 624-628) and Marks et al. 1991 (J Mol Biol 222: 581-597), for example.

In further embodiments, the antibody binding agents may be antibody fragments. "Antibody fragments" comprise a portion of an intact antibody, comprising the antigen-binding or variable region thereof. Examples of antibody fragments include Fab, Fab', F(ab')2, Fv and scFv fragments; diabodies; linear antibodies; single-chain antibody molecules; and multivalent and/or multispecific antibodies formed from antibody fragment(s), e.g., dibodies, tribodies, and multibodies. The above designations Fab, Fab', F(ab')2, Fv, scFv etc. are intended to have their art-established meaning.

The term antibody includes antibodies originating from or comprising one or more portions derived from any animal species, preferably vertebrate species, including, e.g., birds and mammals. Without limitation, the antibodies may be chicken, turkey, goose, duck, guinea fowl, quail or pheasant. Also without limitation, the antibodies may be human, murine (e.g., mouse, rat, etc.), donkey, rabbit, goat, sheep, guinea pig, camel (e.g., *Camelus bactrianus* and *Camelus dromaderius*), llama (e.g., *Lama paccos, Lama glama* or *Lama vicugna*) or horse.

A skilled person will understand that an antibody can include one or more amino acid deletions, additions and/or substitutions (e.g., conservative substitutions), insofar such alterations preserve its binding of the respective antigen. An antibody may also include one or more native or artificial modifications of its constituent amino acid residues (e.g., glycosylation, etc.).

Methods of producing polyclonal and monoclonal antibodies as well as fragments thereof are well known in the art, as are methods to produce recombinant antibodies or fragments thereof (see for example, Harlow and Lane, "Antibodies: A Laboratory Manual", Cold Spring Harbour Laboratory, New York, 1988; Harlow and Lane, "Using Antibodies: A Laboratory Manual", Cold Spring Harbour Laboratory, New York, 1999, ISBN 0879695447; "Monoclonal Antibodies: A Manual of Techniques", by Zola, ed., CRC Press 1987, ISBN 0849364760; "Monoclonal Antibodies: A Practical Approach", by Dean & Shepherd, eds., Oxford University Press 2000, ISBN 0199637229; Methods in Molecular Biology, vol. 248: "Antibody Engineering: Methods and Protocols", Lo, ed., Humana Press 2004, ISBN 1588290921).

The term "aptamer" refers to single-stranded or double-stranded oligo-DNA, oligo-RNA or oligo-DNA/RNA or any analogue thereof, that can specifically bind to a target molecule such as a peptide. Advantageously, aptamers can display fairly high specificity and affinity (e.g., $K_A$ in the order $1\times10^9$ $M^{-1}$) for their targets. Aptamer production is described inter alia in U.S. Pat. No. 5,270,163; Ellington & Szostak 1990 (Nature 346: 818-822); Tuerk & Gold 1990

(Science 249: 505-510); or "The Aptamer Handbook: Functional Oligonucleotides and Their Applications", by Klussmann, ed., Wiley-VCH 2006, ISBN 3527310592, incorporated by reference herein. The term "photoaptamer" refers to an aptamer that contains one or more photoreactive functional groups that can covalently bind to or crosslink with a target molecule. The term "peptidomimetic" refers to a non-peptide agent that is a topological analogue of a corresponding peptide. Methods of rationally designing peptidomimetics of peptides are known in the art. For example, the rational design of three peptidomimetics based on the sulphated 8-mer peptide CCK26-33, and of two peptidomimetics based on the 11-mer peptide Substance P, and related peptidomimetic design principles, are described in Horwell 1995 (Trends Biotechnol 13: 132-134).

The term "small molecule" refers to compounds, preferably organic compounds, with a size comparable to those organic molecules generally used in pharmaceuticals. The term excludes biological macromolecules (e.g., proteins, nucleic acids, etc.). Preferred small organic molecules range in size up to about 5000 Da, e.g., up to about 4000, preferably up to 3000 Da, more preferably up to 2000 Da, even more preferably up to about 1000 Da, e.g., up to about 900, 800, 700, 600 or up to about 500 Da.

Also provided are methods for immunising animals, e.g., non-human animals such as laboratory or farm, animals using (i.e., using as the immunising antigen) the herein taught fragments of Quiescin Q6, optionally attached to a presenting carrier. Immunisation and preparation of antibody reagents from immune sera is well-known per se and described in documents referred to elsewhere in this specification. The animals to be immunised may include any animal species, preferably warm-blooded species, more preferably vertebrate species, including, e.g., birds and mammals. Without limitation, the antibodies may be chicken, turkey, goose, duck, guinea fowl, quail or pheasant. Also without limitation, the antibodies may be human, murine (e.g., mouse, rat, etc.), donkey, rabbit, goat, sheep, guinea pig, camel, llama or horse.

The term "presenting carrier" or "carrier" generally denotes an immunogenic molecule which, when bound to a second molecule, augments immune responses to the latter, usually through the provision of additional T cell epitopes. The presenting carrier may be a (poly)peptidic structure or a non-peptidic structure, such as inter alia glycans, polyethylene glycols, peptide mimetics, synthetic polymers, etc. Exemplary non-limiting carriers include human Hepatitis B virus core protein, multiple C3d domains, tetanus toxin fragment C or yeast Ty particles.

Immune sera obtained or obtainable by immunisation as taught herein may be particularly useful for generating antibody reagents that specifically bind to one or more of the herein disclosed fragments of Quiescin Q6.

The invention also teaches a method for selecting specific-binding agents which bind (a) one or more of the Quiescin Q6 fragments taught herein, substantially to the exclusion of (b) Quiescin Q6 and/or other fragments thereof. Conveniently, such methods may be based on subtracting or removing binding agents which cross-react or cross-bind the non-desired Quiescin Q6 molecules under (b). Such subtraction may be readily performed as known in the art by a variety of affinity separation methods, such as affinity chromatography, affinity solid phase extraction, affinity magnetic extraction, etc.

Any existing, available or conventional separation, detection and quantification methods can be used herein to measure the presence or absence (e.g., readout being present vs. absent; or detectable amount vs. undetectable amount) and/or quantity (e.g., readout being an absolute or relative quantity, such as, for example, absolute or relative concentration) of Quiescin Q6 and/or fragments thereof and optionally of the one or more biomarkers useful for AHF in samples (any molecules or analytes of interest to be so-measured in samples, including Quiescin Q6 and fragments thereof, may be herein below referred to collectively as biomarkers).

For example, such methods may include immunoassay methods, mass spectrometry analysis methods, or chromatography methods, or combinations thereof.

The term "immunoassay" generally refers to methods known as such for detecting one or more molecules or analytes of interest in a sample, wherein specificity of an immunoassay for the molecule(s) or analyte(s) of interest is conferred by specific binding between a specific-binding agent, commonly an antibody, and the molecule(s) or analyte(s) of interest.

Immunoassay technologies include without limitation direct ELISA (enzyme-linked immunosorbent assay), indirect ELISA, sandwich ELISA, competitive ELISA, multiplex ELISA, radioimmunoassay (RIA), ELISPOT technologies, and other similar techniques known in the art. Principles of these immunoassay methods are known in the art, for example John R. Crowther, "The ELISA Guidebook", 1st ed., Humana Press 2000, ISBN 0896037282.

By means of further explanation and not limitation, direct ELISA employs a labelled primary antibody to bind to and thereby quantify target antigen in a sample immobilised on a solid support such as a microwell plate. Indirect ELISA uses a non-labelled primary antibody which binds to the target antigen and a secondary labelled antibody that recognises and allows to quantify the antigen-bound primary antibody. In sandwich ELISA the target antigen is captured from a sample using an immobilised 'capture' antibody which binds to one antigenic site within the antigen, and subsequent to removal of non-bound analytes the so-captured antigen is detected using a 'detection' antibody which binds to another antigenic site within said antigen, where the detection antibody may be directly labelled or indirectly detectable as above. Competitive ELISA uses a labelled 'competitor' that may either be the primary antibody or the target antigen. In an example, non-labelled immobilised primary antibody is incubated with a sample, this reaction is allowed to reach equilibrium, and then labelled target antigen is added. The latter will bind to the primary antibody wherever its binding sites are not yet occupied by non-labelled target antigen from the sample. Thus, the detected amount of bound labelled antigen inversely correlates with the amount of non-labelled antigen in the sample. Multiplex ELISA allows simultaneous detection of two or more analytes within a single compartment (e.g., microplate well) usually at a plurality of array addresses (see, for example, Nielsen & Geierstanger 2004. J Immunol Methods 290: 107-20 and Ling et al. 2007. Expert Rev Mol Diagn 7: 87-98 for further guidance). As appreciated, labelling in ELISA technologies is usually by enzyme (such as, e.g., horseradish peroxidase) conjugation and the end-point is typically colorimetric, chemiluminescent or fluorescent.

Radioimmunoassay (RIA) is a competition-based technique and involves mixing known quantities of radioactively-labelled (e.g., $^{125}$I or $^{131}$I-labelled) target antigen with antibody to said antigen, then adding non-labelled or 'cold' antigen from a sample and measuring the amount of labelled antigen displaced (see, e.g., "An Introduction to Radioimmunoassay and Related Techniques", by Chard T, ed., Elsevier Science 1995, ISBN 0444821198 for guidance).

Further, mass spectrometry methods are suitable for measuring biomarkers.

Generally, any mass spectrometric (MS) techniques that can obtain precise information on the mass of peptides, and preferably also on fragmentation and/or (partial) amino acid sequence of selected peptides (e.g., in tandem mass spectrometry, MS/MS; or in post source decay, TOF MS), are useful herein. Suitable peptide MS and MS/MS techniques and systems are well-known per se (see, e.g., Methods in Molecular Biology, vol. 146: "Mass Spectrometry of Proteins and Peptides", by Chapman, ed., Humana Press 2000, ISBN 089603609x; Biemann 1990. Methods Enzymol 193: 455-79; or Methods in Enzymology, vol. 402: "Biological Mass Spectrometry", by Burlingame, ed., Academic Press 2005, ISBN 9780121828073) and may be used herein.

MS arrangements, instruments and systems suitable for biomarker peptide analysis may include, without limitation, matrix-assisted laser desorption/ionisation time-of-flight (MALDI-TOF) MS; MALDI-TOF post-source-decay (PSD); MALDI-TOF/TOF; surface-enhanced laser desorption/ionization time-of-flight mass spectrometry (SELDI-TOF) MS; electrospray ionization mass spectrometry (ESI-MS); ESI-MS/MS; ESI-MS/(MS)$^n$ (n is an integer greater than zero); ESI 3D or linear (2D) ion trap MS; ESI triple quadrupole MS; ESI quadrupole orthogonal TOF (Q-TOF); ESI Fourier transform MS systems; desorption/ionization on silicon (DIOS); secondary ion mass spectrometry (SIMS); atmospheric pressure chemical ionization mass spectrometry (APCI-MS); APCI-MS/MS; APCI-(MS)$^n$; atmospheric pressure photoionization mass spectrometry (APPI-MS); APPI-MS/MS; and APPI-(MS)$^n$. Peptide ion fragmentation in tandem MS (MS/MS) arrangements may be achieved using manners established in the art, such as, e.g., collision induced dissociation (CID).

In an embodiment, detection and quantification of biomarkers by mass spectrometry may involve multiple reaction monitoring (MRM), such as described among others by Kuhn et al. 2004 (Proteomics 4: 1175-86).

In an embodiment, MS peptide analysis methods may be advantageously combined with upstream peptide or protein separation or fractionation methods, such as for example with the chromatographic and other methods described herein below.

Chromatography can also be used for measuring biomarkers. As used herein, the term "chromatography" encompasses methods for separating chemical substances, referred to as such and vastly available in the art. In a preferred approach, chromatography refers to a process in which a mixture of chemical substances (analytes) carried by a moving stream of liquid or gas ("mobile phase") is separated into components as a result of differential distribution of the analytes, as they flow around or over a stationary liquid or solid phase ("stationary phase"), between said mobile phase and said stationary phase. The stationary phase may be usually a finely divided solid, a sheet of filter material, or a thin film of a liquid on the surface of a solid, or the like. Chromatography is also widely applicable for the separation of chemical compounds of biological origin, such as, e.g., amino acids, proteins, fragments of proteins or peptides, etc.

Chromatography as used herein may be preferably columnar (i.e., wherein the stationary phase is deposited or packed in a column), preferably liquid chromatography, and yet more preferably HPLC. While particulars of chromatography are well known in the art, for further guidance see, e.g., Meyer M., 1998, ISBN: 047198373X, and "Practical HPLC Methodology and Applications", Bidlingmeyer, B. A., John Wiley & Sons Inc., 1993.

Exemplary types of chromatography include, without limitation, high-performance liquid chromatography (HPLC), normal phase HPLC (NP-HPLC), reversed phase HPLC (RP-HPLC), ion exchange chromatography (IEC), such as cation or anion exchange chromatography, hydrophilic interaction chromatography (HILIC), hydrophobic interaction chromatography (HIC), size exclusion chromatography (SEC) including gel filtration chromatography or gel permeation chromatography, chromatofocusing, affinity chromatography such as immuno-affinity, immobilised metal affinity chromatography, and the like.

In an embodiment, chromatography, including single-, two- or more-dimensional chromatography, may be used as a peptide fractionation method in conjunction with a further peptide analysis method, such as for example, with a downstream mass spectrometry analysis as described elsewhere in this specification.

Further peptide or polypeptide separation, identification or quantification methods may be used, optionally in conjunction with any of the above described analysis methods, for measuring biomarkers in the present disclosure. Such methods include, without limitation, chemical extraction partitioning, isoelectric focusing (IEF) including capillary isoelectric focusing (CIEF), capillary isotachophoresis (CITP), capillary electrochromatography (CEC), and the like, one-dimensional polyacrylamide gel electrophoresis (PAGE), two-dimensional polyacrylamide gel electrophoresis (2D-PAGE), capillary gel electrophoresis (CGE), capillary zone electrophoresis (CZE), micellar electrokinetic chromatography (MEKC), free flow electrophoresis (FFE), etc.

The various aspects and embodiments taught herein may further rely on comparing the quantity of Quiescin Q6 measured in samples with reference values of the quantity of Quiescin Q6, wherein said reference values represent known predictions, diagnoses and/or prognoses of AHF.

For example, distinct reference values may represent the prediction of a risk (e.g., an abnormally elevated risk) of having AHF vs. the prediction of no or normal risk of having AHF. In another example, distinct reference values may represent predictions of differing degrees of risk of having AHF.

In a further example, distinct reference values can represent the diagnosis of AHF vs. the diagnosis of no AHF (such as, e.g., the diagnosis of healthy, CHF or recovered from AHF, etc.). In another example, distinct reference values may represent the diagnosis of AHF of varying severity.

In yet another example, distinct reference values may represent a good prognosis for AHF vs. a poor prognosis for AHF. In a further example, distinct reference values may represent varyingly favourable or unfavourable prognoses for AHF.

Such comparison may generally include any means to determine the presence or absence of at least one difference and optionally of the size of such different between values or profiles being compared. A comparison may include a visual inspection, an arithmetical or statistical comparison of measurements. Such statistical comparisons include, but are not limited to, applying a rule. If the values or biomarker profiles comprise at least one standard, the comparison to determine a difference in said values or biomarker profiles may also include measurements of these standards, such that measurements of the biomarker are correlated to measurements of the internal standards.

Reference values for the quantity of Quiescin Q6 may be established according to known procedures previously employed for other biomarkers.

For example, a reference value of the quantity of Quiescin Q6 for a particular prediction, diagnosis and/or prognosis of AHF may be established by determining the quantity of Quiescin Q6 in sample(s) from one individual or from a population of individuals characterised by said particular prediction, diagnosis and/or prognosis of AHF (i.e., for whom said prediction, diagnosis and/or prognosis of AHF holds true). Such population may comprise without limitation $\geq 2$, $\geq 10$, $\geq 100$, or even several hundreds or more individuals.

Hence, by means of an illustrative example, reference values of the quantity of Quiescin Q6 for the diagnoses of AHF vs. no AHF may be established by determining the quantity of Quiescin Q6 in sample(s) from one individual or from a population of individuals diagnosed (e.g., based on other adequately conclusive means, such as, for example, clinical signs and symptoms, imaging, ECG, etc.) as, respectively, having or not having AHF.

In an embodiment, reference value(s) as intended herein may convey absolute quantities of Quiescin Q6. In another embodiment, the quantity of Quiescin Q6 in a sample from a tested subject may be determined directly relative to the reference value (e.g., in terms of increase or decrease, or fold-increase or fold-decrease). Advantageously, this may allow to compare the quantity of Quiescin Q6 in the sample from the subject with the reference value (in other words to measure the relative quantity of Quiescin Q6 in the sample from the subject vis-à-vis the reference value) without the need to first determine the respective absolute quantities of Quiescin Q6.

In heart failure or otherwise cardiovascular compromised patients, biomarkers are often used to track the clinical status. For example, BNP or NT-proBNP levels follow the symptomatic New York Heart Association Class (NYHAC) classification system. The greater the impairment of the symptoms the higher the average BNP levels among the patients in the same group. The class corresponding ranges are however very large to accommodate the wide spectrum of underlying causal diseases.

Intra-individual (i.e. in the same patient) biomarker ranges and a significant change thereof correlating to clinical status are likely to be tighter and more accurate ranges than cross-population ranges like NYHAC. Therefore, the intra-individual biomarker change is a more sensitive signal and requires different ranges or changes to correlate to clinical status. A patient may furthermore also show a drop in biomarker levels because of therapeutic intervention or bettering of the clinical status. The level of the biomarker may fall back to the original stable patient levels.

Markers may fluctuate, increase or decrease significantly without change (appearance of, worsening or improving of) symptoms. In such an event, the marker change precedes the change in symptoms and becomes a more sensitive measure than symptom change. Therapeutic intervention can be initiated earlier and be more effective than waiting for deteriorating symptoms. Symptoms can be (but not limited to): shortness of breath, oedema in lower extremities, heart palpitations, fatigue, etc. Early intervention at a more benign status may be carried out safely at home, which is a major improvement from treating seriously deteriorated patients in the emergency room.

Measuring the Quiescin Q6 level of the same patient at different time points will thus enable the continuous monitoring of the status of the patient and can lead to prediction of worsening or improvement of the patient's condition with regard to AHF. A home test or device as indicated below can be used for this continuous monitoring, wherein said reference value or range can be determined beforehand or during the monitoring process over a certain period of time, resulting in a base-line value or range of Quiescin Q6 presence in the patient. A sudden deviation of the Quiescin Q6 levels from said reference value can predict the worsening of the condition of the patient (e.g. at home) and enable him to contact a medical practitioner or the emergency services right away, i.e. before the (often severe) symptoms actually can be felt or observed.

The invention therefore also provides a method or algorithm for determining a significant change in the level of the Quiescin Q6 marker in a certain patient, which is indicative for change (worsening or improving) in clinical status.

In an embodiment the present methods may include a step of establishing such reference value(s). In an embodiment, the present kits and devices may include means for establishing a reference value of the quantity of Quiescin Q6 for a particular prediction, diagnosis and/or prognosis of AHF. Such means may for example comprise one or more samples (e.g., separate or pooled samples) from one or more individuals characterised by said particular prediction, diagnosis and/or prognosis of AHF.

The various aspects and embodiments taught herein may further entail finding a deviation or no deviation between the quantity of Quiescin Q6 measured in a sample from a subject and a given reference value.

A "deviation" of a first value from a second value may generally encompass any direction (e.g., increase: first value>second value; or decrease: first value<second value) and any extent of alteration.

For example, a deviation may encompass a decrease in a first value by, without limitation, at least about 10% (about 0.9-fold or less), or by at least about 20% (about 0.8-fold or less), or by at least about 30% (about 0.7-fold or less), or by at least about 40% (about 0.6-fold or less), or by at least about 50% (about 0.5-fold or less), or by at least about 60% (about 0.4-fold or less), or by at least about 70% (about 0.3-fold or less), or by at least about 80% (about 0.2-fold or less), or by at least about 90% (about 0.1-fold or less), relative to a second value with which a comparison is being made.

For example, a deviation may encompass an increase of a first value by, without limitation, at least about 10% (about 1.1-fold or more), or by at least about 20% (about 1.2-fold or more), or by at least about 30% (about 1.3-fold or more), or by at least about 40% (about 1.4-fold or more), or by at least about 50% (about 1.5-fold or more), or by at least about 60% (about 1.6-fold or more), or by at least about 70% (about 1.7-fold or more), or by at least about 80% (about 1.8-fold or more), or by at least about 90% (about 1.9-fold or more), or by at least about 100% (about 2-fold or more), or by at least about 150% (about 2.5-fold or more), or by at least about 200% (about 3-fold or more), or by at least about 500% (about 6-fold or more), or by at least about 700% (about 8-fold or more), or like, relative to a second value with which a comparison is being made.

Preferably, a deviation may refer to a statistically significant observed alteration. For example, a deviation may refer to an observed alteration which falls outside of error margins of reference values in a given population (as expressed, for example, by standard deviation or standard error, or by a predetermined multiple thereof, e.g., $\pm 1 \times SD$ or $\pm 2 \times SD$, or $\pm 1 \times SE$ or $\pm 2 \times SE$). Deviation may also refer to a value falling outside of a reference range defined by values in a given population (for example, outside of a range which comprises ≥40%, ≥50%, ≥60%, ≥70%, ≥75% or ≥80% or ≥85% or ≥90% or ≥95% or even ≥100% of values in said population).

In a further embodiment, a deviation may be concluded if an observed alteration is beyond a given threshold or cut-off. Such threshold or cut-off may be selected as generally known in the art to provide for a chosen sensitivity and/or specificity of the prediction, diagnosis and/or prognosis methods, e.g., sensitivity and/or specificity of at least 50%, or at least 60%, or at least 70%, or at least 80%, or at least 85%, or at least 90%, or at least 95%.

For example, in an embodiment, an elevated quantity of Quiescin Q6 in the sample from the subject—preferably at least about 1.1-fold elevated, or at least about 1.2-fold elevated, more preferably at least about 1.3-fold elevated, even more preferably at least about 1.4-fold elevated, yet more preferably at least about 1.5-fold elevated, such as between about 1.1-fold and 3-fold elevated or between about 1.5-fold and 2-fold elevated—compared to a reference value representing the prediction or diagnosis of no AHF or representing a good prognosis for AHF indicates that the subject has or is at risk of having AHF or indicates a poor prognosis for AHF in the subject.

When a deviation is found between the quantity of Quiescin Q6 in a sample from a subject and a reference value representing a certain prediction, diagnosis and/or prognosis of AHF, said deviation is indicative of or may be attributed to the conclusion that the prediction, diagnosis and/or prognosis of AHF in said subject is different from that represented by the reference value.

When no deviation is found between the quantity of Quiescin Q6 in a sample from a subject and a reference value representing a certain prediction, diagnosis and/or prognosis of AHF, the absence of such deviation is indicative of or may be attributed to the conclusion that the prediction, diagnosis and/or prognosis of AHF in said subject is substantially the same as that represented by the reference value.

The above considerations apply analogously to biomarker profiles.

When two or more different biomarkers are determined in a subject, their respective presence, absence and/or quantity may be together represented as a biomarker profile, the values for each measured biomarker making a part of said profile. As used herein, the term "profile" includes any set of data that represents the distinctive features or characteristics associated with a condition of interest, such as with a particular prediction, diagnosis and/or prognosis of AHF. The term generally encompasses inter alia nucleic acid profiles, such as for example genotypic profiles (sets of genotypic data that represents the genotype of one or more genes associated with a condition of interest), gene copy number profiles (sets of gene copy number data that represents the amplification or deletion of one or more genes associated with a condition of interest), gene expression profiles (sets of gene expression data that represents the mRNA levels of one or more genes associated with a condition of interest), DNA methylation profiles (sets of methylation data that represents the DNA methylation levels of one or more genes associated with a condition of interest), as well as protein, polypeptide or peptide profiles, such as for example protein expression profiles (sets of protein expression data that represents the levels of one or more proteins associated with a condition of interest), protein activation profiles (sets of data that represents the activation or inactivation of one or more proteins associated with a condition of interest), protein modification profiles (sets of data that represents the modification of one or more proteins associated with a condition of interest), protein cleavage profiles (sets of data that represent the proteolytic cleavage of one or more proteins associated with a condition of interest), as well as any combinations thereof.

Biomarker profiles may be created in a number of ways and may be the combination of measurable biomarkers or aspects of biomarkers using methods such as ratios, or other more complex association methods or algorithms (e.g., rule-based methods). A biomarker profile comprises at least two measurements, where the measurements can correspond to the same or different biomarkers. A biomarker profile may also comprise at least three, four, five, 10, 20, 30 or more measurements. In one embodiment, a biomarker profile comprises hundreds, or even thousands, of measurements.

Hence, for example, distinct reference profiles may represent the prediction of a risk (e.g., an abnormally elevated risk) of having AHF vs. the prediction of no or normal risk of having AHF.

In another example, distinct reference profiles may represent predictions of differing degrees of risk of having AHF.

In a further example, distinct reference profiles can represent the diagnosis of AHF vs. the diagnosis no AHF (such as, e.g., the diagnosis of healthy, CHF or recovered from AHF, etc.). In another example, distinct reference profiles may represent the diagnosis of AHF of varying severity.

In a yet another example, distinct reference profiles may represent a good prognosis for AHF vs. a poor prognosis for AHF. In a further example, distinct reference profiles may represent varyingly favourable or unfavourable prognoses for AHF.

Reference profiles used herein may be established according to known procedures previously employed for other biomarkers.

For example, a reference profile of the quantity of Quiescin Q6 and the presence or absence and/or quantity of one or more other AHF-related biomarkers for a particular prediction, diagnosis and/or prognosis of AHF may be established by determining the profile in sample(s) from one individual or from a population of individuals characterised by said particular prediction, diagnosis and/or prognosis of AHF (i.e., for whom said prediction, diagnosis and/or prognosis of AHF holds true). Such population may comprise without limitation ≥2, ≥10, ≥100, or even several hundreds or more individuals.

Hence, by means of an illustrative example, reference profiles for the diagnoses of AHF vs. no AHF may be established by determining the biomarker profiles in sample(s) from one individual or from a population of individuals diagnosed as, respectively, having or not having AHF.

In an embodiment the present methods may include a step of establishing such reference profile(s). In an embodiment, the present kits and devices may include means for establishing a reference profile for a particular prediction, diagnosis and/or prognosis of AHF. Such means may for example comprise one or more samples (e.g., separate or pooled samples) from one or more individuals characterised by said particular prediction, diagnosis and/or prognosis of AHF.

Further, art-known multi-parameter analyses may be employed mutatis mutandis to determine deviations between groups of values and profiles generated there from (e.g., between sample and reference biomarker profiles).

When a deviation is found between the sample profile and a reference profile representing a certain prediction, diagnosis and/or prognosis of AHF, said deviation is indicative of or may be attributed to the conclusion that the prediction, diagnosis and/or prognosis of AHF in said subject is different from that represented by the reference profile.

When no deviation is found between the sample profile and a reference profile representing a certain prediction, diagnosis and/or prognosis of AHF, the absence of such deviation is indicative of or may be attributed to the conclusion that the prediction, diagnosis and/or prognosis of AHF in said subject is substantially the same as that represented by the reference profile.

The present invention further provides kits or devices for diagnosis of heart failure, more particularly of acute heart failure, comprising means for detecting the level of the Quiescin Q6 marker in a sample of the patient. In a more preferred embodiment, such a kit or kits of the invention can be used in clinical settings or at home. The kit according to the invention can be used for diagnosing Acute Heart Failure, for monitoring the effectiveness of treatment of a subject suffering from AHF with an agent, or for preventive screening of subjects for the occurrence of AHF in said subject.

In a clinical setting, the kit or device can be in the form of a bed-side device or in an emergency team setting, e.g. as part of the equipment of an ambulance or other moving emergency vehicle or team equipment or a as part of a first-aid kit. The diagnostic kit or device can assist a medical practitioner, a first aid helper, or nurse to decide whether the patient under observation is developing an acute heart failure, after which appropriate action or treatment can be performed.

A home-test kit gives the patient a readout which he can communicate to a medicinal practitioner, a first aid helper or to the emergency department of a hospital, after which appropriate action can be taken. Such a home-test device is of particular interest for people having either a history of, or are at risk of suffering from heart failure (e.g. chronic heart failure patients) or have a history or are at risk of suffering from dyspnea (shortness of breath), which may be caused by e.g. acute heart failure, infections, lung-problems, sepsis, etc. Such subjects with a high risk for heart failure or having a history of dyspnea could certainly benefit from having a home test device or kit according to the invention at home, because they can then easily distinguish between an acute heart failure event and another event causing the dyspnea, resulting in an easier way of determining the actions to be taken to resolve the problem.

Typical kits or devices according to the invention comprise the following elements:
a) a means for obtaining a sample from the subject
b) a means or device for measuring the amount of the Quiescin Q6 marker in said sample and visualizing whether the amount of the Quiescin Q6 marker in said sample is below or above a certain threshold level or value, indicating whether the subject is suffering from acute heart failure or not.

In any of the embodiments of the invention, the kits or devices can additionally comprise c) means for communicating directly with a medical practitioner, an emergency department of the hospital or a first aid post, indicating that a person is suffering from acute heart failure or not.

The term "threshold level or value" or "reference value" is used interchangeably as a synonym and is as defined herein. It can also be a range of base-line (e.g. "dry weight") values determined in an individual patient or in a group of patients with highly similar disease conditions.

In any of the embodiments of the invention, the device or kit or kits of the invention can additionally comprise means for detecting the level of an additional marker for heart failure or acute heart failure in the sample of said patient. Additional markers could for example be BNP or NT-pro-BNP or fragments of BNP or NT-pro-BNP.

In said kit of the invention, the means for obtaining a sample from the subject (a) can be any means for obtaining a sample from the subject known in the art. Examples for obtaining e.g. a blood sample are known in the art and could be any kind of finger or skin prick or lancet based device, which basically pierces the skin and results in a drop of blood being released from the skin. When a urine sample is used, the means for obtaining a sample from the subject can be in the form of an absorbent strip such as the ones used in home pregnancy tests known in the art. In analogy, a saliva sample could be obtained using a mount swab known in the art. Example of blood sampling devices or other sampling devices are for example given in U.S. Pat. Nos. 4,802,493, 4,966,159, 5,099,857, 6,095,988, 5,944,671, 4,553,541, 3,760,809, 5,395,388, 5,212,879, 5,630,828, 5,133,730, 4,653,513, 5,368,047, 5,569,287, 4,360,016, 5,413,006 and U.S. Pat. Applic. 2002/1 11565, 2004/0096959, 2005/143713, 2005/137525, 2003/01 53900, 2003/0088191, WO9955232, WO2005/049107, WO2004/060163, WO02/056751, WO02/1 00254, WO2003/022330, WO2004/066822, WO97/46157, WO0112330, WO2004/039429, or EP0364621, EP0078724, EP1212138, EP0081975, or EP0292928.

In said kit of the invention, the means or device for measuring the amount of the Quiescin Q6 marker in said sample (b) can be any means or device that can specifically detect the amount of the Quiescin Q6 protein in the sample. Examples are systems comprising Quiescin Q6 specific binding molecules attached to a solid phase, e.g. lateral flow strips or dipstick devices and the like well known in the art. One non-limiting example to perform a biochemical assay is to use a test-strip and labelled antibodies which combination does not require any washing of the membrane. The test strip is well known, for example, in the field of pregnancy testing kits where an anti-hCG antibody is present on the support, and is carried complexed with hCG by the flow of urine onto an immobilised second antibody that permits visualisation. Other non-limiting examples of such home test devices, systems or kits can be found for example in the following U.S. Pat. No. 6,107,045, U.S. Pat. Nos. 6,974,706, 5,108, 889, 6,027,944, 6,482,156, 6,511,814, 5,824,268, 5,726,010, 6,001,658 or U.S. patent applications: 2008/0090305 or 2003/0109067.

In a preferred embodiment, the invention provides a lateral flow device or dipstick. Such dipstick comprises a test strip allowing migration of a sample by capillary flow from one end of the strip where the sample is applied to the other end of such strip where presence of an analyte in said sample is measured.

In another embodiment, the invention provides a device comprising a reagent strip. Such reagent strip comprises one or more test pads which when wetted with the sample, provide a color change in the presence of an analyte and/or indicate the concentration of the protein in said sample.

In one preferred embodiment of the kit of the invention, the means or device (1) for measuring the amount of protein in a sample (b) is a solid support (7) having a proximal (2) and distal (3) end, comprising:
 a sample application zone (4) in the vicinity of the proximal end, a reaction zone (5) distal to the sample application zone (4), and a detection zone (6) distal to the reaction zone (5), whereby said support has a capillary property that directs a flow of fluid sample applied in the application zone in a direction from the proximal end to the distal end, optionally, the means or device also comprises a source of fluid, e.g. in a container, dropper pipette or vial, enabling viscous samples to flow easier through the strip.

The reaction zone (5) comprises one or more bands (10) of Quiescin Q6 binding molecule conjugated to a detection agent (e.g. colloidal gold) which Quiescin Q6 binding molecule conjugate is disposed on the solid support such that it can migrate with the capillary flow of fluid i.e. it is not immobilised. The detection zone (6) comprises one or more capture bands (11) comprising a population of Quiescin Q6 binding molecules immobilised on the solid support.

When a sample is applied to the sample application zone (4), it migrates towards the reaction zone (5) by capillary flow. Any Quiescin Q6 present in the sample reacts with the Quiescin Q6 labelled binding molecule conjugate, and the complex so formed is carried by capillary flow to the detection zone (6). The detection zone (6), having Quiescin Q6 binding molecules permanently immobilised thereon, captures and immobilises any complex, resulting in a localised concentration of conjugate that can be visualised.

The two zones (5 and 6) as described herein (one zone with the non-fixed conjugates and one zone with the fixed capture antibodies) generally do not overlap. They may be adjacently arranged with an absence or presence of an intervening gap of solid support devoid of band. A band may be disposed on a solid support by any means, for example, absorbed, adsorbed, coated, covalently attached or dried, depending on whether the reagent is required to be mobilised or not.

In order to obtain a semi-quantitative test strip in which only a signal is formed once the Quiescin Q6 protein level in the sample is higher than a certain predetermined threshold level or value, the reaction zone (5) comprising the non-fixed conjugated Quiescin Q6 binding molecules, could also comprise a predetermined amount of fixed Quiescin Q6 capture antibodies. This enables to capture away a certain amount of Quiescin Q6 protein present in the sample, corresponding to the threshold level or value as predetermined. The remaining amount of Quiescin Q6 protein (if any) bound by the conjugated or labelled binding molecules can then be allowed to migrate to the detection zone (6). In this case, the reaction zone (6) will only receive labelled binding molecule-Quiescin Q6 complexes and subsequently only produce a signal if the level of the Quiescin Q6 protein in the sample is higher than the predetermined threshold level or value.

Another possibility to determine whether the amount of the Quiescin Q6 protein in the sample is below or above a certain threshold level or value, is to use a primary capturing antibody capturing all Quiescin Q6 protein present in the sample, in combination with a labeled secondary antibody, developing a certain signal or color when bound to the solid phase. The intensity of the color or signal can then either be compared to a reference color or signal chart indicating that when the intensity of the signal is above a certain threshold signal, the test is positive (i.e. AHF is imminent). Alternatively, the amount or intensity of the color or signal can be measured with an electronic device comprising e.g. a light absorbance sensor or light emission meter, resulting in a numerical value of signal intensity or color absorbance formed, which can then be displayed to the subject in the form of a negative result if said numerical value is below the threshold value or a positive result if said numerical value is above the threshold value.

This embodiment is of particular relevance in monitoring the Quiescin Q6 level in a patient over a period of time.

The reference value or range can e.g. be determined using the home device in a period wherein the subject is free of AHF, giving the patient an indication of his base-line Quiescin Q6 level. Regularly using the home test device will thus enable the subject to notice a sudden change in Quiescin Q6 levels as compared to the base-line level, which can enable him to contact a medical practitioner.

Alternatively, the reference value can be determined in the subject suffering from AHF, which then indicates his personal Quiescin Q6 "risk level", i.e. the level of Quiescin Q6 which indicates he is or will soon be exposed to an AHF event. This risk level is interesting for monitoring the disease progression or for evaluating the effect of the treatment. Reduction of the Quiescin Q6 level as compared to the risk level indicates that the condition of the patient is improving.

Non-limiting examples of such semi-quantitative tests known in the art, the principle of which could be used for the home test device according to the present invention are the HIV/AIDS test or Prostate Cancer tests sold by Sanitoets. The home prostate test is a rapid test intended as an initial semi-quantitative test to detect PSA blood levels higher than 4 ng/ml in whole blood. The typical home self-test kit comprises the following components: a test device to which the blood sample is to be administered and which results in a signal when the protein level is above a certain threshold level, an amount of diluent e.g. in dropper pipette to help the transfer of the analytes (i.e. the protein of interest) from the sample application zone to the signal detection zone, optionally an empty pipette for blood specimen collection, a finger pricking device, optionally a sterile swab to clean the area of pricking and instructions of use of the kit.

Similar tests are also known for e.g. breast cancer detection and CRP-protein level detection in view of cardiac risk home tests. The latter test encompasses the sending of the test result to a laboratory, where the result is interpreted by a technical or medical expert. Such telephone or internet based diagnosis of the patient's condition is of course possible and advisable with most of the kits, since interpretation of the test result is often more important than conducting the test. When using an electronic device as mentioned above which gives a numerical value of the level of protein present in the sample, this value can of course easily be communicated through telephone, mobile telephone, satellite phone, E-mail, internet or other communication means, warning a hospital, a medicinal practitioner or a first aid team that a person is suffering from an acute heart failure. A non-limiting example of such a system is disclosed in U.S. Pat. No. 6,482,156.

Reference is made in the description below to the drawings which exemplify particular embodiments of the invention; they are not at all intended to be limiting. The skilled person may adapt the device and substituent components and features according to the common practices of the person skilled in the art.

FIGS. 14A and B shows a preferred embodiment of a test strip of the invention. The strip (1) includes a proximal end (2) and a distal end (3). A sample application zone (4) is provided in the proximal end (2), a reaction zone (5) is adjacent thereto and a detection zone (6) is in the vicinity of the distal end (3). A sample may be deposited onto the solid support (7) at the application zone (4) to transfer by capillary action to the detection zone (6). A protective layer (8) that covers either or both the surfaces of the solid support (7), except for a region of the sample application zone (4) may be provided. Such protective layer protects the sample and chemical constituency of the strip from contamination and evaporation. One or more absorbent pads (9) in capillary contact with the sample application zone (4) of the solid support (7) may absorb and release sample as necessary; such pad (9) is typically placed on the surface of the solid support (7) that is the same or opposing the sample application zone (4). In FIG. 14B, the absorbent pad (9) is part of the sample application zone (4). One or more other absorbent pads (9') in capillary may be placed in contact with the detection zone (6) of the solid support (7), distal to any capture bands (11), (14). These pads (9') may absorb fluid that has passed through the solid support; such pad (9') is typically placed on the surface of the solid support (7) that is the same or opposing the sample application zone (4). The solid support (7) may made from any suitable material that has a capillary action property, and may have the same properties as described above. It should also be capable of supporting a substance (e.g. non-immobilised Quiescin Q6 binding molecule), which, when hydrated, can migrate across the solid support by a capillary action fluid flow.

The solid support (7) may also comprise a band of Quiescin Q6 binding molecule conjugate (10), located in the reaction zone (5), at a position distal to the sample application zone (4). Any Quiescin Q6 in the sample is carried by capillary action towards this band (10), where it reacts with the permanently immobilised Quiescin Q6 binding molecule conjugate.

The Quiescin Q6 binding molecule conjugate may be associated with or attached to a detection agent to facilitate detection. Examples of lab detection agents include, but are not limited to, luminescent labels; colorimetric labels, such as dyes; fluorescent labels; or chemical labels, such as electroactive agents (e.g., ferrocyanide); enzymes; radioactive labels; or radiofrequency labels. More commonly, the detection agent is a particle. Examples of particles useful in the practice of the invention include, but are not limited to, colloidal gold particles; colloidal sulphur particles; colloidal selenium particles; colloidal barium sulfate particles; colloidal iron sulfate particles; metal iodate particles; silver halide particles; silica particles; colloidal metal (hydrous) oxide particles; colloidal metal sulfide particles; colloidal lead selenide particles; colloidal cadmium selenide particles; colloidal metal phosphate particles; colloidal metal ferrite particles; any of the above-mentioned colloidal particles coated with organic or inorganic layers; protein or peptide molecules; liposomes; or organic polymer latex particles, such as polystyrene latex beads. Preferable particles are colloidal gold particles. Colloidal gold may be made by any conventional means, such as the methods outlined in G. Frens, 1973 Nature Physical Science, 241:20 (1973). Alternative methods may be described in U.S. Pat. Nos. 5,578,577, 5,141,850; 4,775,636; 4,853,335; 4,859,612; 5,079,172; 5,202,267; 5,514,602; 5,616,467; 5,681,775.

The solid support (7) further comprises one or more capture bands (11) in the detection zone (6). A capture band comprises a population of Quiescin Q6 binding molecule permanently immobilised thereon. The Quiescin Q6: Quiescin Q6-binding molecule conjugate complex formed in the reaction zone (5) migrates towards the detection zone (6) where said band (11) captures migrating complex, and concentrates it, allowing it to be visualised either by eye, or using a machine reader. The Quiescin Q6 binding molecule present in the reaction zone (5) and in the detection zone (6) may reaction to the same part of Quiescin Q6 or may react to different parts of Quiescin Q6.

One or more controls bands (12) may be present on the solid support (7). For example, a non-immobilised peptide (12) might be present in the sample application zone (4), which peptide does not cross-react with any of bands of Quiescin Q6 binding molecule (13) or (14). As the sample is applied, it migrates towards the reaction zone (5), where an anti-peptide antibody conjugate is disposed (13), and where a complex peptide-antibody complex is formed. Said complex migrates towards the detection zone (6), where a capture band (14) of anti-peptide antibody is immobilised on the solid support, and which concentrates said complex enabling visualisation. The control capture band (14) is located separately from the Quiescin Q6 capture band (11), therefore, a positive reaction can be seen distinct from the detection reaction if the assay is working correctly.

A particular advantage of a control according to the invention is that they are internal controls—that is, the control against which the Quiescin Q6 measurement results may be compared is present on the individual solid support. Therefore, the controls according to the invention may be used to correct for variability in the solid support, for example. Such correction would be impractical with external controls that are based, for example, on a statistical sampling of supports. Additionally, lot-to-lot, and run-to-run, variations between different supports may be minimized by use of control binding agents and control agents according to the invention. Furthermore, the effects of non-specific binding may be reduced. All of these corrections would be difficult to accomplish using external, off-support, controls.

During the assay, Quiescin Q6 from the sample and the Quiescin Q6 binding molecule conjugate combine and concentrate on the solid support (7). This combination results in a concentration of compounds that may can be visualised above the background colour of the solid support (7). The compounds may be formed from a combination of above-mentioned compounds, including antibodies, detection agents, and other particles associated with the reaction and detection zones. Based on the particular assay being performed, the reaction and detection zones may be selectively implemented to achieve an appropriate dynamic range which may be linear or non-linear.

A solid support (7) for performing the assay may be housed within the cartridge (20) as shown, for example, in FIG. 15. The cartridge is preferably watertight against urine, except for one or more openings. The solid support (7) may be exposed through an opening (21) in the cartridge to provide an application zone (4) in proximal end (2), and another opening (22) to enable reading of detection zone (6) close to the distal end (3). Cartridge (20) may include a sensor code (23) for communicating with a reading device.

The presence and/or concentration of Quiescin Q6 in a sample can be measured by surface plasmon resonance (SPR) using a chip having Quiescin Q6 binding molecule immobilized thereon, fluorescence resonance energy transfer (FRET), bioluminescence resonance energy transfer (BRET), fluorescence quenching, fluorescence polarization measurement or other means known in the art. Any of the binding assays described can be used to determine the presence and/or concentration of Quiescin Q6 in a sample. To do so, Quiescin Q6 binding molecule is reacted with a sample, and the concentration of Quiescin Q6 is measured as appropriate for the binding assay being used. To validate and calibrate an assay, control reactions using different concentrations of standard Quiescin Q6 and/or Quiescin Q6 binding molecule can be performed. Where solid phase assays are employed, after incubation, a washing step is performed to remove unbound Quiescin Q6. Bound, Quiescin Q6 is measured as appropriate for the given label (e.g., scintillation counting, fluorescence, antibody-dye etc.). If a qualitative result is desired, controls and different concentrations may not be necessary. Of course, the roles of Quiescin Q6 and Quiescin Q6 binding molecule may be switched; the skilled person may adapt the method so Quiescin Q6 binding molecule is applied to sample, at various concentrations of sample.

A Quiescin Q6 binding molecule according to the invention is any substance that binds specifically to Quiescin Q6. Examples of a Quiescin Q6 binding molecule useful according to the present invention, includes, but is not limited to an antibody, a polypeptide, a peptide, a lipid, a carbohydrate, a nucleic acid, peptide-nucleic acid, small molecule, small organic molecule, or other drug candidate. A Quiescin Q6 binding molecule can be natural or synthetic compound, including, for example, synthetic small molecule, compound contained in extracts of animal, plant, bacterial or fungal cells, as well as conditioned medium from such cells. Alternatively, Quiescin Q6 binding molecule can be an engineered protein having binding sites for Quiescin Q6. According to an aspect of the invention, a Quiescin Q6 binding molecule binds specifically to Quiescin Q6 with an affinity better than $10^{-6}$ M. A suitable Quiescin Q6 binding molecule e can be determined from its binding with a standard sample of Quiescin Q6. Methods for determining the binding between Quiescin Q6 binding molecule and Quiescin Q6 are known in the art. As used herein, the term antibody includes, but is not limited to, polyclonal antibodies, monoclonal antibodies, humanised or chimeric antibodies, engineered antibodies, and biologically functional antibody fragments (e.g. scFv, nanobodies, Fv, etc) sufficient for binding of the antibody fragment to the protein. Such antibody may be commercially available antibody against Quiescin Q6, such as, for example, a mouse, rat, human or humanised monoclonal antibody.

According to one aspect of the invention, the Quiescin Q6 binding molecule is labelled with a tag that permits detection with another agent (e.g. with a probe binding partner). Such tags can be, for example, biotin, streptavidin, his-tag, myc tag, maltose, maltose binding protein or any other kind of tag known in the art that has a binding partner. Example of associations which can be utilised in the probe: binding partner arrangement may be any, and includes, for example biotin: streptavidin, his-tag: metal ion (e.g. $Ni^{2+}$), maltose: maltose binding protein.

In another embodiment, the invention provides a simple and accurate colorimetric reagent strip and method for measuring presence of Quiescin Q6 in a sample. More in particular, the present invention also relates to a device comprising a reagent strip. The present reagent strip comprises a solid support which is provided with at least one test pad for measuring the presence of Quiescin Q6 in a sample. Said test pad preferably comprises a carrier matrix incorporating a reagent composition capable of interacting with Quiescin Q6 to produce a measurable response, preferably a visually or instrumentally measurable response. The reagent strip may be manufactured in any size and shape, but in general the reagent strip is longer than wide. The solid support may be composed of any suitable material and is preferably made of firm or stiff material such as cellulose acetate, polyethylene terephthalate, polypropylene, polycarbonate or polystyrene. In general, the carrier matrix is an absorbent material that allows the urine sample to move, in response to capillary forces, through the carrier matrix to contact the reagent composition and produce a detectable or measurable color transition. The carrier matrix can be any substance capable of incorporating the chemical reagents required to perform the assay of interest, as long as the carrier matrix is substantially inert with respect to the chemical reagents, and is porous or absorbent relative to the soluble components of the liquid test sample. The expression "carrier matrix" refers to either bibulous or nonbibulous matrices that are insoluble in water and other physiological fluids and maintain their structural integrity when exposed to water and other physiological fluids. Suitable bibulous matrices include filter paper, sponge materials, cellulose, wood, woven and nonwoven fabrics and the like. Nonbibulous matrices include glass fiber, polymeric films, and preformed or microporous membranes. Other suitable carrier matrices include hydrophilic inorganic powders, such as silica gel, alumina, diatomaceous earth and the like; argillaceous substances; cloth; hydrophilic natural polymeric materials, particularly cellulose material, like cellulosic beads, and especially fibercontaining papers such as filter paper or chromatographic paper; synthetic or modified naturally-occurring polymers, such as crosslinked gelatin, cellulose acetate, polyvinyl chloride, polyacrylamide, cellulose, polyvinyl alcohol, polysulfones, polyesters, polyacrylates, polyurethanes, crosslinked dextran, agarose, and other such crosslinked and noncrosslinked water-insoluble hydrophilic polymers. Hydrophobic and nonabsorptive substances are not suitable for use as the carrier matrix of the present invention. The carrier matrix can be of different chemical compositions or a mixture of chemical compositions. The matrix also can vary in regards to smoothness and roughness combined with hardness and softness. However, in every instance, the carrier matrix comprises a hydrophilic or absorptive material. The carrier matrix is most advantageously constructed from bibulous filter paper or nonbibulous polymeric films. A preferred carrier matrix is a hydrophilic, bibulous matrix, including cellulosic materials, such as paper, and preferably filter paper or a nonbibulous matrix, including polymeric films, such as a polyurethane or a crosslinked gelatin. A reagent composition which produces a colorimetric change when reacted with Quiescin Q6 in a sample can be homogeneously incorporated into the carrier matrix, and the carrier matrix then holds the reagent composition homogeneously throughout the carrier matrix while maintaining carrier matrix penetrability by the predetermined component of the test sample. Examples of suitable reagent compositions may include for instance a Quiescin Q6 binding molecule in case of an antibody-based technique, or pH buffer in case of enzymatic detection. The reagent composition is preferably dried and stabilized onto a test pad adhered to at least one end of a solid support. The test pad onto which the reagent composition is absorbed and dried, is preferably made of a membrane material that shows minimal background color. Preferably, the test pad may be constructed of acid or base washed materials in order to minimize background color. In another embodiment the reagent composition which is dried onto the reagent strip further comprises wetting agents to reduce brittleness of the test pad. Non-limiting examples of preferred wetting agents include TritonX-100, Bioterg, glycerol, 0 Tween, and the like. The reagent composition can be applied to the reagent strip by any method known in the art. For example, the carrier matrix from which the test pads are made may be dipped into a solution of the reagent composition and dried according to techniques known in the art. A reagent strip according to the invention may be provided with multiple test pads to assay for more than one analyte in a urine sample. A reagent strip may be provided comprising a solid support provided with one or more test pads including test pads for measuring the presence of one or more analytes selected from the group comprising proteins such as AHF markers BNP, NT-pro-BNP or fragments thereof, blood, leukocytes, nitrite, glucose, ketones, creatinine, albumin, bilirubin, urobilinogen and/or a pH test pad, and/or a test pad for measuring specific gravity.

A possible embodiment of a reagent strip 101 according to the invention is depicted diagrammatically in FIG. 16 A-B. The strip 101 includes a proximal end 102 and a distal end 103. Various test pads 109, 109', 109" on which the reagent compositions are provided at the proximal end 102 on a solid support 107 of the reagent strip. The strip must be designed in such a way that it can be wetted with a sufficiently large amount of sample, optionally diluted by a physiological fluid improving the capillary flow of a viscous sample such as blood or saliva and the like.

A reagent strip as defined herein is used as follows. Briefly, one or more test pad areas of the reagent strip of the invention is dipped into a sample or a small amount of sample is applied to the reagent strip onto the test pad area(s). A color development which can be analyzed visually or by reflectometry occurs on the reagent strip within a short time, usually within 0.5 to 10 minutes. The change in color of the reagent area on the test pad upon reacting with Quiescin Q6 is preferably directly proportional to the concentration of Quiescin Q6 in the patient sample. The color intensity that develops on the test pad may be determined visually or by a reflectance-based reader, for example. Color development at the test pad area(s) is compared to a reference color or colors to determine an estimate of the amount of Quiescin Q6 present in the sample The color intensity that develops on the test pad is compared to at least one, and preferably at least two standard color shades that correspond to a range of Quiescin Q6 concentration determined by application of a correction factor.

The reagent strip may further comprises a fluorescent or infrared dye, applied either to the support strip or incorporated into a test pad, which ensures proper alignment of the reagent strip in an apparatus having a detection system for the detectable or measurable response.

In another embodiment, the invention also relates to a test pad for measuring the presence of Quiescin Q6 in a sample. Preferably said test pad comprises a carrier matrix incorporating a reagent composition capable of interacting with Quiescin Q6 to produce a measurable response, preferably a visually or instrumentally measurable response. In another preferred embodiment the invention provides a test pad according as define herein for use in on a reagent strip, preferably on a reagent strip as defined herein.

The specific-binding agents, peptides, polypeptides, proteins, biomarkers etc. in the present kits may be in various forms, e.g., lyophilised, free in solution or immobilised on a solid phase. They may be, e.g., provided in a multi-well plate or as an array or microarray, or they may be packaged separately and/or individually. The may be suitably labelled as taught herein. Said kits may be particularly suitable for performing the assay methods of the invention, such as, e.g., immunoassays, ELISA assays, mass spectrometry assays, and the like.

The above aspects and embodiments are further supported by the following non-limiting examples.

EXAMPLES

Example 1: MASSTERMIND Discovery Platform for Discovery of New Biomarkers for AHF MASSTERMIND Experimental Setup For biomarker discovery, we analysed the changes in protein expression using mass spectrometric detection of protein levels using our previously published COF-RADIC™ technology platform (substantially as described inter alia in WO 02/077016 and in Gevaert et al. 2003, Nat Biotechnol 21(5): 566-9).

All plasma samples were depleted for the most abundant proteins using commercially available affinity-based chromatographic columns (e.g. Agilent Technologies). Depletion efficiency of albumin and immunoglobulin G (IgG) was checked using Western Blot analysis. Samples were prepared for MASStermind analysis according to the standard N-terminal COFRADIC procedures. Samples and controls were differentially labelled by trypsin mediated incorporation of $^{18}O/^{16}O$ at the C-terminus of every tryptic peptide. After N-terminal peptide sorting, NanoLC separations followed by direct spotting onto MALDI targets were performed. MALDI-TOF/TOF instrumentation was used to generate MS spectra. The MS spectra were analyzed using in-house developed bioinformatics tools, such as tools for peak recognition and deisotoping, ratio determination between analyte and reference, clustering, inter-sample alignment and extensive sample quality control. Once all the samples were aligned and quality controlled, statistical analysis was initiated.

MASSTERMIND Statistical Analysis

To select for differential features (or peptides) that discriminate two populations, two different statistical measures were applied: one-rule classifier and Significance Analysis of Microarrays (SAM) analysis. Conceptually the simplest machine learning technique to find differential features is a one-rule classifier. In this method a simple rule of the form "If ratio<X then class=A else class=B" is generated for each feature. The performance of this rule on the data is determined by leave-one-out cross-validation. Features that show low error rates in this analysis are prime biomarker candidates. SAM (Tusher et al. 2001, PNAS 98: 5116-5121) is a method to select the most differential features, while controlling the False Discovery Rate (FDR). The method was originally developed for use in microarray experiments and proves applicable in Pronota's data matrices. The main advantage of this method over the one-rule classifier is that it will still allow to pick up useful trends when the difference in ratios between both classes start to diminish and random noise from the experiment starts to obscure the actual levels of the candidate markers. SAM calculates the relative difference in the ratio of features between two classes of samples. To estimate the significance of this score, a null distribution is estimated by permuting the class assignments of all samples and re-scoring. This gives us a confident estimation of the false discovery rat (FDR), that is the percentage of proteins or gene products that were identified by chance. To optimally account for missing values and intensity of the MS signal, the complete SAM analysis was run on different subsets of the data, using different cut-offs for these values. All results were compiled in a final report.

Example 2: MASSterclass Targeted Protein Quantitation for Early Validation of Candidate Markers Derived from Discovery MASSTERCLASS Experimental Setup MASSterclass assays use targeted tandem mass spectrometry with stable isotope dilution as an end-stage peptide quantitation system (also called Multiple Reaction Monitoring (MRM) and Single Reaction Monitoring (SRM)). The targeted peptide is specific (i.e., proteotypic) for the specific protein of interest. i.e., the amount of peptide measured is directly related to the amount of protein in the original sample. To reach the specificity and sensitivity needed for biomarker quantitation in complex samples, peptide fractionations precede the end-stage quantitation step.

A suitable MASSTERCLASS assay may include the following steps:

Plasma/serum sample

Depletion of human albumin and IgG (complexity reduction on protein level) using affinity capture with anti-albumin and anti-IgG antibodies using ProteoPrep spin columns (Sigma Aldrich)

Spiking of known amounts of isotopically labelled peptides. This peptide has the same amino acid sequence as the proteotypic peptide of interest, typically with one isotopically labelled amino acid built in to generate a mass difference. During the entire process, the labelled peptide has identical chemical and chromatographic behaviour as the endogenous peptide, except during the end-stage quantitation step which is based on molecular mass.

Tryptic digest. The proteins in the depleted serum/plasma sample are digested into peptides using trypsin. This enzyme cleaves proteins C-terminally from lysine and argninine, except when a proline is present C-terminally of the lysine or arginine. Before digestion, proteins are denatured by boiling, which renders the protein molecule more accessible for the trypsin activity during the 16 h incubation at 37° C.

First peptide-based fractionation: Free Flow Electrophoresis (FFE; BD Diagnostic) is a gel-free, fluid separation technique in which charged molecules moving in a continuous laminar flow are separated through an electrical field perpendicular to the flow. The electrical field causes the charged molecules to separate in the pH gradient according to their isoelectric point (pI). Only those fractions containing the monitored peptides are selected for further fractionation and LC-MS/MS analysis. Each peptide of interest elutes from the FFE chamber at a specific fraction number, which is determined during protein assay development using the synthetic peptide homologue. Specific fractions or fraction pools (multiplexing) proceed to the next level of fractionation.

Second peptide-based fractionation: Phenyl HPLC (XBridge Phenyl; Waters) separates peptides according to hydrophobicity and aromatic nature of amino acids present in the peptide sequence. Orthogonality with the back-end C18 separation is achieved by operating the column at an increased pH value (pH 10). As demonstrated by Gilar et al. 2005, *J Sep Sci* 28(14): 1694-1703), pH is by far the most drastic parameter to alter peptide selectivity in RP-HPLC. Each peptide of interest elutes from the Phenyl column at a specific retention time, which is determined during protein assay development using the synthetic peptide homologue. The use of an external control system, in which a mixture of 9 standard peptides is separated upfront a batch of sample separations, allows adjusting the fraction collection in order to correct for retention time shifts. The extent of fractionation is dependent on the concentration of the protein in the sample and the complexity of that sample.

LC-MS/MS based quantitation, including further separation on reversed phase (C18) nanoLC (PepMap C18; Dionex) and MS/MS: tandem mass spectrometry using MRM (4000 QTRAP; ABI)/SRM (Vantage TSQ; Thermo Scientific) mode. The LC column is connected to an electrospray needle connected to the source head of the mass spectrometer. As material elutes from the column, molecules are ionized and enter the mass spectrometer in the gas phase. The peptide that is monitored is specifically selected to pass the first quadrupole (Q1), based on its mass to charge ratio (m/z). The selected peptide is then fragmented in a second quadrupole (Q2) which is used as a collision cell. The resulting fragments then enter the third quadrupole (Q3). Depending on the instrument settings (determined during the assay development phase) only a specific peptide fragment or specific peptide fragments (or so called transitions) are selected for detection.

The combination of the m/z of the monitored peptide and the m/z of the monitored fragment of this peptide is called a transition. This process can be performed for multiple transitions during one experiment. Both the endogenous peptide (analyte) and its corresponding isotopically labelled synthetic peptide (internal standard) elute at the same retention time, and are measured in the same LC-MS/MS experiment.

The MASSterclass readout is defined by the ratio between the area under the peak specific for the analyte and the area under the peak specific for the synthetic isotopically labelled analogue (internal standard). MASSterclass readouts are directly related to the original concentration of the protein in the sample. MASSterclass readouts can therefore be compared between different samples and groups of samples.

A typical MASSTERCLASS protocol followed in the present study is given here below:

25 μL of plasma is subjected to a depletion of human albumin and IgG (ProteoPrep spin columns; Sigma Aldrich) according to the manufacturer's protocol, except that 20 mM NH$_4$HCO$_3$ was used as the binding/equilibration buffer.

The depleted sample (225 μL) is denatured for 15 min at 95° C. and immediately cooled on ice 500 fmol of the isotopically labelled peptide (custom made 'Heavy AQUA' peptide; Thermo Scientific) is spiked in the sample 20 μg trypsin is added to the sample and digestion is allowed for 16 h at 37° C.

The digested sample was first diluted ⅛ in solvent A (0.1% formic acid) and then 1/20 in the same solvent containing 250 amol/μL of all isotopically labelled peptides (custom made 'Heavy AQUA' peptide; Thermo Scientific) of interest.

20 μL of the final dilution was separated using reverse-phase NanoLC with on-line MS/MS in MRM/SRM mode:

Column: PepMap C18, 75 μm I.D.×25 cm L, 100 Å pore diameter, 5 μm particle size

Solvent A: 0.1% formic acid

Solvent B: 80% acetonitrile, 0.1% formic acid

Gradient: 30 min; 2%-55% Solvent B

MS/MS in MRM mode: method contains the transitions for the analyte as well as for the synthetic, labelled peptide.

The used transitions were experimentally determined and selected during protein assay development Each of the transitions of interest was measured for a period starting 3 minutes before and ending 3 minutes after the determined retention time of the peptide of interest, making sure that each peak had at least 15 datapoints.

The raw data was analysed and quantified using the LCQuan software (Thermo Scientific): the area under the analyte (=the Quiescin Q6 peptide) peak and under the internal standard (the labelled, synthetic Quiescin Q6 peptide) peak at the same C18 retention time was determined by automatic peak detection. These were cross-checked manually.

The MASSterclass readout was defined by the ratio of the analyte peak area and the internal standard peak area MASSTERCLASS Statistical Analysis The measured ratios are differential quantitations of peptides. In other words a ratio is the normalised concentration of a peptide. The concentration of a peptide is proportional to the ratio measured in the mass spectrometer.

A statistical analysis is conducted in order to determine the diagnostic accuracy of a specific protein. To do so, sample classes are compared pairwise. The analysis defines the ability of a protein to discriminate two sample populations.

The diagnostic accuracy of a specific protein was determined by measuring the area under the Receiver-Operating-Characteristics (ROC) curves (AUC) (Sullivan Pepe M, The statistical evaluation of medical tests for classification and prediction. 1993 Oxford University Press New York). The estimated and confidence intervals for AUCs were also computed using a non-parametric approach, namely bootstrapping (Efron B, Tibshirani R J. Nonparametric confidence intervals. An introduction to the bootstrap. Monographs on statistics and applied probability. 1993; 57:75-90 Chapman & Hall New York). Dependencies of marker levels to clinical variables and disease backgrounds were analyzed using Chi-Square tests and Wilcoxon sum rank test (Cleophas T. J., et al, 2006, Statistics Applied to Clinical Trials, Springer).

Example 3: Unbiased Discovery of Novel AHF Markers Using MASStermind

The MASStermind proteomic discovery platform was used to discover novel low abundance AHF protein biomarker candidates directly in patient plasma. Serial plasma samples collected prospectively from 10 patients with AHF on admission to the emergency department and just prior to their discharge from hospital were analyzed alongside age and gender matched control samples collected from healthy individuals (FIG. 4). Comparing protein profiles of AHF patients at admission versus at discharge yields biomarker candidates for treatment monitoring and discharge decisions while a comparison of AHF patients with healthy matched controls provides with new biomarker candidates for improving diagnostic accuracy.

Figure 5:
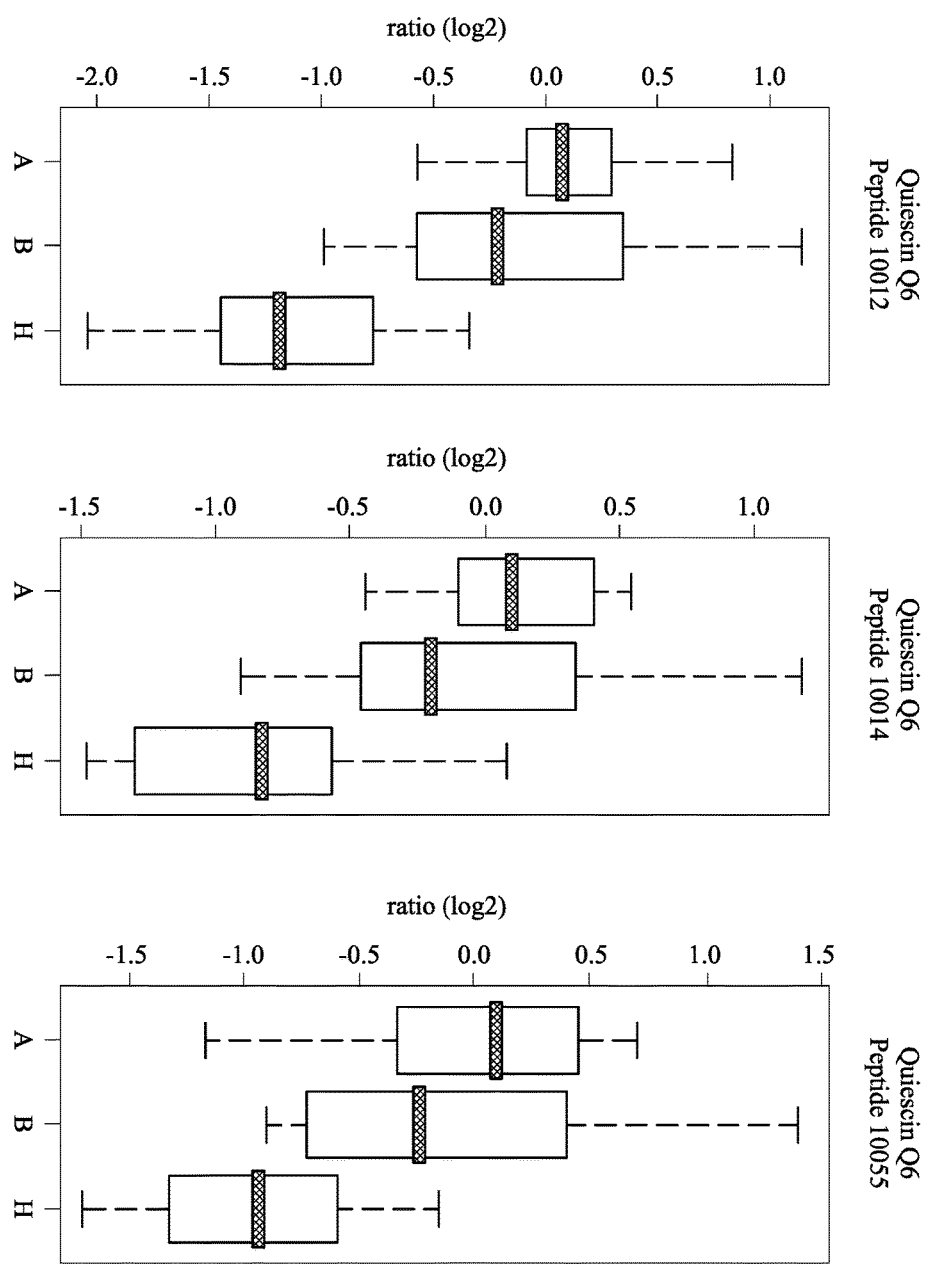
FIG. 5 shows MASStermind discovery results for Quiescin Q6. Boxplots show the relative peptide levels measured according to the MASStermind reference for the 3 analyzed populations for 3 different Quiescin Q6 specific peptides detected using MASStermind.

Following the MASStermind procedure differential features that discriminate AHF and healthy populations and/or admission and discharge samples were selected by different statistical measures (SAM and one-rule classifier). Over 100 proteins were identified showing a consistent change in levels between the three groups, of which ~60% fall outside the window of classical plasma proteins. Quiescin Q6 was selected based on high SAM and one-rule classifier scores for the AHF—healthy comparison. Three different peptides of Quiescin Q6 were identified, all showing the same trend: higher levels in AHF patients, at admission and discharge and lower levels in healthy control subjects (see FIG. 5). Median fold differences are between 1.5 and 2-fold for all peptides.

The three specific Quiescin Q6 peptides are all localized in the N-terminal extracellular region of the protein, and hence can correspond to both Quiescin isoforms (FIGS. 1 and 2).

Example 4: Verification of Diagnostic Value of Candidate Marker Quiescin Q6 Using MASSterclass 4A: Clinical samples were collected prospectively across 3 different medical centres from 4 different populations:
Patients presenting to emergency department (ED) with dyspnea related to acute heart failure, with sampling at admission (A) and just prior to discharge from the hospital (B)
Patients presenting to ED with dyspnea unrelated to acute heart failure (D)
Stable chronic heart failure patients (C)
Age and gender matched healthy volunteers (H)
For all included patients a comprehensive case report file (CRF) was completed with details on medical background, admission diagnosis and medications.

Figure 6:
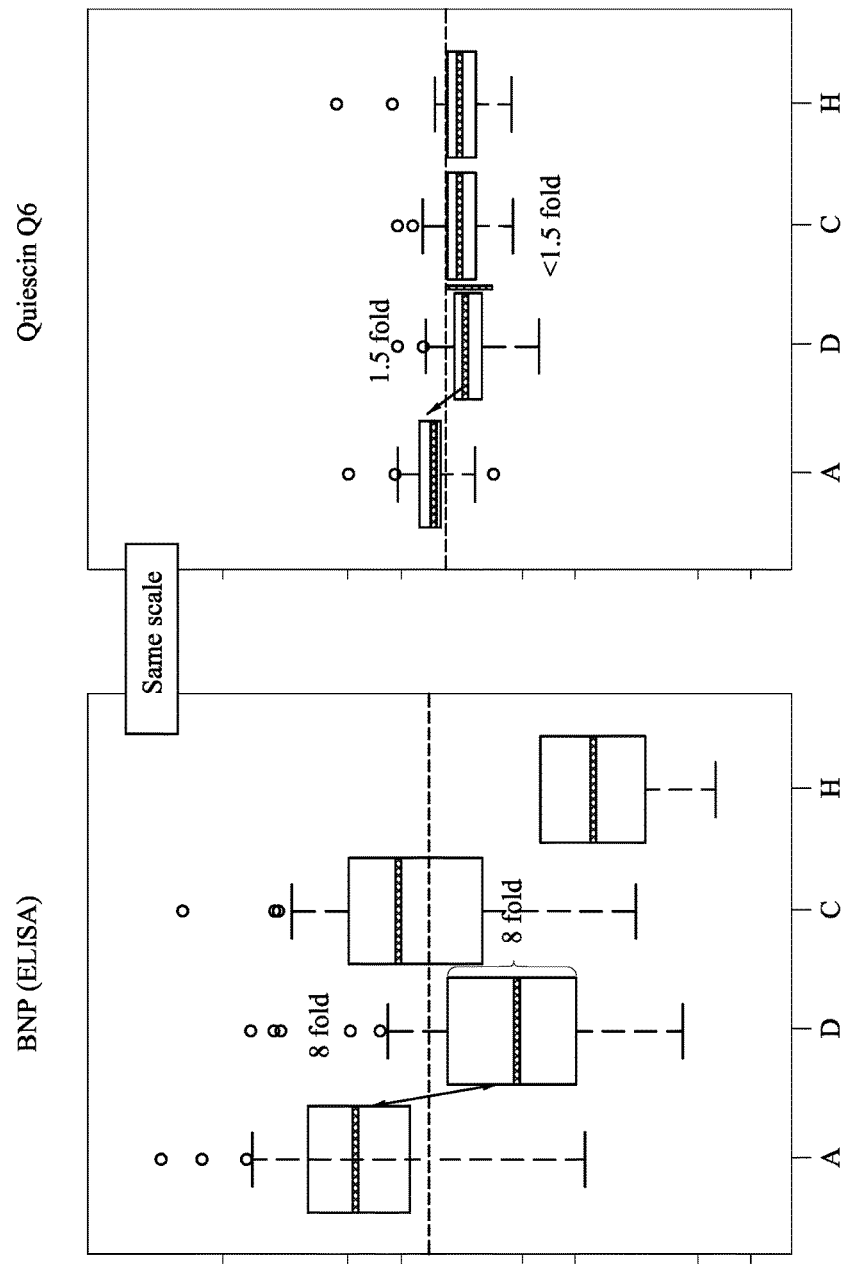
FIG. 6 shows absolute levels of BNP as measured by ELISA in populations A, C, D and H (left panel), and corresponding MASSterclass quantitation of Quiescin Q6 pept110 (right panel).

FIG. 6 illustrates relative levels of Quiescin Q6 as measured by MASSterclass in 40 samples of each population. For the diagnostic question the levels at discharge of AHF patients are less relevant and are therefore excluded for the remaining analysis. Median Quiescin Q6 levels among patients with AHF were 1.5 fold higher than dyspneic patients without AHF. The interquartile range, representing 50% of the samples, in all patients populations is less than 1.5 fold. In contrast the median fold difference for BNP between AHF and D patients is much larger, up to 8 fold, but also the interquartile range is 8-fold in these populations. Strikingly, the levels of Quiescin Q6 in D patients are very much comparable to levels in stable CHF patients and healthy controls, while for BNP there is no significant difference between AHF and CHF patients.

Figure 7B:
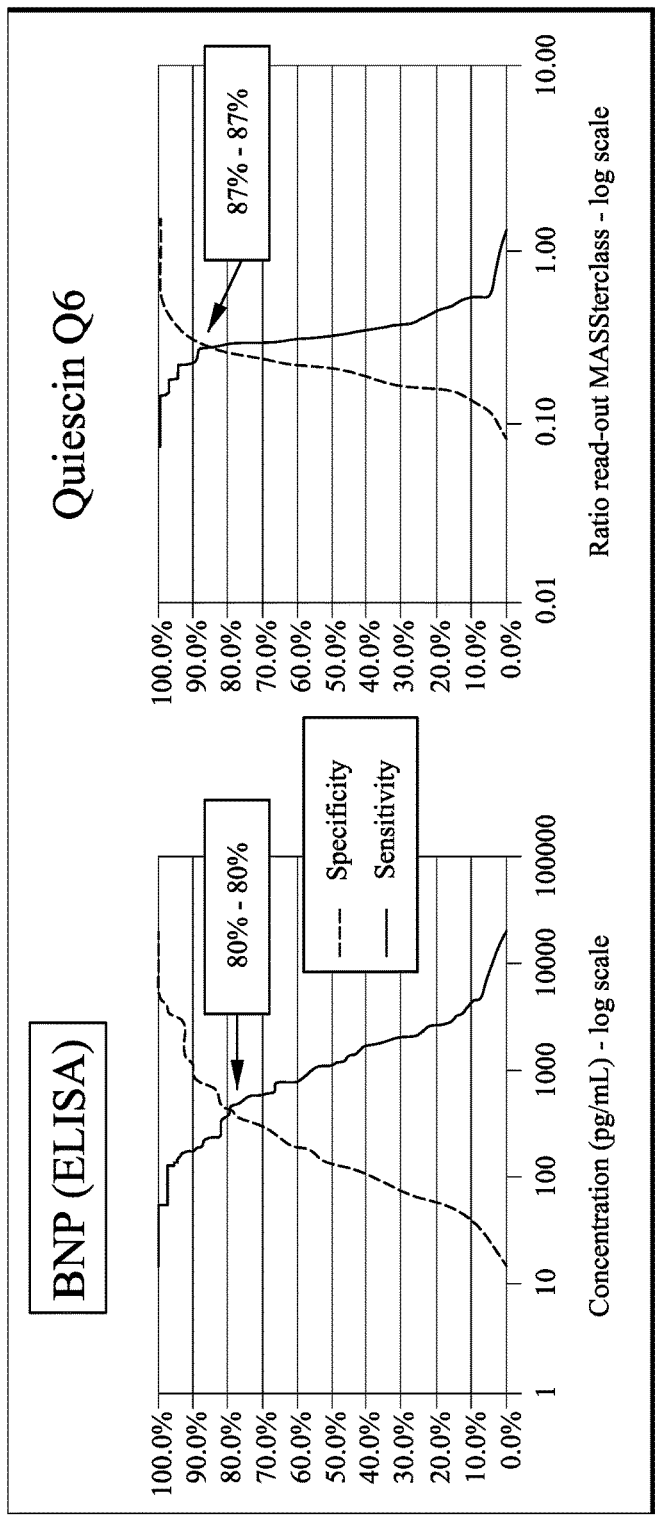

Receiver-operating characteristics (ROC) analysis demonstrated Quiescin Q6 to be highly sensitive and specific for diagnosing AHF in dyspneic patients presenting to the ED, as indicated by an overall median AUC of 0.89 with 95% CI 0.79-0.96 (FIG. 7A). Compared to the B-type natriuretic peptides this is an improvement of 5-9%, where BNP performs slightly better than NT-proBNP. At a single ratio or concentration cut-off point where sensitivity equals specificity, Quiescin Q6 has calculated sensitivity and specificity of 87%, an increase of 7% to rule in AHF compared to BNP. The accuracy plots demonstrate that for a given sensitivity up to 95%, Quiescin Q6 gives higher specificities compared to BNP (FIG. 7B).

Figure 8:
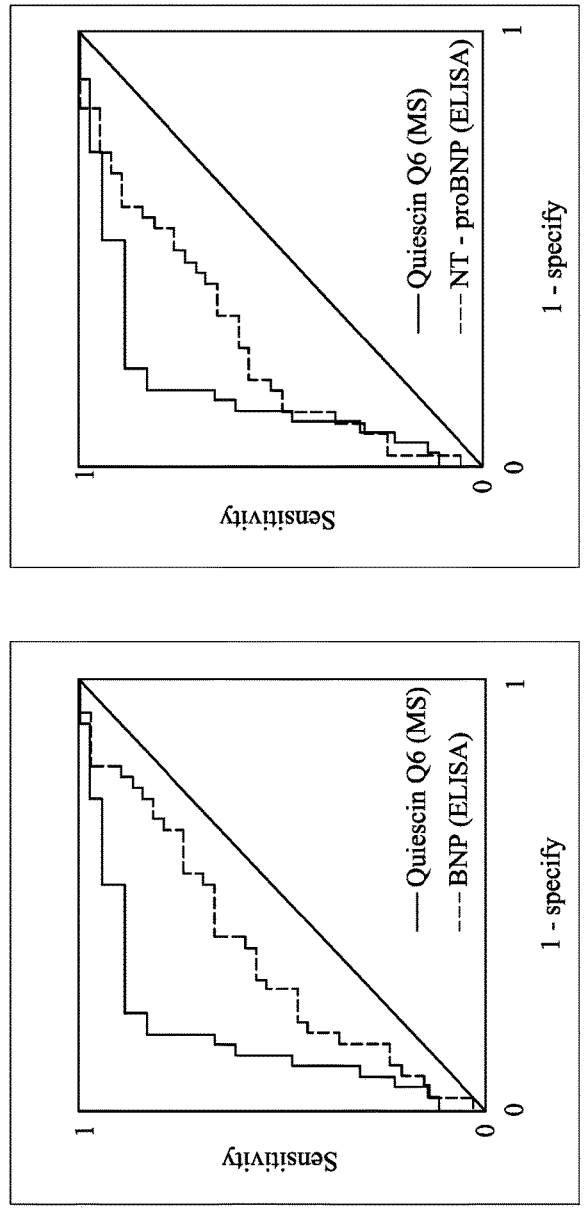
FIG. 8 shows ROC curve of BNP compared to Quiescin Q6 and NT-proBNP compared to Quiescin Q6 respectively for discriminating acute decompensated heart failure from chronic stable heart failure patients.

Boxplots in FIG. 6 show that BNP is a marker for heart failure rather than a marker for acute heart failure, consistent with data from literature. This constitutes a significant problem for emergency diagnosis of AHF, as BNP levels are already raised in patients with a HF background. In contrast Quiescin Q6 does show a significant and consistent difference between AHF versus stable CHF patients; levels in CHF patients are comparable to levels in healthy subjects. ROC curve analysis hence also demonstrates far superior performance of Quiescin Q6 in discriminating AHF patients from stable chronic heart failure patients: median AUC: 0.83 compared to 0.65 for BNP (FIG. 8). Hence Quiescin Q6 is a specific marker of an acute heart failure event, independently from underlying heart failure history.

4B: The above experiment was extended with samples collected under the same protocol and inclusion criteria. In total there is 147 samples from patients presenting to emergency department (ED) with acute dyspnea either related to acute heart failure or related to other causes (=dyspnea non AHF). Samples from stable chronic heart failure patients (CHF; n=80) were collected from an outpatient setting.

For all included patients a comprehensive case report file (CRF) was completed with details on medical background, admission diagnosis and medications (Table 1).

TABLE 1

| Patient Characteristics: | | AHF (n = 76) | Dyspnea nonAHF (n = 71) | Stable CHF (n = 80) |
|---|---|---|---|---|
| Age (av) | | 72 ± 12 | 62 ± 19 | 61 ± 12 |
| Gender | Mates % | 67 | 64 | 79 |
| Medical | HF history % | 70 | 8.5 | 100 |
| history | COPD/Asthma % | 14.5 | 20 | 4 |
| | Coronary artery disease % | 30 | 4 | 34 |
| Physical | Heart Rate (bpm) | 84 (68-107) | 92 (75-114) | 70 (60-78) |
| examination | Systolic bp (mmHg) | 135 (107-161) | 130 (106-145) | 111 (104-125) |
| | Diastolic bp (mmHg) | 74 (61-87) | 70 (61-80) | 70 (60-75) |
| ECG | LVEF -median (interquartile range) | 35 (25-51) | 65 (59-65) | 30 (25-40) |
| Admission | BNP (pg/ml) | 1006 (470-2027) | 119.4 (57-297) | 355 (146-791) |
| labs | NT-proBNP (pg/ml) | 5591 (2453-11500) | 670 (289-1939) | 1295 (552-3435) |
| | Creatinine (umol/l) | 123.2 (89.5-161.5) | 79 (65-107.5) | 101 (88-145) |

Figure 9:
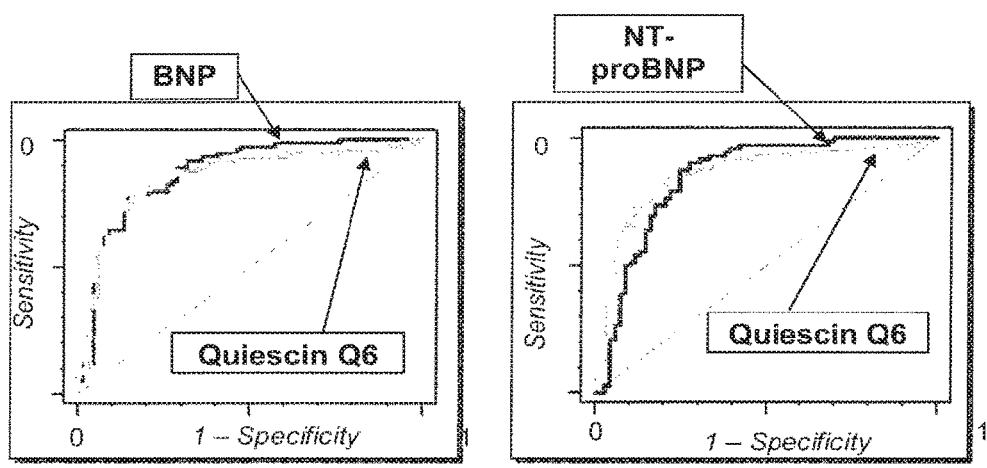
FIG. 9 illustrates that Quiescin Q6 shows comparable performance to B-type natriuretic peptides in discriminating AHF from dyspneic non-acute heart failure patients. (A) Receiver operating characteristic curve of BNP compared to Quiescin Q6 and NT-proBNP compared to (B) Quiescin Q6 respectively for diagnosis of heart failure cause of dyspnea in the ED. Calculated median area under the curve (AUC) and 95% confidence intervals are given in Table 2 below.

Receiver-operating characteristics (ROC) analysis demonstrated Quiescin Q6 to be highly sensitive and specific for diagnosing AHF in dyspneic patients presenting to the ED, as indicated by an overall median AUC of 0.86 with 95% CI 0.79-0.92 (FIG. 9). The actual results are given in Table 2. This diagnostic performance is equivalent to BNP and NT-proBNP, the current gold standard biomarkers for diagnosing AHF in an acute dyspnea population. At a single ratio or concentration cut-off Quiescin Q6 reaches a diagnostic accuracy of 82% while BNP at its rule-out cut-off (100 pg/mL) has an accuracy of 73%.

TABLE 2

| | BNP | NT-proBNP | Quiescin Q6 |
|---|---|---|---|
| Median AUC | 0.88 | 0.85 | 0.86 |
| 95% CI | 0.81-0.93 | 0.78-0.91 | 0.79-0.92 |

Figure 10:
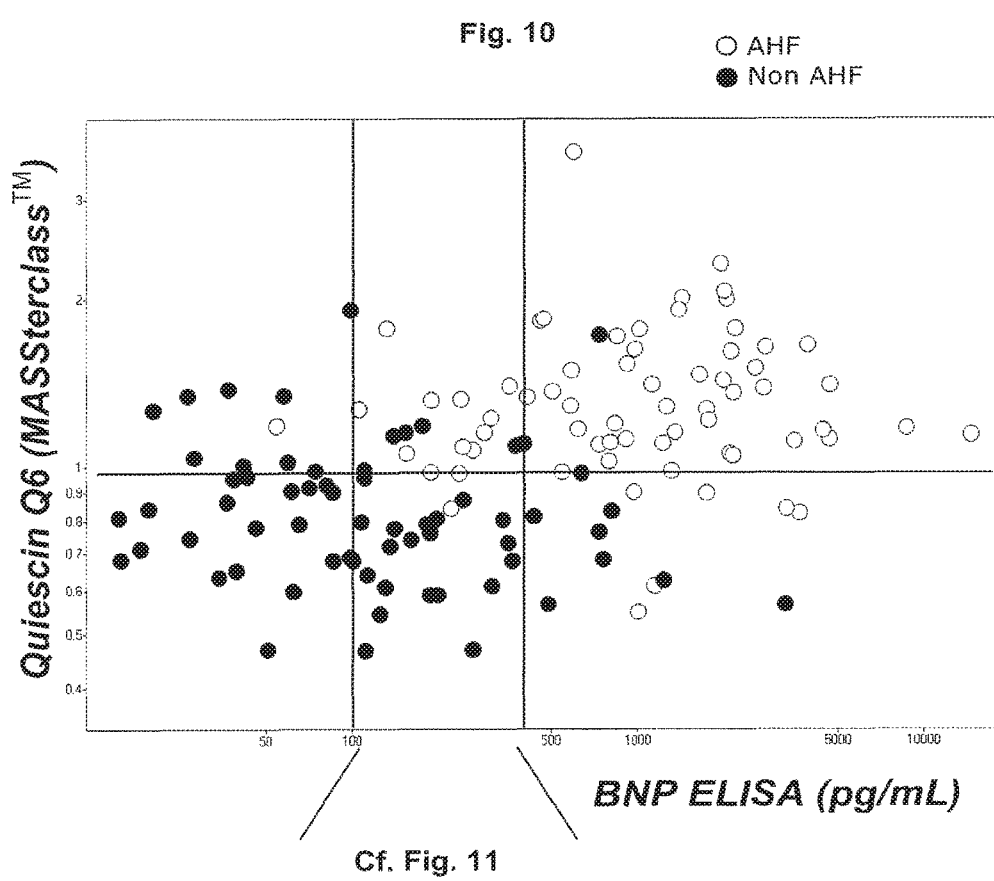
FIG. 10 illustrates the impact of combining Quiescin Q6 and BNP markers on the diagnostic accuracy. BNP levels measured by standard ELISA are shown in the X-axis and Quiescin Q6 levels as measured by MASSterclass are depicted in the Y-axis. The calculated best cut-off for Quiescin Q6 (horizontal line) and the routinely used cut-offs for BNP (two vertical lines encompassing the "grey zone") are also shown. Calculated accuracy for the independent markers and the combination of both markers are given in Table 3 below.
Figure 11:
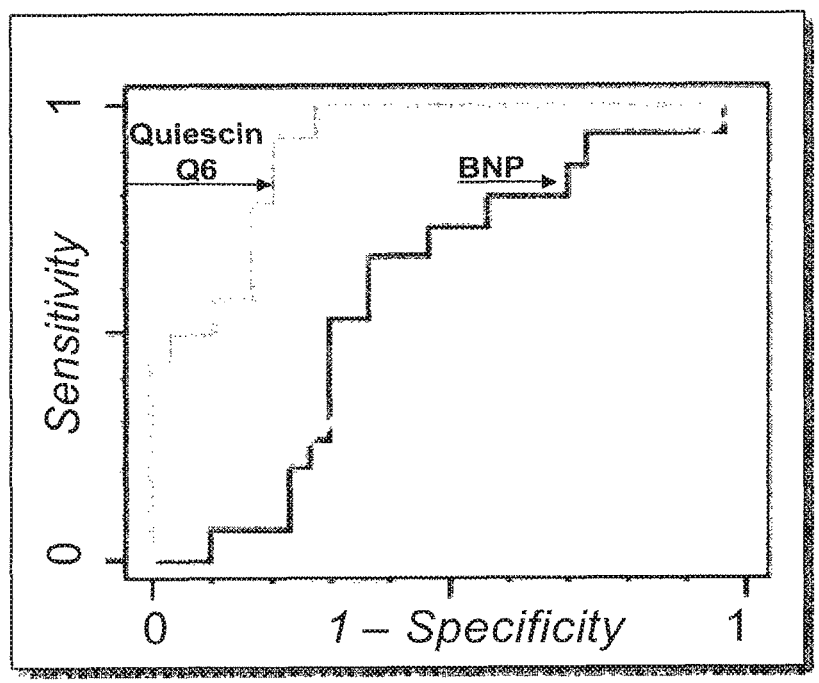
FIG. 11 shows the diagnostic performance of Quiescin Q6 in the BNP diagnostic grey zone. The calculated median AUC and 95% confidence intervals for patients with BNP levels between 100-400 pg/mL are illustrated.

Combining Quiescin Q6 to BNP has a significant impact on the diagnostic accuracy, reaching a maximum of 88% in the current dataset (FIG. 10). The diagnostic accuracy of Quiescin Q6 and BNP at a single cut-off and the combination of the two markers is summarized in Table 3 below. The power of the Quiescin Q6—BNP combination results from their complementarity and more specifically the high accuracy of Quiescin Q6 in the BNP diagnostic grey zone. Between 100 pg/mL and 400 pg/mL BNP is said not to have any diagnostic value for dyspneic patients. This is also illustrated in this dataset: for those patients BNP has a median AUC of 0.58 with 95% CI 0.42-0.75 while Quiescin Q6 reaches a median AUC of 0.91 (0.8-0.97) (FIG. 11).

TABLE 3

| Accuracy BNP at 100 pg/mL = | 73% |
|---|---|
| Accuracy Quiescin Q6 = | 82% |
| Accuracy BNP (rule-out) + Quiescin Q6 = | 88% |

Example 5: Influence of Clinical Variables and Disease Background on Quiescin Q6 Marker Levels To have a viable new AHF diagnostic tool, it is key to show added value over the currently used standard biomarkers on top of a good overall diagnostic performance. Several factors such as gender, age, body mass index, renal function, history of heart failure and history of other cardiac disease have been shown to affect levels of circulating natriuretic peptides. Therefore a marker independent of the parameters mentioned above will have incremental value in the rapid diagnosis of AHF. This dataset of 150 dyspnea patients and 80 stable CHF patients allows a first insight into the dependency of Quiescin Q6 to different clinical parameters.

Influence of clinical variables and disease backgrounds on Quiescin Q6 and (NT-pro)BNP levels were analyzed using Chi-square statistics and Wilcoxon sum rank tests. Age, renal failure (based on creatinin levels), left ventricular ejection fraction, admission diagnosis, history of heart failure and coronary artery disease and COPD/asthma co-morbidities, all known to impact natriuretic peptide levels were looked at. Table 4 summarizes the most important associations of Quiescin Q6 and (NT-pro)BNP. No significant association of Quiescin Q6 to any of the listed parameters can be detected, other than the diagnosis of AHF/no-AHF in the dyspnea population. This implies that Quiescin Q6 levels are not influenced by any parameter other than acute decompensation of the heart in the current dataset.

FIG. 12 shows Quiescin Q6 levels are independent of renal failure while BNP and NT-proBNP are clearly elevated in patients with increased creatinin levels. As renal failure is a frequent co-morbidity of heart failure, independence of Quiescin Q6 levels to creatinin levels is an important feature and will have a major impact on the diagnostic performance.

Figure 13A:
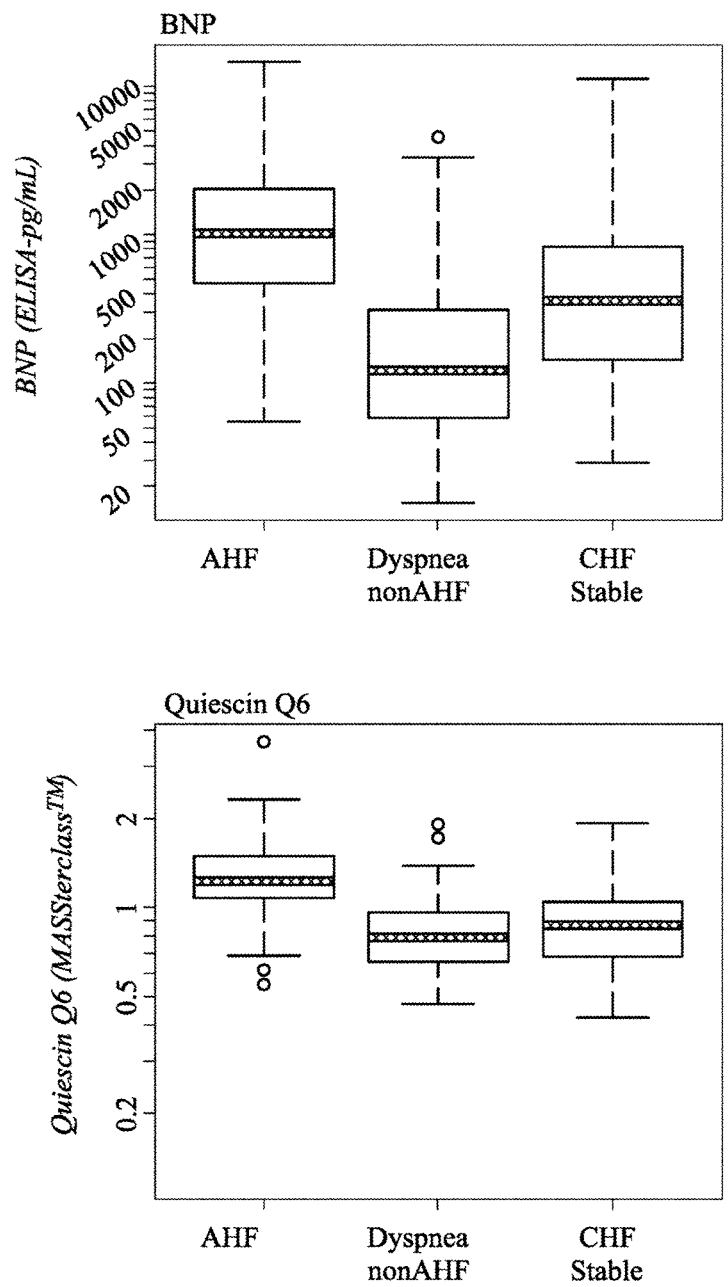
FIG. 13A shows levels for BNP as measured by ELISA and for Quiescin Q6 as measured by MASSterclass in the AHF, dyspnea nonAHF and CHF populations (A).
Figure 13B:
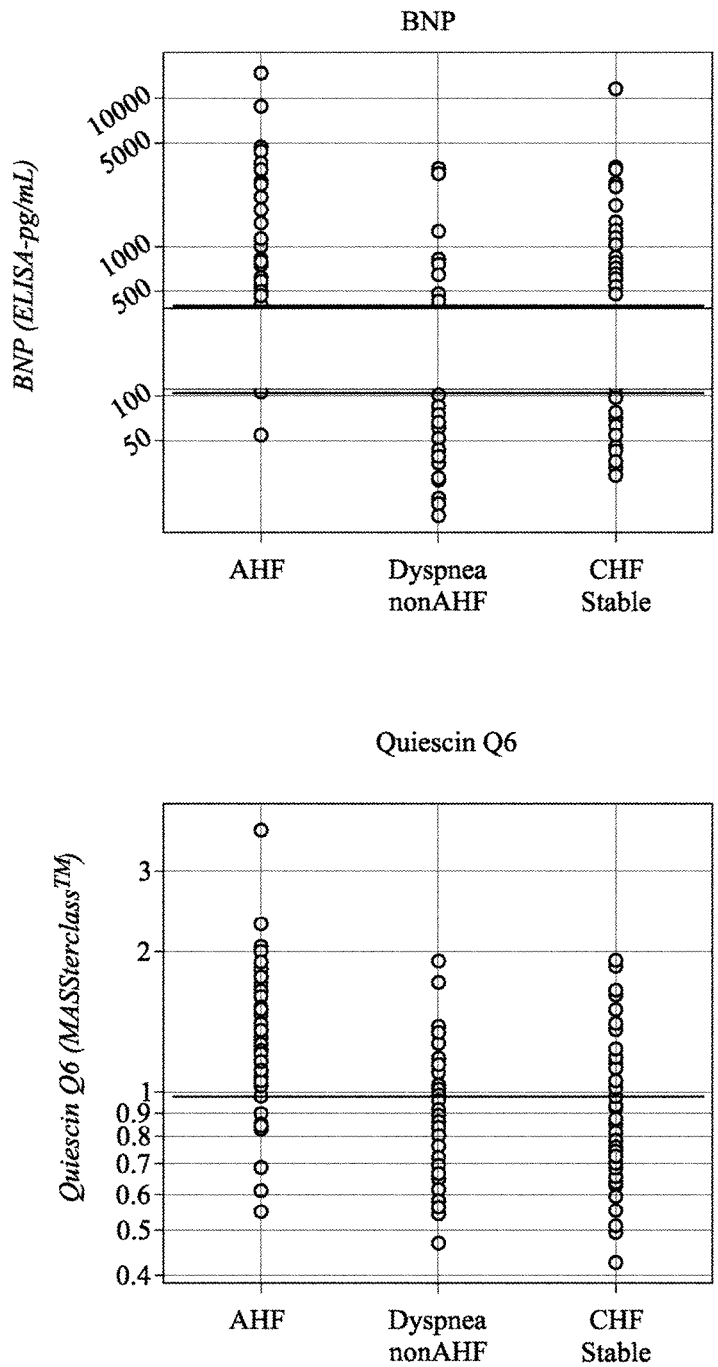
FIG. 13B illustrates the same data by presented in a scatter plot. The calculated best cut-off for Quiescin Q6 and the routinely used cut-offs for BNP are also shown. It is clear that, unlike for BNP which is elevated also in CHF patients, the Quiescin Q6 level is only elevated (1.5 fold) in AHF patients.

FIG. 13 illustrates relative levels of Quiescin Q6 as measured by MASSterclass in the AHF, dyspnea non-AHF and stable CHF populations. Median Quiescin Q6 levels among patients with AHF were 1.5 fold higher than dyspneic patients without AHF. Strikingly, the levels of Quiescin Q6 in dyspnea non AHF patients are very much comparable to levels in stable CHF patients, while baseline levels for BNP are elevated in stable CHF patients.

TABLE 4

| Clinical feature | Population | Quiescin Q6 | BNP | NT-proBNP | comments |
|---|---|---|---|---|---|
| Diagnosis | all dyspnea | $6 \times 10^{-14}$ | $7 \times 10^{-15}$ | $7 \times 10^{-13}$ | |
| LVEF | AHF/CHF | 0.66 | <0.01 | <0.05 | |
| Creatinin | CHF | 0.31 | <0.05 | <0.001 | |
| Admission diagnosis | Dyspnea non AHF | 0.22 | <0.01 | <0.001 | Increased levels in pneumonia pts |
| Plasma sodium | CHF/dyspnea non AHF | 0.16 | <0.01 | <0.01 | |

---

What is claimed is:

1. A method for determining quantity of Quiescin Q6 in a sample from a subject, wherein the subject presents with dyspnea has a medical history of heart failure, or has a prophylactic or therapeutic treatment of acute heart failure (AHF), the method comprising the steps:
   (i) obtaining a sample from the subject; and
   (ii) determining the quantity of Quiescin Q6 by contacting the sample with one or more binding agents capable of specifically binding to Quiescin Q6.

2. The method according to claim 1, wherein the method further comprises measuring the presence or absence and/or quantity of one or more other biomarkers selected from the group consisting of B-type natriuretic peptide (BNP), pro-B-type natriuretic peptide (proBNP), and amino terminal pro-B-type natriuretic peptide (NTproBNP).

3. The method according to claim 2, further comprising the steps of:
   (i) establishing a subject profile based on the quantity of Quiescin Q6 and the presence or absence and/or quantity of said one or more other biomarkers.

4. The method according to claim 3, wherein the presence or absence and/or quantity of the one or more other biomarkers is measured using a binding agent capable of specifically binding to said one or more other biomarkers in the conducted assay.

5. The method according to claim 1, wherein the subject is human.

6. The method according to claim 1, wherein the subject is part of a population of patients showing signs of dyspnea, caused by AHF, chronic obstructive pulmonary disease (COPD), or pneumonia, or of patients that suffer from heart failure co-morbidities including diabetes, coronary artery disease, asthma, COPD and/or chronic renal disease.

7. The method according to claim 2, wherein the quantity of Quiescin Q6 and/or the presence or absence and/or quantity of the one or more other biomarkers in the conducted assay is measured using an immunoassay technology selected from the group consisting of direct ELISA, indirect ELISA, sandwich ELISA, competitive ELISA, multiplex ELISA, radioimmunoassay (RIA) and ELISPOT technologies, or using a mass spectrometry analysis method or using a chromatography method, or using a combination of said methods.

8. The method according to claim 1, wherein said sample is a plasma sample.

9. The method according to claim 1, wherein the quantity of Quiescin Q6 determined is the quantity of circulating Quiescin Q6 protein.

10. The method according to claim 1, wherein said one or more binding agents capable of specifically binding to Quiescin Q6 is an antibody, aptamer, photoaptamer, protein, peptide, peptidomimetic or a small molecule.

11. The method according to claim 1, wherein said one or more binding agents is immobilized on a solid phase or support.

12. The method according to claim 1, wherein the method further comprises comparing the quantity of Quiescin Q6 measured in said sample with a reference value of the quantity of Quiescin Q6.

* * * * *

UNITED STATES PATENT AND TRADEMARK OFFICE
CERTIFICATE OF CORRECTION

PATENT NO. : 10,114,021 B2
APPLICATION NO. : 15/242044
DATED : October 30, 2018
INVENTOR(S) : Koen Kas Page 1 of 1

It is certified that error appears in the above-identified patent and that said Letters Patent is hereby corrected as shown below:

In the Specification

Column 22, Line 32, "$^{13}O$," should be --$^{13}C$,--.

Column 22, Line 58, "calibators" should be --calibrators--.

Column 24, Line 36, "dromaderius)," should be --dromedarius),--.

Column 24, Line 36, "paccos," should be --pacos,--.

Column 26, Line 64, "$^{125}I$" to --$^{125}I$- --.

Column 43, Line 29, "argninine," should be --arginine,--.

Columns 47-48, Line 13 (approx.), "Mates" should be --Males--.

In the Claims

Column 59, Line 50 (approx.), In Claim 1, after "determining" insert --a--.

Column 59, Line 52 (approx.), In Claim 1, "dyspnea" should be --dyspnea,--.

Signed and Sealed this
Sixteenth Day of April, 2019

Andrei Iancu
*Director of the United States Patent and Trademark Office*